(12) United States Patent
Alocilja et al.

(10) Patent No.: US 6,767,732 B2
(45) Date of Patent: *Jul. 27, 2004

(54) METHOD AND APPARATUS FOR THE DETECTION OF VOLATILE PRODUCTS IN A SAMPLE

(75) Inventors: Evangelyn C. Alocilja, East Lansing, MI (US); Steve A. Marquie, East Lansing, MI (US); Cynthia Meeusen, Lansing, MI (US); Spring M. Younts, Lincoln, NE (US); Daniel L. Grooms, Williamston, MI (US)

(73) Assignee: Board of Trustees of Michigan State University, East Lansing, MI (US)

( * ) Notice: Subject to any disclaimer, the term of this patent is extended or adjusted under 35 U.S.C. 154(b) by 288 days.

This patent is subject to a terminal disclaimer.

(21) Appl. No.: 09/897,542

(22) Filed: Jul. 2, 2001

(65) Prior Publication Data

US 2002/0119513 A1 Aug. 29, 2002

Related U.S. Application Data

(63) Continuation-in-part of application No. 09/593,114, filed on Jun. 12, 2000, now Pat. No. 6,537,802.
(60) Provisional application No. 60/215,924, filed on Jul. 3, 2000.

(51) Int. Cl.[7] .............................. C12M 1/34; C12Q 1/04
(52) U.S. Cl. ................ 435/287.5; 435/288.1; 435/288.7; 435/808; 435/31; 435/34; 436/20; 436/149; 436/171; 422/90; 422/91; 73/23.34; 73/23.36; 73/23.37
(58) Field of Search .................. 435/37, 40, 287.1, 435/287.4, 287.5, 807, 808, 288.7, 31, 34; 436/20, 24, 63, 149, 164, 171; 422/83, 90, 91; 73/23.34, 23.36, 23.37; 250/343; 356/337, 340, 319, 320

(56) References Cited

U.S. PATENT DOCUMENTS

| 5,164,796 A | * 11/1992 | Di Guiseppi et al. ....... 356/445 |
| 5,750,998 A | * 5/1998 | Goldman .................... 250/343 |
| 6,537,802 B1 | * 3/2003 | Alocilja et al. .......... 435/287.5 |

FOREIGN PATENT DOCUMENTS

| EP | 151855 A1 * 8/1985 | ............ C12M/1/34 |
| WO | WO 9533991 A1 * 12/1995 | .......... G01N/33/02 |

OTHER PUBLICATIONS

Gardner et al."The prediction of bacteria type and culture growth phase by an electronic nose with a multi-layer perceptron network." Meas. Sci. Technol. vol. 9 (1998), pp. 120–127.*

Rossi et al. "Rapid discrimination of Micrococcaceae species using semiconductor gas sensor." Journal of Microbiological Methods. vol. 24 (1995), pp. 183–190.*

Younts et al."Differentiation of *E. coli* 0157:H7 from Non00157:H7 serotypes using a gas sensor–based, computer–controlled detection system." Proceedings of the Institute of Biological Engineering. vol. 2 (1999), pp. B29–B34.*

* cited by examiner

Primary Examiner—William H. Beisner
(74) Attorney, Agent, or Firm—Ian C. McLeod

(57) ABSTRACT

A method and apparatus is provided for detection of volatile products from a sample using a transducer which changes voltage as a function of contact of the volatile products with the transducer to produce a gas signature of the volatile products and a spectrophotometer to analyze the volatile products to produce a spectral footprint of the volatile products. The apparatus and method are used to detect spoilage of a biological material, such as a food. The apparatus is also used to detect microorganisms and by comparing the gas signature and spectral footprint to a library of gas signatures and spectral footprints, the apparatus enables identification of the microorganisms and in particular identification of pathogenic microorganisms.

63 Claims, 28 Drawing Sheets

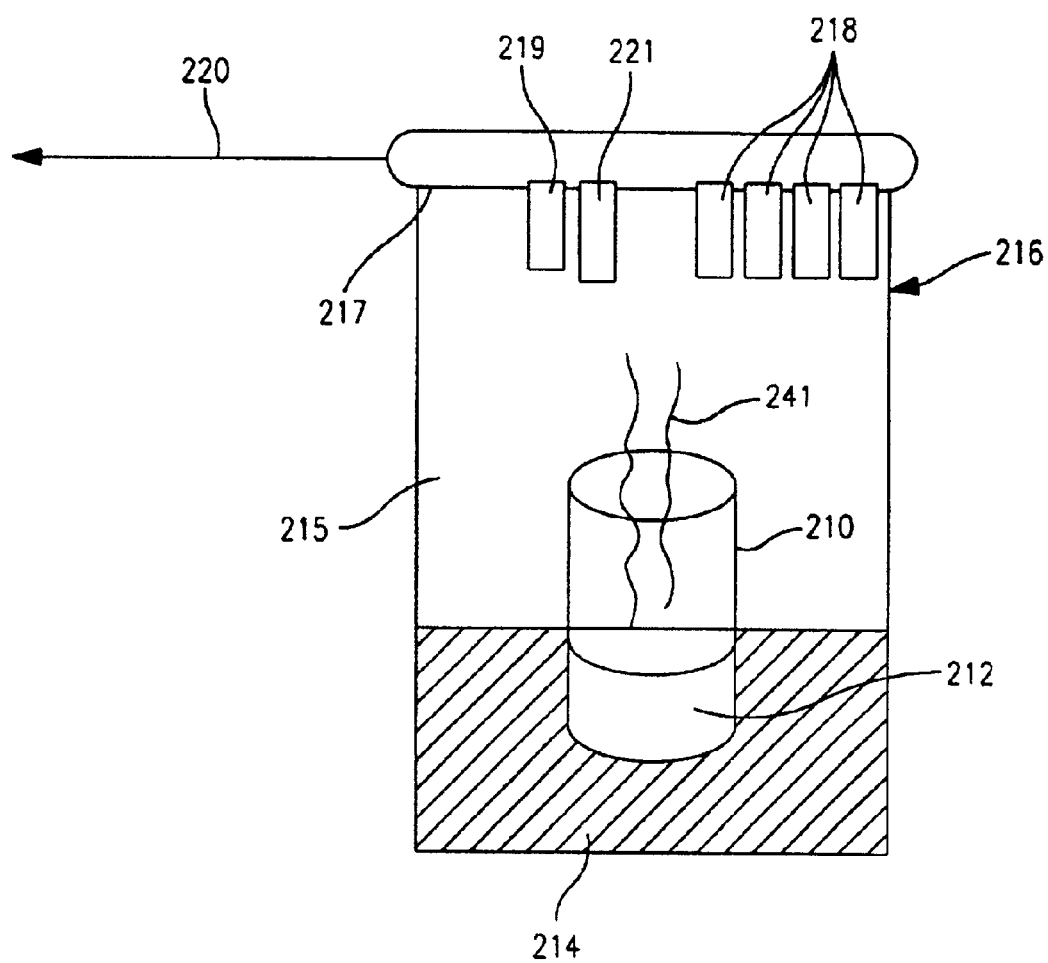
FIG. IA

METHOD AND APPARATUS FOR THE DETECTION OF VOLATILE PRODUCTS IN A SAMPLE

CROSS-REFERENCE TO RELATED APPLICATIONS

This application is a Continuation-in-Part of U.S. application Ser. No. 09/593,114, which was filed Jun. 12, 2000, now U.S. Pat. No. 6,537,802, issued Mar. 25, 2003, and which claims priority to U.S. Provisional Application Serial No. 60/215,924, which was filed Jul. 3, 2000.

STATEMENT REGARDING FEDERALLY SPONSORED RESEARCH OR DEVELOPMENT

Not Applicable.

REFERENCE TO A "COMPACT DISC APPENDIX"

Not Applicable.

BACKGROUND OF THE INVENTION (1) Field of the Invention

The present invention relates to a method and apparatus for detection of volatile products from a sample using a transducer which changes voltage as a function of contact of the volatile products with the transducer to produce a gas signature of the volatile products and a spectrophotometer to analyze the volatile products to produce a spectral footprint of the volatile products. The apparatus and method are used to detect spoilage of a biological material, such as a food. The apparatus is also used to detect microorganisms and by comparing the gas signature and spectral footprint to a library of gas signatures and spectral footprints, the apparatus enables identification of the microorganisms and in particular identification of pathogenic microorganisms.

(2) Description of Related Art

Food safety concerns are currently impacting public health, the meat industry, and animal production agriculture. Animal agriculture has been under increasing scrutiny as a source of foodborne pathogens. There is a need to develop a new technology that can be applied to pre-harvest food safety efforts, particularly for identifying and monitoring a potential human pathogen "on the farm".

Escherichia coli (E. coli) 0157:H7 has been recognized as a significant bacterial pathogen belonging to a group of enterohemorrhagic E. coli associated with bloody diarrhea. It is important public health concern because of its association with commonly consumed foods, such as ground beef. Infection with this organism can cause hemorrhagic colitis, hemolytic uremic syndrome, and thrombotic thrombocytopenic purpura. The association of E. coli 0157:H7 with ground beef has led to the identification of cattle as a reservoir for the organism. Recent pre-harvest food safety efforts have emphasized identifying factors within cattle production systems for the monitoring and control of E. coli 0157:H7.

Computer controlled gas sensor based instruments, referred to as artificial olfactory or electronic nose technology, are finding increasing application in the food industry. The sensors are designed to detect volatile compounds that result from spoilage, rancidity, or other "off" odors. Promising results have been shown when this technology was applied to differentiating between different species of bacteria and spoilage fungi.

In today's farming industry, potatoes are stored in large bins before they are shipped out to their various destinations. Disease during storage is magnified due to extended storage periods and by requiring higher storage temperatures for immediate processing of the potatoes (Varns and Glynn, 1979). Disease losses of potatoes in storage may be as high as 30% (The Grower, 1980). As potato processing contributes up to two billion dollars a year to the economy, a small percentage of disease losses represent a significant cost to the potato industry. Currently, the managers of the potato bins monitor odor and wetness at the bottom of the bin to determine rot. By the time these indicators are detected, economic losses can be significant. At the moment, nothing can be done to arrest the spread of the damage. Monitoring of volatiles arising from host-pathogen interactions could become an important early warning of potato disease problems. Disease due to *Erwinia carotovora* infection is a major problem in potato storage. *Erwinia carotovora* is a facultative anaerobic organism, in which the bacterium breaks down the structure of the vegetative cells of infected potatoes, causing soft rot. This causes a layer of wet slime to form on the outside of the potato, resulting in anaerobic conditions in the underlying cells (Costa and Loper, 1994). Varns and Glynn (1979) reported that potatoes infected with the bacterium *Erwinia carotovora* showed high levels of acetone, ethanol, and 2-butanone. Additional volatiles included acetaldehyde, methyl acetate, ethyl acetate, propanethiol, hydrogen sulfide, methyl sulfide, methyl disulfide, n-propanol, and isobutanol (Varns and Glynn, 1979). Waterer and Pritchard (1984) reported methanol, acetaldehyde, ethanol, 2-propanol, acetone, 1-propanol, and 1-butanol in the headspace of *E. carotovora* var. *carotovora* infected Russet Burbank potato tubers. These volatiles can be produced from intermediates as well as the end-product (pyruvate) of the Embden-Meyerhof pathway (Metzler, 1977).

The sense of smell has long been used as a diagnostic tool by medical professionals, law enforcement, food handlers, and countless others in everyday life. The human nose contains approximately 50 million cells in the olfactory epithelium that act as primary receptors to odorous molecules (Gardner et al., 1990; Vandendorpe, 1998). This parallel architecture led to the construction of the electronic nose, which mimics the biological system. The electronic nose is a state-of-the-art technology that can be used to provide rapid and continuous monitoring of a wide array of different volatile compounds. The term "electronic nose" is applied to an array of chemical sensors, where each sensor has only partial specificity to a wide range of odorant molecules (Bartlett et al., Food Technol. 51: 44–48 (1997)). By mapping the sensitivity of the sensors to different chemicals, a complex odor can be "fingerprinted" and identified (Lipman, 1998). The primary receptors in the biological system are replaced by an array of transducers, such as metal oxide films, that respond to a broad range of chemical vapors or odors. Electronic nose instrumentation has advanced rapidly during the past ten years, the majority of application being within the food and drink industries (Gardner and Bartlett, 1992; Kress-Rogers, 1997). Research is being done on the applications of the electronic nose in human healthcare, particularly in the identification of infection (Doctor's Guide to Medical & Other News. "Electronic Nose Sniffs out Infection"). The instrument has also been successfully applied to detect vapors (Gardner et al., 1990; Keller et al., 1994) and aviation fuels (Lauf and Hoffheins, 1990).

Application in microbial detection has been reported for *Clostridium perfringes*, Proteus, *Haemophilus influenzae*,

*Bacteriodes fragilis, Oxford staphylococcus, Pseudomonas aeruginosa* (Craven et al., 1994), *Staphylococcus aureus*, and *E. coli* (Gardner et al., Measurement Sci. Technol. 9: 120–127 (1998)).

U.S. Pat. No. 5,807,701 to Payne et al. provides a method for identifying a microorganism that includes abstracting gas or vapor associated with the microorganism from a detection region and flowing the same over an array of sensors of which an electrical property varies according to exposure to gases or vapors and observing the response of the sensors. An apparatus for detecting a microorganism is also disclosed having a detector means for detecting a gas or vapor associated with the microorganism which includes an array of sensors of which an electrical property varies according to exposure to the gases or vapors.

U.S. Pat. No. 6,017,440 to Lewis et al. provides a sensor array for detecting a microorganism comprising first and second sensors electrically connected to an electrical measuring apparatus, wherein the sensors comprise a region of nonconducting organic material and a region of conducting material that is different than the nonconducting organic material and an electrical path through the regions of nonconducting organic material and the conducting material. Further provided is a system for identifying microorganisms using the sensor array, a computer and a pattern recognition algorithm, such as a neural net are also disclosed.

U.S. Pat. No. 6,244,096 to Lewis et al. provides a device for detecting the presence of an analyte, wherein the analyte is a microorganism marker gas. The device comprises a sample chamber having a fluid inlet port for the influx of the microorganism marker gas; a fluid concentrator in flow communication with the sample chamber, wherein the fluid concentrator has an absorbent material capable of absorbing the microorganism marker gas and thereafter releasing a concentrated microorganism marker gas; and an array of sensors in fluid communication with the concentrated microorganism marker gas. The sensor array detects and identifies the marker gas upon its release from fluid concentrate.

U.S. Pat. Nos. 6,234,006 and 6,085,576 to Sunshine et al. provides a handheld vapor sensing device for use in sensing the presence and concentration of a wide variety of specified vapors as resulting from gases released during either decomposition and spoilage of food stuffs, or as released into either the breath or body fluids of a sick patient being medically diagnosed.

U.S. Pat. No. 6,212,938 to Staples provides a process whereby the olfactory response of a gas chromatograph, equipped with a focused surface acoustic wave interferometer integrating detector is converted to a visual image for the purpose of performing pattern recognition. As volatile analytes exit a gas chromatography column a Surface Acoustic Wave Interferometer is used to monitor the condensation and re-evaporation of these analytes by periodically measuring the resonant frequency of the interferometer. A time varying output parameter is then converted to a polar display. This form of electronic nose provides a recognizable visual image of specific vapor mixtures (fragrances) containing possibly hundreds of different chemical species.

U.S. Pat. No. 6,190,858 to Persaud et al. provides a method for identifying a micro-organism comprising the steps of providing at least one gas sensor; compiling a database of responses to at least one known micro-organism under a variety of culturing conditions; abstracting gas or vapor from a detection region and flowing the same over at least one gas sensor and observing the response of the sensor or sensors; and comparing the response to the database.

Spectrophotometers are conventional and well known in the prior art. The present invention uses such equipment in a novel manner to detect pathogenic microorganisms and microorganisms that cause spoilage.

SUMMARY OF THE INVENTION

The present invention provides an apparatus for detection of volatile products from a sample which comprises (a) a wall or walls defining a confined space comprising therein an open container for containing the sample which produces the volatile products in the confined space, the open container having a bottom with sidewalls extending upwards therefrom to form the open container and wherein the sidewall has two openings positioned to be opposed to each other, each opening having a collimating lens therein; (b) one or more transducer means in a circuit mounted on an inner surface of the container defining the confined space which detects one or more volatile products of the volatile products produced from the sample to produce an analog signal; (c) an analog to digital conversion means in the circuit for converting the analog signal from the transducer means to a digital signal in the circuit; (d) an acquisition means in the circuit which stores the digital signal resulting from the analog signal in memory as a first detectable signal and retrieves the first detectable signal to provide the detection of the one or more volatile products, wherein the one or more volatile products in the confined space are detected by the one or more transducer means over time to produce a gas signature; and (e) a spectrophotometer coupled to the collimating lenses by fiber optics wherein one lens is coupled to the fiber optics from the light source in the spectrophotometer and the opposite lens is coupled to the fiber optics to the light detector in the spectrophotometer so that light absorption or scattering caused by a multiple of the volatile products in the confined space from the sample are detected by the spectrophotometer, to produce a second detectable signal which is a spectral footprint which is stored.

In a particular embodiment, the apparatus detects the multiple of volatile products produced by a microorganism in the sample, in particular, wherein the microorganism is pathogenic such as a pathogenic *Escherichia coli* or a *Salmonella* sp. In any one of the embodiments of the apparatus, the volatile product detected by the apparatus is selected from the group consisting of ammonia, ammonium compounds, sulfides, amines, ketones, alcohols, methane, butanes, oxides, carbon dioxide, and other gaseous compounds.

In a further embodiment of the apparatus, the acquisition means is a computer with a video screen for visualizing the gas signature and spectral footprint or a computer with a video screen for visualizing the gas signature and spectral footprint and in addition the gas signature and spectral footprint are recorded in a graph.

In a further embodiment of the apparatus, the computer further comprises an artificial neural network to analyze the gas signature and the spectral footprint by comparing the gas signature and the spectral footprint to a library of gas signatures and spectral footprints stored in the computer.

In a further embodiment of the apparatus, the one or more transducer means are mounted in the confined space wherein at least a part of the wall or walls is removable for sealing and unsealing.

In a further embodiment of the apparatus, at least one resistor is provided in the circuit with the one or more transducer means to enable reproducible results from the one or more transducer means.

In a further embodiment of the apparatus, the analog to digital conversion means is a 12-bit multiple channel analog to digital converter.

In a further embodiment of the apparatus, further including a heating block with an opening for holding the open container to maintain the sample at a particular temperature.

The present invention further provides a method for detecting volatile products from a sample comprising (a) providing an apparatus adjacent to the sample which comprises: a circuit comprising one or more transducer means mounted on an inner surface of a wall or walls defining a confined space which contains therein an open container for containing the sample which produces the volatile products in the confined space, the open container having a bottom with sidewalls extending upwards therefrom to form the open container and wherein the sidewall has two openings positioned to be opposed to each other, each opening having a collimating lens therein, and wherein the one or more transducer means in the circuit detects one or more volatile products of the volatile products from the sample to produce an analog signal in the circuit; an analog to digital conversion means in the circuit for converting the analog signal from the transducer means to a digital signal; an acquisition means in the circuit, which stores the digital signal resulting from the analog signal in a memory as a first detectable signal and retrieves the first detectable signal to provide the detection of the one or more volatile products from the sample, wherein the one or more volatile products in the confined space from the sample are detected by the one or more transducer means over time to produce a gas signature; a spectrophotometer coupled to the collimating lenses by fiber optics wherein one lens is coupled to the fiber optics from the light source in the spectrophotometer and the opposite lens is coupled to the fiber optics to the light detector in the spectrophotometer so that light absorption or scattering caused by a multiple of the volatile products in the confined space from the sample are detected by the spectrophotometer to produce a second detectable signal which is a spectral footprint which is stored; and (b) detecting the one or more volatile products in the confined space from the sample with the one or more transducer means in the circuit, wherein the one or more volatile products in the confined space from the sample are detected over time to produce the gas signature and wherein the multiple of the volatile products in the confined space from the sample are detected by the spectrophotometer to produce the spectral footprint.

In a particular embodiment of the method, the volatile by-product is selected from the group consisting of ammonia, ammonium compounds, sulfides, amines, ketones, alcohols, methane, butanes, oxides, carbon dioxide, and other gaseous compounds, which is detected repeatedly over a period of time. In one embodiment, the ammonium is produced by a microorganism such as a pathogenic *Escherichia coli*.

In a further embodiment of the method, the sample in the open container is placed in the confined space which is sealable which is then sealed, and wherein the one or more transducer means are adjacent to the sample in the sealed container.

In a further embodiment of the method, the acquisition means further includes an artificial neural network to compare the gas signature and the spectral footprint to the library of gas signatures and spectral footprints stored in the computer.

In a further embodiment of the method, the apparatus further includes a heating block with an opening for holding the open container to maintain the sample at a particular temperature.

The present invention further provides an apparatus for determining whether a food material is spoiling by detecting volatile by-products of the spoiling which comprises (a) a circuit comprising one or more transducer means mounted on an inner surface of a wall or walls defining a confined space having therein an open container for containing the food material in the confined space which produces the volatile products, the open container having a bottom with sidewalls extending upwards therefrom to form the open container and wherein the sidewall has two openings positioned to be opposed to each other, each opening having a collimating lens therein, and wherein the one or more transducer means in the circuit detects one or more volatile by-products of the volatile by-products produced in the confined space to produce an analog signal in the circuit; (b) an analog to digital converter means in the circuit for converting the analog signal from the transducer means to a digital signal; (c) an acquisition means in the circuit which stores the digital signal resulting from the analog signal in a memory as a first detectable signal and retrieves the first detectable signal to produce the detection of the one or more volatile by-products wherein the one or more volatile by-products are detected by the transducer means over time to produce a gas signature of the one or more volatile by-products; and (d) a spectrophotometer coupled to the collimating lenses by fiber optics, wherein one lens is coupled to the fiber optics from the light source in the spectrophotometer and the opposite lens is coupled to the fiber optics to the light detector in the spectrophotometer so that light absorption or scattering caused by a multiple of the volatile by-products in the confined space from the sample are detected by the spectrophotometer to produce a second signal which is a spectral footprint of the multiple of volatile by-products which is stored.

In a further embodiment of the apparatus, the transducer means detects a fermentation by-product produced by the microorganism.

In a further embodiment of the apparatus, the food material is selected from the group consisting of vegetables, fruits, meats, grains, herbs, spices, and legumes.

In a further embodiment of the apparatus, the circuit further comprises a transducer means which detects temperature.

In a further embodiment of the apparatus, the circuit further comprises a transducer means which detects humidity.

In a further embodiment of the above embodiments of the apparatus, the acquisition means is in a computer with a video screen for visualizing the gas pattern and spectral footprint.

In a further embodiment of the above embodiments of the apparatus, the acquisition means is in a computer with a video screen for visualizing the gas pattern and the spectral footprint and wherein the gas pattern and the spectral footprint are recorded in a graph.

In a further embodiment of the above embodiments of the apparatus, the transducer means in addition detects temperature, wherein the transducer means in addition detects humidity; and wherein the acquisition means is in a computer which detects each of the humidity, the temperature and the one or more volatile by-products to produce a series of first detectable signals which are reproducible over a series of detections.

In a further embodiment of the apparatus, the one or more transducer means are mounted in the confined space wherein at least a part of the wall or walls is removable for sealing and unsealing.

In a further embodiment of the apparatus, the transducer means is mounted on a cover for the sealable container.

In a further embodiment of the apparatus, at least one resistor is provided in the circuit with the transducer means to enable reproducible results from the transducer means.

In a further embodiment of the apparatus, at least one resistor is provided in the circuit with the transducer means to enable reproducible results from the transducer means and wherein the resistor is mounted outside of the container.

In a further embodiment of the apparatus, the converter means is a 12-bit multiple channel analog to digital converter.

In a further embodiment of the apparatus, the apparatus further includes a heating block with an opening for holding the open container to maintain the sample at a particular temperature.

The present invention also provides a method for determining whether a biological material is spoiling by detecting volatile by-products which comprises (a) providing an apparatus for detecting the volatile by-products produced by the spoiling which comprises: a circuit comprising one or more transducer means mounted on an inner surface of a wall or walls defining a confined space having therein an open container for containing the biological material which produces the volatile products in the confined space, the open container having a bottom with sidewalls extending upwards therefrom to form the open container and wherein the sidewall has two openings positioned to be opposed to each other, each opening having a collimating lens therein, and wherein the one or more transducer means in the circuit detects one or more of the volatile by-products of the volatile by-products produced in the confined space by the biological material to produce an analog signal; an analog to digital converter means in the circuit for converting the analog signal from the transducer means to a digital signal; an acquisition means in the circuit which stores the digital signal resulting from the analog signal in memory as a first detectable signal and retrieves the first detectable signal wherein the one or more volatile by-products in the confined space from the biological material are detected by the one or more transducer means over time to produce a gas signature of the one or more volatile by-products; and a spectrophotometer coupled to the collimating lens by fiber optics wherein one lens is coupled to the fiber optics from the light source in the spectrophotometer and the opposite lens is coupled to the fiber optics to the light detector in the spectrophotometer so that light absorption or scattering caused by a multiple of the volatile by-products in the confined space is detected by the spectrophotometer to produce a second detectable signal which is a spectral footprint of the multiple of volatile by-products which is stored; and (b) detecting the one or more volatile by-products of the microorganism with the transducer means in the circuit wherein the one or more volatile by-products in the confined space from the biological material is detected over time to produce the gas signature and wherein the multiple of the volatile products are detected in the confined space by the spectrometer to produce the spectral footprint; and (c) comparing the gas signature and the spectral footprint to a library including a plurality of gas signatures and spectral footprints produced by a plurality of biological materials at different stages of spoilage to determine whether the biological material is spoiling.

In one embodiment of the method, the biological material is a food positioned adjacent to the transducer means.

In a further embodiment of the method, the volatile by-product is an alcohol.

In a further embodiment of the method, the biological material is selected from the group consisting of vegetables, fruits, meats, grains, herbs, spices, and legumes and the volatile by-product is an alcohol.

In a further embodiment of the method, the biological material in the open container is placed in the confined space which is sealable which is then sealed, and wherein the one or more transducer means are adjacent to the sample in the sealed container.

In a further embodiment of the method, the acquisition means is a computer with an artificial neural network to compare the gas signature and the spectral footprint to the library of gas signatures and spectral footprints.

In a further embodiment of the method, the apparatus further includes a heating block with an opening for holding the open container to maintain the sample at a particular temperature.

The present invention further provides an apparatus for identifying a microorganism in a biological material by detecting volatile by-products produced by the microorganism which comprises (a) a circuit comprising one or more transducer means mounted on an inner surface of a wall or walls defining a confined space having therein an open container for containing the biological material with the microorganism which produces the volatile products in the confined space, the open container having a bottom with sidewalls extending upwards therefrom to form the open container and wherein the sidewall has two openings positioned to be opposed to each other, each opening having a collimating lens therein, and wherein the one or more transducer means in the circuit detects one or more volatile by-products of the volatile by-products produced in the confined space by the microorganism in the biological material to produce an analog signal in the circuit; (b) an analog to digital converter means in the circuit for converting the analog signal from the transducer means to a digital signal; (c) an acquisition means in the circuit which stores the digital signal resulting from the analog signal in a memory as a first detectable signal and retrieves the first detectable signal to produce the detection of the one or more volatile by-products wherein the one or more volatile by-products are detected by the one or more transducer means over time to produce a gas signature; and (d) a spectrophotometer coupled to the collimating lenses by fiber optics wherein one lens is coupled to the fiber optics from the light source in the spectrophotometer and the opposite lens is coupled to the fiber optics to the light detector in the spectrophotometer so that light absorption or scattering caused by a multiple of volatile by-products from the microorganism in the biological material in the confined space are detected by the spectrophotometer to produce a second signal over time which is stored as a spectral footprint.

In one embodiment of the apparatus, the transducer means detects a fermentation by-product produced by the microorganism.

In a further embodiment of the apparatus, the biological material is selected from the group consisting of vegetables, fruits, meats, grains, herbs, spices, and legumes.

In a further embodiment of the apparatus, the circuit further comprises a transducer means which detects temperature.

In a further embodiment of the apparatus, the circuit further comprises a transducer means which detects humidity.

In a further embodiment of the above embodiments of the apparatus, the acquisition means is in a computer with a video screen for visualizing the gas signature and spectral footprint.

In a further embodiment of the above embodiments of the apparatus, the acquisition means is in a computer with a video screen for visualizing the gas signature and spectral footprint and wherein the gas signature and spectral footprint are recorded in a graph.

In a further embodiment of the apparatus, the acquisition means is a computer with an artificial neural network to identify the microorganism by comparing the gas signature and the spectral footprint to a library including a plurality of gas signatures and spectral footprints produced by a plurality of microorganisms stored in the computer.

In a further embodiment of the above embodiments of the apparatus, the transducer means in addition detects temperature, wherein the transducer means in addition detects humidity; and wherein the acquisition means is in a computer which detects each of the humidity, the temperature and the volatile by-products to produce a series of first detectable signals which are reproducible over a series of detections.

In a further embodiment of the apparatus, the one or more transducer means are mounted in the confined space wherein at least a part of the wall or walls is removable for sealing and unsealing.

In a further embodiment of the apparatus, the transducer means is mounted on a cover for the sealable container.

In a further embodiment of the apparatus, at least one resistor is provided in the circuit with the transducer means to enable reproducible results from the transducer means.

In a further embodiment of the apparatus, at least one resistor is provided in the circuit with the transducer means to enable reproducible results from the transducer means and wherein the resistor is mounted outside of the container.

In a further embodiment of the apparatus, the converter means is a 12-bit multiple channel analog to digital converter.

In a further embodiment of the apparatus, the apparatus further includes a heating block with an opening for holding the open container to maintain the biological material at a particular temperature.

The present invention further provides a method for identifying a microorganism in a biological material by detecting a multiple of volatile by-products produced by the microorganism which comprises (a) providing an apparatus for the detection of the pattern of the multiple of volatile by-products produced by a microorganism which comprises: a circuit comprising one or more transducer means mounted on an inner surface of a wall or walls defining a confined space having therein an open container for containing the biological material with the microorganism which produces the volatile products in the confined space, the open container having a bottom with sidewalls extending upwards therefrom to form the open container and wherein the sidewall has two openings positioned to be opposed to each other, each opening having a collimating lens therein, and wherein the one or more transducer means in the circuit detects one or more volatile by-products of the by-products produced by the microorganism in the biological material to produce an analog signal; an analog to digital converter means in the circuit for converting the analog signal from the transducer means to a digital signal; an acquisition means in the circuit which stores the digital signal resulting from the analog signal in memory as a first detectable signal and retrieves the first detectable signal to produce a gas signature of the one or more volatile by-products in the confined space; and a spectrophotometer coupled to the collimating lens by fiber optics wherein one lens is coupled to the fiber optics from the light source in the spectrophotometer and the opposite lens is coupled to the fiber optics to the light detector in the spectrophotometer so that light absorption or scattering caused by a multiple of the volatile products in the confined space is detected by the spectrophotometer to produce a second detectable signal which is stored as a spectral footprint; (b) detecting the one or more volatile by-products in the confined space produced by the microorganism in the biological material with the transducer means in the circuit wherein the one or more volatile by-products is detected over time to produce the gas signature and wherein a multiple of the volatile products in the confined space are detected by the spectrometer to produce the spectral footprint; and (c) comparing the gas signature and the spectral footprint to a library including a plurality of gas signatures and spectral footprints produced by a plurality of microorganisms stored in the acquisition means to identify the microorganism.

In a one embodiment of the method, the biological material is a food positioned adjacent to the transducer means.

In a further embodiment of the method, the volatile by-product is an alcohol.

In a further embodiment of the method, the biological material is selected from the group consisting of vegetables, fruits, meats, grains, herbs, spices, and legumes and the volatile by-product is an alcohol.

In a further embodiment of the method, the biological material in the open container is placed in the confined space which is sealable which is then sealed, and wherein the one or more transducer means are adjacent to the sample in the sealed container.

In a further embodiment of the method, the acquisition means is a computer with an artificial neural network to compare the gas signature and the spectral footprint to the library of gas signatures and spectral footprints.

In a further embodiment of the method, the apparatus further includes a heating block with an opening for holding the open container to maintain the sample at a particular temperature.

Objects

It is therefore an object of the present invention to provide an apparatus and method for the detection of very small amounts of a volatile product (less than $10^{-1}$) parts of a volatile material per part by volume of an atmosphere around a sample. In particular, the present invention provides a detecting apparatus which uses artificial intelligence in the form of a neural network to detect a signature showing the presence of the volatile material in a sample.

Further still, it is an object of the present invention to provide an apparatus and method for the detection of harmful microorganisms by measuring volatile products produced by the microorganism. Further, it is an object of the present invention to provide an apparatus and method for the detection of spoilage by-products produced by microorganisms or degradative oxidation in foods and other biological materials.

These and other objects will become increasingly apparent by reference to the following description and the drawings.

BRIEF DESCRIPTION OF THE DRAWINGS

FIGS. 1 and 1A are schematics of the gas sensor component of the apparatus of the present invention for microorganism detection.

DESCRIPTION OF PREFERRED EMBODIMENTS

Figure 1:
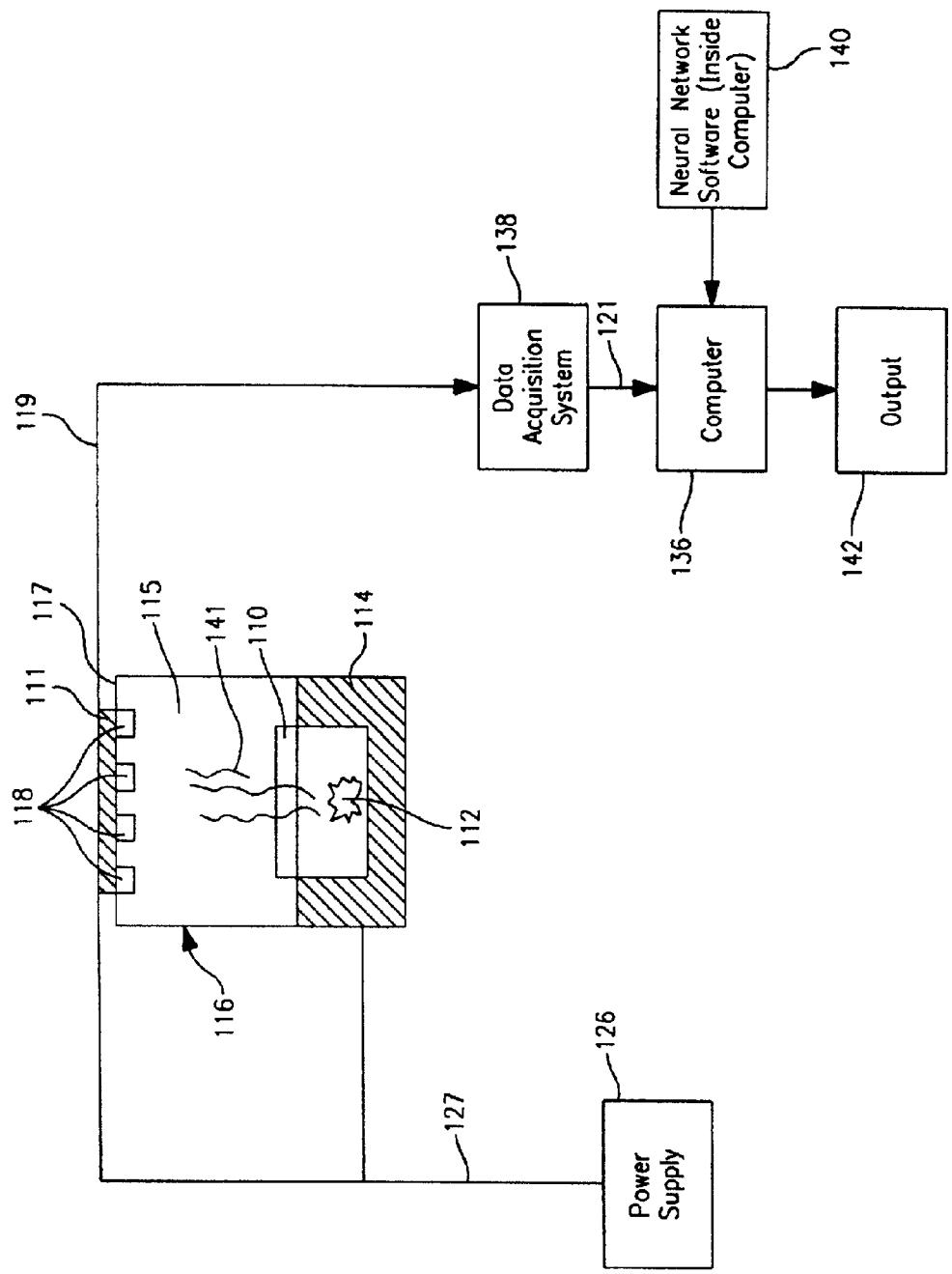

All patents, patent applications, government publications, government regulations, and literature references cited in this specification are hereby incorporated herein by reference in their entirety. In case of conflict, the present description, including definitions, will control.

The development of a detection method that is rapid, less labor intensive, and more economically feasible would greatly enhance food safety monitoring efforts. In field research or management systems, it is not always as important to gain an understanding of the immunological or genetic properties of the organism as it is to identify the presence of the pathogen. Transducers such as gas sensors can detect and identify specific compounds or products instantaneously and monitor them over time. The gas sensors provide a convenient and inexpensive monitoring tool for certain compounds or volatiles gases, such as volatile breakdown products of bacterial metabolism that include, but are not limited to, ammonia, ammonium compounds, sulfides, amines, ketones, alcohols, methane, butanes, oxides, carbon dioxide, and other gaseous compounds that are a product of bacterial metabolism. In addition, gaseous compounds have characteristic light absorption and/or scattering patterns. This spectral pattern, which is referred to as "spectral footprint," together with the gas signatures generated from the gas sensors, would make possible a complete recognition of a microorganism by the volatile breakdown products it produces. The present invention enables the detection and identification of microorganisms that cause disease or cause spoilage by the gas signature and spectral footprint of the volatile breakdown products produced by the microorganism.

Therefore, the present invention provides an apparatus and method for "seeing" and "sniffing" volatile compounds emitted from microorganisms that cause disease or spoilage. The invention uses transducers such as gas sensors to "sniff" the volatile compounds that are produced by the microorganisms in the sample to generate a gas signature of the volatile compounds produced and uses a ultraviolet/visible/ near infrared (UV/vis/NIR) fiber optic spectrometer with an excitation source from the ultraviolet to the near infrared regions of the light spectrum to "see" the spectral footprint of the volatile compounds produced. The combination of the gas signature and spectral footprint provides a definitive identification of the microorganism in the sample, which enables the determination of whether the microorganism is a microorganism that causes disease or spoilage.

The transducer- and spectrophotometer-based apparatus of the present invention further includes an artificial neural network (ANN), which is capable by pattern recognition analysis of distinguishing microorganisms that cause disease or spoilage from microorganisms that do not cause disease or spoilage by detecting the volatile compounds that are emitted by the microorganism. Because each microorganism species differs in the volatile compounds it produces, the gas signature and spectral footprint for each microorganism species is unique to that species.

In practice, the gas signatures and the spectral footprints produced by microorganisms in a sample are analyzed by ANN and compared to a library of standard gas signatures and spectral footprints for a plurality of microorganisms. When both the gas signature and spectral footprint produced from the sample matches a gas signature and spectral footprint in the library, the microorganism in the sample is identified. Because both the gas signature and the spectral footprint must match to indicate the presence of the microorganism, the present invention is more specific than either a gas sensor or spectrophotometer alone. Using the gas sensors of the present invention, the present invention enabled the human pathogen E. coli 0157:H7 to be distinguished from non-0157:H7 E. coli isolates by detecting and measuring the volatile compounds that were emitted by the bacteria. The present invention is further able to identify food products that have spoiled.

Figure 2:
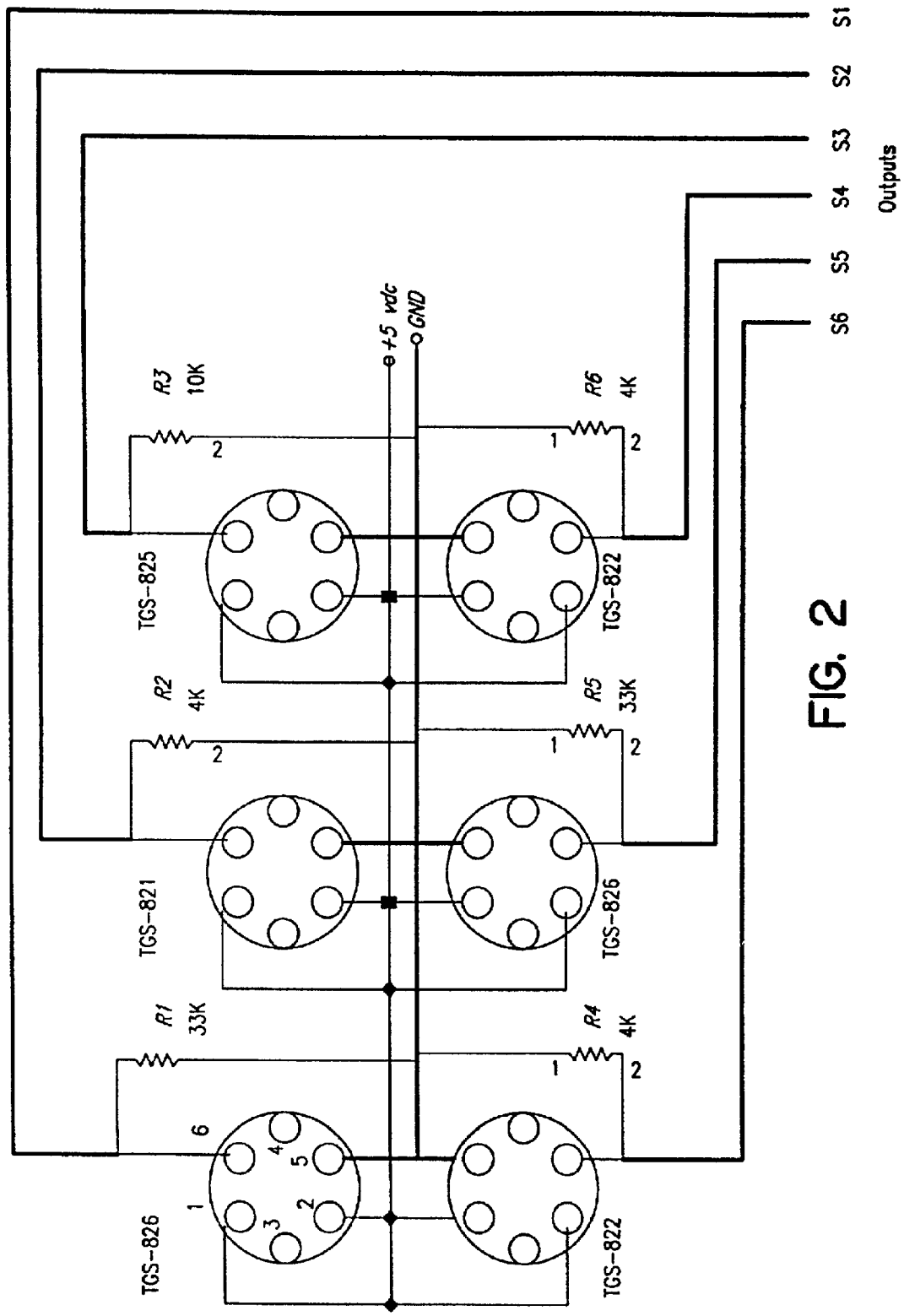
FIG. 2 is a schematic showing the sensor circuit.
Figure 25:
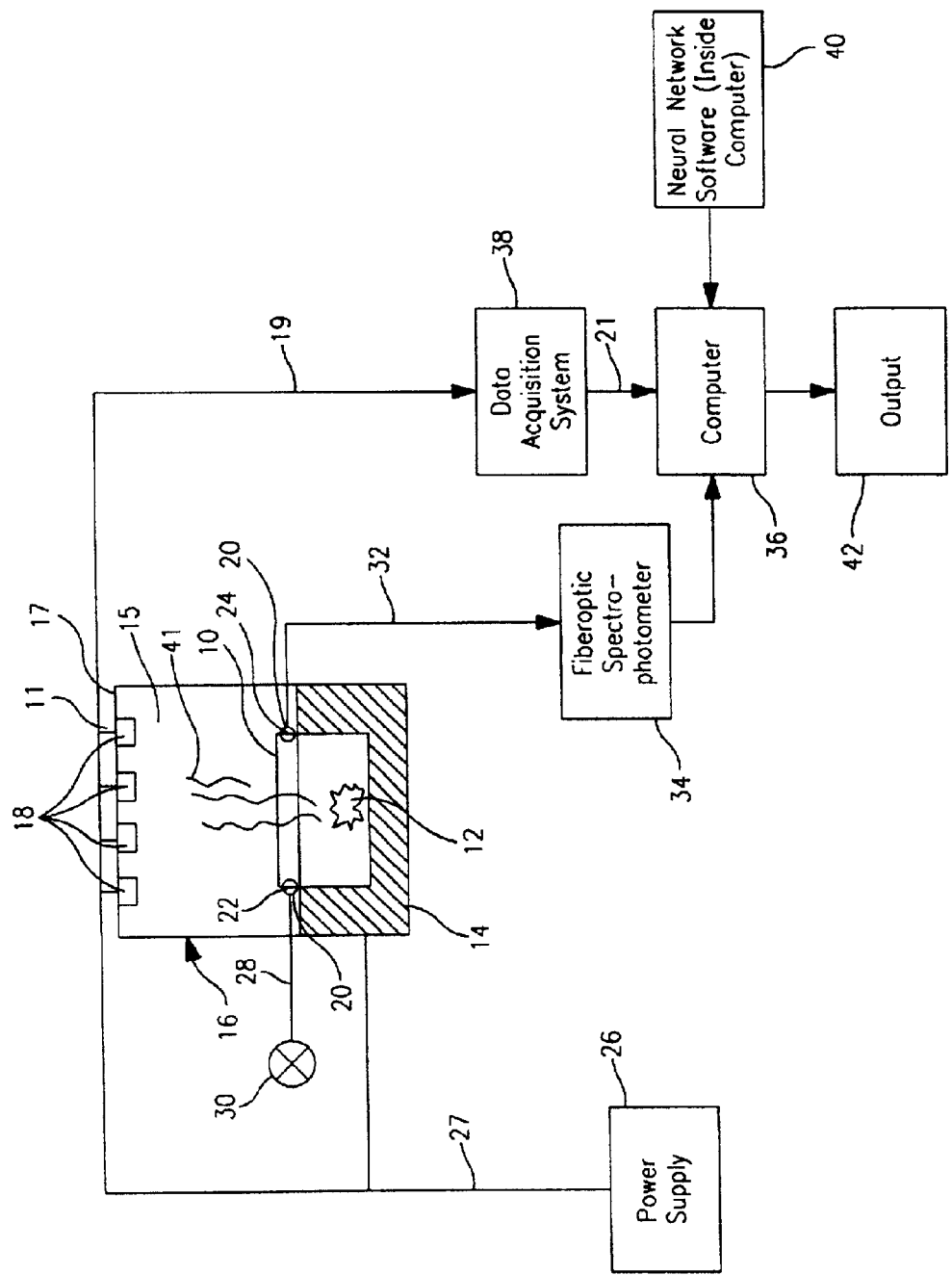
FIG. 25 is a schematic diagram of the transducer apparatus with a spectrophotometer apparatus.

FIG. 25 shows a diagram of the apparatus of the present invention. The figure shows open container or cuvette 10 containing sample 12 in heating block 14. Positioned over the open container 10 in heating block 14 is chamber 16 with transducers 18 mounted on circuit board 11 wall 17 to define a confined space 15 which encloses open container 10. The confined space 15 allows the volatile products 41 from sample 12 to accumulate to an amount which is detectable. Optionally, the chamber can be under a reduced atmosphere. Preferably, the transducers 18 are gas sensors which include, but are not limited to, alcohol sensors, $H_2S$ sensors, amine sensors, methane sensors, hydrogen sensors, alcohol vapor sensors, and air contaminants sensors. A schematic of a typical sensor circuit is shown in FIG. 2. Preferably, further included are temperature and relative humidity transducers (not shown). Power supply 26 provides current 27 to heating block 14 to maintain heating block 14 at a particular temperature and to provide operating current to gas sensors 18.

Figure 2A:
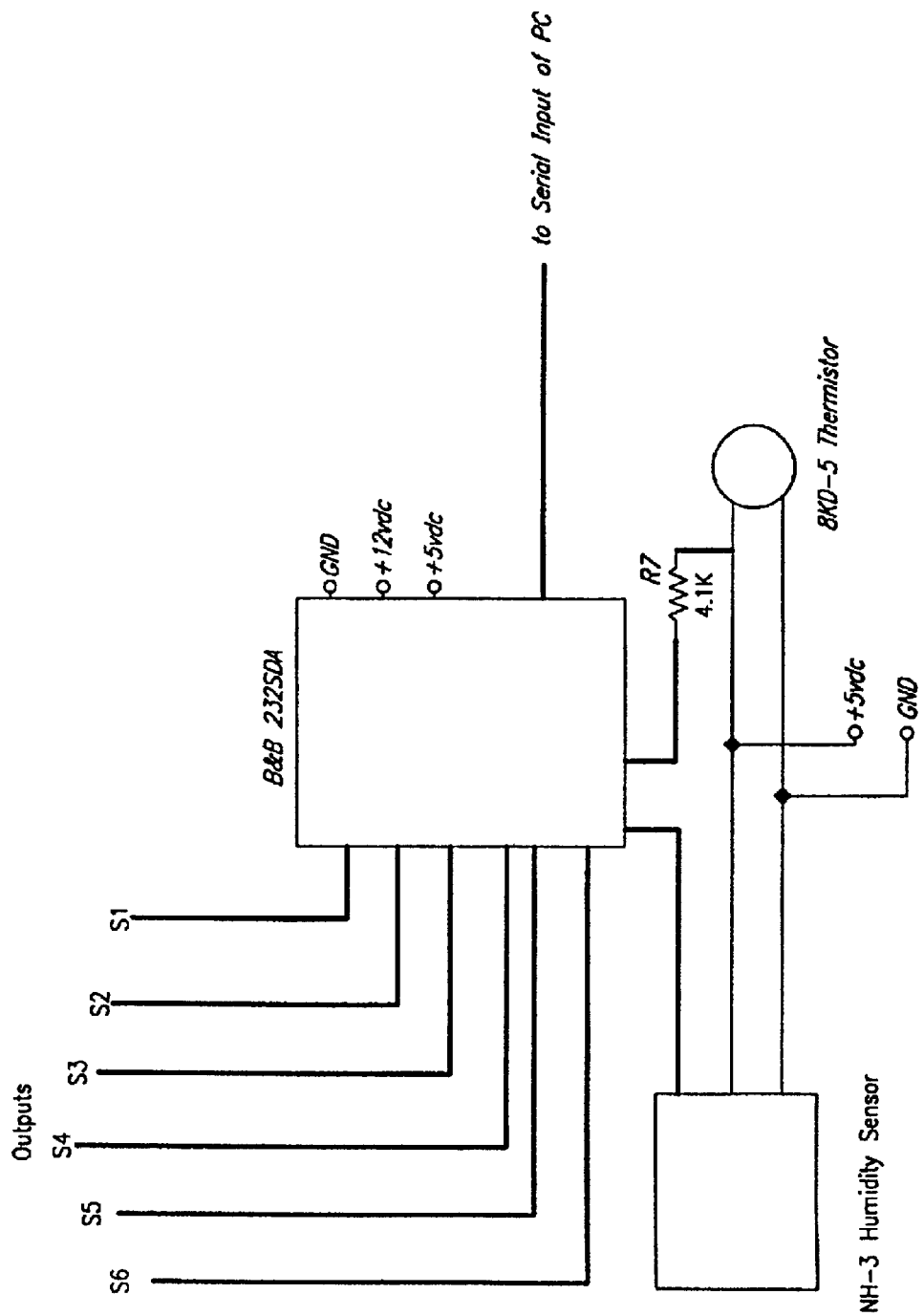
FIG. 2A is a schematic diagram showing the data acquisition circuit of FIG. 1.
Figure 18:
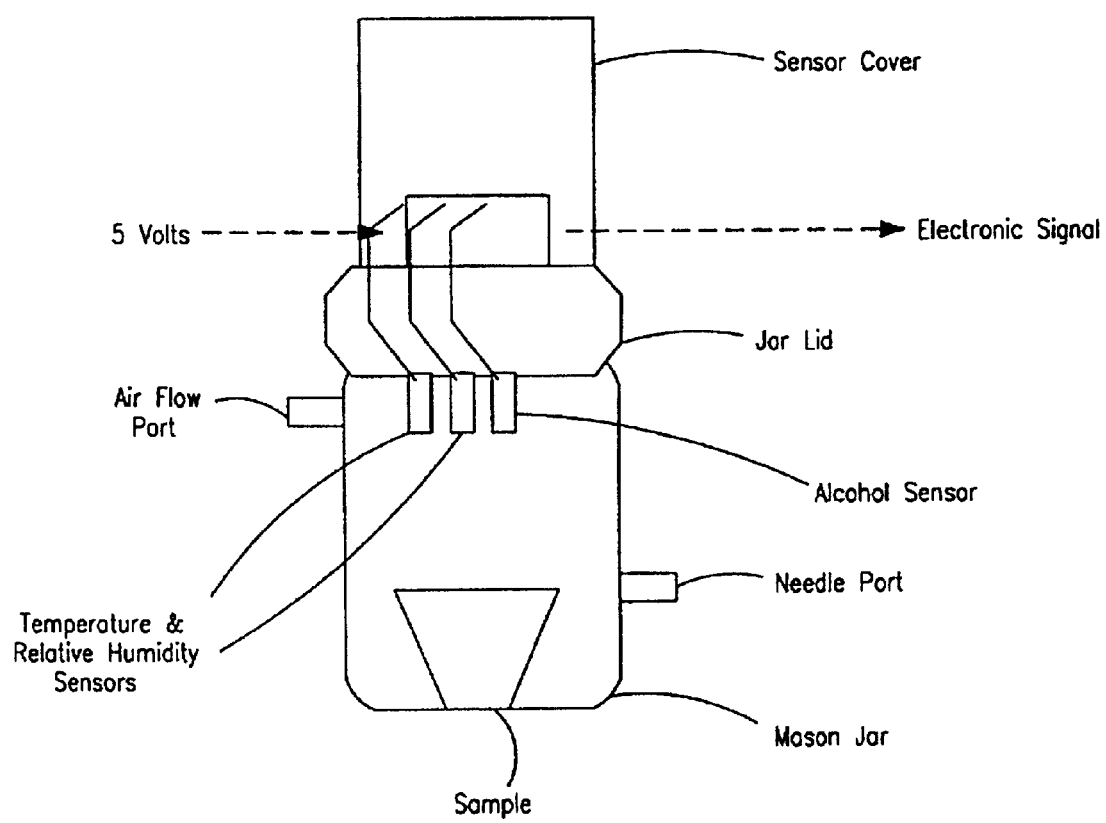
FIG. 18 is a schematic diagram of the apparatus used as a rot sniffer.
Figures 18A, 18B:
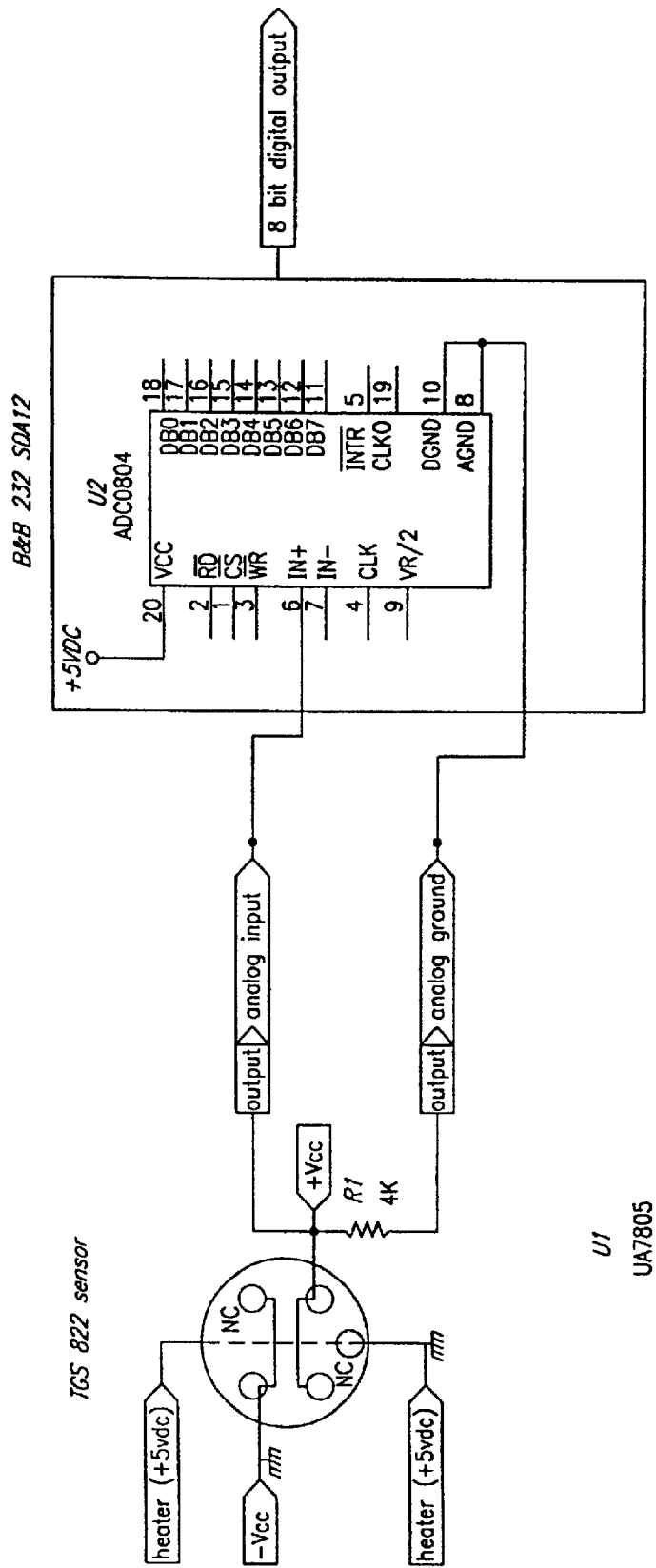
FIG. 18A shows the diagram for the TGS 822 (Figaro, Japan) sensor (transducer) and B&B 232 SDA12 A to D converter.
FIG. 18B shows the heater circuit.

Positioned on opposite sides of the sidewall 20 of open container 10 are collimating lens 22 and collimating lens 24. Lens 22 is operably connected by fiber optic cable 28 to a UV/vis/NIR lamp 30. Fiber optic cable 32 is operably connected to fiber optic spectrophotometer 34. Light is transmitted from the UV/vis/NIR lamp 30 through optic fiber cable 28 to collimating lens 22. The light is transmitted through volatile vapors 41 and collected by collimating lens 24 which transmits the light through fiber optic cable 32 to spectrophotometer 34. Spectrophotometer 34 converts the light to a digital signal which the spectrophotometer 34 then transmits to computer 36. Sensors 18 which can detect particular volatile products in the volatile products 41 produce an analog signal in the sensor circuit board 11, the strength of which is concentration dependent. The analog signal from transducers 18 is then transmitted by sensor circuit 19 to data acquisition system 38 which converts the analog signal to a digital signal which is then transmitted by circuit 21 to computer 36. FIGS. 2A and 18B show schematic diagrams of a data acquisition circuit for converting the analog signal from the transducers 18 to a digital signal. FIG. 18B shows a schematic diagram of an alcohol sensor (TGS 822 sensor) in circuit with data acquisition system B&B 232 SDA12.

Computer 36 converts the digital output from the transducers 18 to a gas signature and converts the digital signal from the spectrophotometer 34 to a spectral footprint. Computer 36 further contains artificial neural network software 40 which compares the gas signature and spectral footprint obtained from the volatile products 41 from the sample 12 to a library of gas signatures and spectral footprints to produce output 42 which is the identification of the source for the volatile products. Preferably, the output 42 is visually displayed as a graph or text on a monitor (not shown) or the graph or text is printed from a printer (not shown).

The artificial olfactory component or electronic nose of the present invention allows differentiation of odors and various volatile products (Bartlett et al., Food Tech 51: 44–48 (1997)). An electronic nose is a device usually consisting of transducers comprising metal oxide gas sensors coupled with an artificial neural network. Analysis of compounds using this technology has been shown to be rapid, nondestructive, economical and continuous (Bartlett et al., Food Tech 51: 44–48 (1997)). The metal oxide sensors are based on the principle that the electrical resistance established in a gas sensor is decreased in the presence of specific volatile compounds. The specificity of the gas sensor is determined by the metal oxide used in the gas sensor. Gas sensor resistance drops very quickly in the presence of a specific gas and recovers to its original level in the absence of the gas. A simple electrical circuit can convert the change in conductivity to an output signal that corresponds to the gas concentration (Figaro USA, 1996). The output signal is reported as a voltage reading that is transferred to a computer software program for continuous plotting, and generating a gas signature or pattern, which is analyzed by the ANN. The transducers or gas sensors that can be included in the apparatus of the present invention include, but are not limited to, alcohol sensors, $H_2S$ sensors, amine sensors, methane sensors, hydrogen sensors, alcohol vapor sensors, and air contaminants sensors.

FIG. 1 shows a diagram of the gas sensor component of the apparatus of the present invention. The figure shows open container or cuvette 110 containing sample 112 in heating block 114. Positioned over the open container 110 in heating block 114 is chamber 116 with transducers 118 mounted on circuit board 111 on wall 117 to define a confined space 115 which encloses open container 110. The confined space 115 allows the volatile products 141 from sample 112 to accumulate to an amount which is detectable. Optionally, the chamber can be under a reduced atmosphere. Preferably, the transducers 118 are gas sensors which include, but are not limited to, alcohol sensors, $H_2S$ sensors, amine sensors, methane sensors, hydrogen sensors, alcohol vapor sensors, and air contaminants sensors. A schematic of a typical sensor circuit it shown in FIG. 2. Preferably, further included are temperature and relative humidity transducers (not shown). Power supply 126 provides current 127 to heating block 114 to maintain heating block 114 at a particular temperature and to provide operating current to gas sensors 118.

Sensors 118 which can detect particular volatile products in the volatile products 141 produce an analog signal in the sensor circuit board 111, the strength of which is concentration dependent. The analog signal from transducers 118 is then transmitted by sensor circuit 119 to data acquisition system 138 which converts the analog signal to a digital signal which is then transmitted by circuit 121 to computer 136. FIGS. 2A and 18B show schematic diagrams of a data acquisition circuit for converting the analog signal from the transducers 118 to a digital signal. FIG. 18B shows a schematic diagram of an alcohol sensor (TGS 822 sensor) in circuit with data acquisition system B&B 232 SDA12.

Computer 136 converts the digital output from the transducers 118 to a gas signature. Computer 136 further contains artificial neural network software 140 which compares the gas signature obtained from the volatile products 141 from the sample 112 to a library of gas signatures to produce output 142 which is the identification of the source for the volatile products. Preferably, the output 142 is visually displayed as a graph or text on a monitor (not shown) or the graph or text is printed from a printer (not shown).

FIG. 1A shows a diagram of the chamber for the gas sensor component of the apparatus of the present invention. The figure shows open container or cuvette 210 containing sample 212 in heating block 214. Positioned over the open container 210 in heating block 214 is chamber 216 with transducers 218 mounted on circuit board 211 wall 217 to define a confined space 215 which encloses open container 210. The confined space 215 allows the volatile products 241 from sample 212 to accumulate to an amount which is detectable. Optionally, the chamber can be under a reduced atmosphere. Preferably, the transducers 218 are gas sensors which include, but are not limited to, alcohol sensors, $H_2S$ sensors, amine sensors, methane sensors, hydrogen sensors, alcohol vapor sensors, and air contaminants sensors. A schematic of a typical sensor circuit it shown in FIG. 2. Also shown is a temperature transducer 219 and relative humidity transducer 221. Further shown is circuit 220 which transmits the signal from the transducers to the data acquisition system (not shown).

Gaseous compounds have characteristic light absorption, reflection, and scattering patterns. This spectral pattern or spectral footprint is used to make a microorganism recognition. The spectral pattern is digitized and transferred to a computer software program for continuous plotting generating a spectral pattern, which is analyzed by the ANN.

The artificial neural network (ANN) used for data analysis or pattern recognition of the gas signature and spectral footprints is an information processing system that functions similar to the way the brain and nervous system process information (Tuang et al., FEMS Microbiol. Letts. 177: 249–256 (1999)). The ANN is trained for the analysis and then tested to validate the method. In the training process, the ANN is configured for pattern recognition, data classification, and forecasting. Commercial software programs are available for this type of data analysis. Recent advances with electronic nose technology have found applications in the food industry for enhancing traditional quality control techniques, based on the ability to detect rancidity, spoilage, and "off" odors (Bartlett et al., Food Tech. 51: 44–48 (1997)).

The following examples are intended to promote a further understanding of the present invention.

EXAMPLE 1

This example shows the development and evaluation of the gas sensing component of the present invention for identifying E. coli 0157:H7 in a laboratory setting.

To reduce the incidence of human exposure to this foodborne pathogen, it is important to establish monitoring and control strategies throughout meat production and processing (Buchanan and Doyle, Food Technol. 51: 69–76 (1997)). Currently, there is still a need for research focused on the ecological association of E. coli 0157:H7 with cattle and production facilities (Hancock et al., Preventive Vet. Med. 35: 11–19 (1998); Hancock et al., J. Food Protection 60:462–465 (1997)). Methods to easily monitor E. coli 0157:H7 "on the farm" are important for the development and evaluation of intervention strategies to control this organism.

Metabolic and physiological differences between strains of bacteria allow for their selection and identification in current culturing methods (Doyle et al., (eds.) Food Microbiology: Fundamentals and Frontiers. American Society of Microbiology. Washington D.C. (1997); Moat and Foster, Microbial Physiology ($3^{rd}$). Wiley-Liss, New York, N.Y. (1995)). Many of these methods are based on the ability of inability of the organism to breakdown or ferment specific compounds.

Gardner et al. (Measurement Sci. Technol. 9: 120–127 (1998)) investigated the use of electronic nose technology to predict the type and growth phase of bacteria. In this study, a sensor chamber was designed that contained six metal oxide sensors chosen by their sensitivity to known products or bacterial metabolism. Two bacteria, *Staphylococcus aureus* and *Escherichia coli*, were cultured and the headspace gas of each was monitored for 12 hours in each experimental run. The gas concentration or voltage measurements were taken every eight minutes. A back-propagation neural network was used for data analysis and prediction of bacteria type. Results showed that this technology accurately classified 100% of the *S. aureus* samples, and correctly classified 92% of *E. coli* samples. An accuracy of 81% was also seen for predicting the growth phase of the bacteria. The researchers concluded that there was considerable promise for the use of electronic nose technology to rapidly detect the type and growth phase of pathogenic organisms.

Interest in the potential of using dominant odor volatiles produced by fungi for its detection, spurred an investigation of the use of gas sensors for this purpose. Keshri et al. (Letts. Appl. Microbiol. 27: 261–264 (1998)) used an electronic nose to monitor the patterns of volatile gas production to detect activity of spoilage fungi, prior to visible growth, and differentiate between species. Six different fungi were monitored and good replication was seen among the gas patterns generated by the same species. The results indicated that early detection and differentiation of fungi species was possible using electronic nose technology to monitor the patterns of gas emissions.

The potential for field use of electronic nose technology in animal production was demonstrated in a study by Lane and Wathes (J. Dairy Sci. 81: 2145–2150 (1998)). An electronic nose was used to monitor the perineal odors and predict estrus in the cow. Detectable differences in the perineal odors of cows in the midluteal phase and cows in estrous were observed. However, more research was needed to find sensors more sensitive to the specific emitted volatile compounds to enhance prediction of stage in estrous. The goal of ongoing studies is to develop an electronic nose device for use in cattle operations to enhance estrus detection.

Applications of electronic nose technology for the detection of microorganisms are based on the ability to sense the volatile products resulting from metabolism (Gardner et al., Measurement Sci. Technol. 9: 120–127 (1998); Keshri et al., Letts. Appl. Microbiol. 27: 261–264 (1998)). Current selective culturing methods for identifying *E. coli* 0157:H7 are based on differences in physiological processes or biochemical reactions. Differences in sugar fermentation are seen in *E. coli* 0157:H7 which are used to differentiate this serotype from other *E. coli* strains (Padhye and Doyle, J. Food Protection 55: 555–565 (1992)). The inability to ferment sorbitol and rhhamnose and the lack of β-glucuronidase production are known to be indicative of *E. coli* 0157:H7 (Ratnam et al., J. Clin. Microbiol. 26: 2006–2012 (1988); Sanderson et al., J. Clin. Microbiol. 33: 2616–2619 (1995); Thompson et al., J. Clin. Microbiol. 28: 2165–2168 (1990)). These biochemical characteristics and the ability to produce specific cytotoxins indicate that genetically encoded differences could exist in the cellular physiology and metabolism between pathogenic *E. coli* 0157:H7 and other strains of *E. coli*.

Enterobacteriaceae, including *E. coli*, carry out mixed acid fermentation resulting in the end product formation of ethanol, acetate, succinate, formate, molecular hydrogen, and carbon dioxide (Atlas, Principles of Microbiology. Mosby Year Book, Inc. St. Louis, Mo. (1995)). In this study, it was hypothesized that an electronic nose could be used to detect the volatile compounds produced by various *E. coli* strains and differentiate serotype 0157:H7 based on a unique pattern of gas emissions. An instrument was designed that contained biosensors sensitive to known end products of microbial metabolism: ammonia and nitrogenous compounds; methane, ethanol, and isobutane; and hydrogen sulfide (Atlas, Principles of Microbiology. Mosby Year Book, Inc. St. Louis, Mo. (1995); Gardner et al., Measurement Sci. Technol. 9: 120–127 (1998); Moat and Foster, Microbial Physiology ($3^{rd}$) Wiley-Liss, New York, N.Y.

(1995)). Selecting several sensors reactive to various compounds was important for later studies involving other types of bacteria. Based on the detectable differences observed between the gas patterns of generic *E. coli* and *E. coli* 0157:H7 and further evaluation of gas sensors it may be possible to identify a single gas sensor capable of demonstrating metabolic differences between strains of bacteria (Younts et al., J. Animal Sci. 77 (Suppl. 1): 129 (1999)).

In the midst of current efforts to reduce human exposure to foodborne pathogens, animal production has come under scrutiny as a potential source of these organisms. The government, scientific community, and producers are aware of a need to study the epidemiology and control of pathogens "on the farm". Electronic nose technology has the potential to enhance efforts addressing pre-harvest food safety concerns involving *E. coli* 0157:H7, by providing a convenient, economically feasible, and less labor intensive tool for identifying carrier cattle or other environmental sources/reservoirs of the organism. Advantages of an electronic nose as a diagnostic tool include the identification of live bacteria and monitoring of their growth, no requirement for reagents, and the capability of being automated.

In the present invention, differences in the breakdown products produced by certain bacteria are detectable by monitoring their gas emissions during growth. Volatile compounds can be monitored using artificial olfactory technology based on gas sensors (Bartlett et al., Food Technol. 51: 44–48 (1997); Gardner et al., Measurement Sci. Technol. 9: 120–127 (1998)). The objective of this Example was to develop and evaluate a gas sensor based instrument capable of detecting and differentiating *E. coli* 0157:H7 from non-0157:H7 *E. coli* isolates through gas emissions in laboratory cultures.

Rapid and economical detection of human pathogens in animal and food production systems would enhance food safety efforts. The objective of this research was to develop a gas sensor based instrument, coupled with an artificial neural network (ANN), which is capable of differentiating the human pathogen *E. coli* 0157:H7 from non-0157:H7 *E. coli* isolates. The production of gases from eight laboratory isolates and 20 field isolates of *E. coli* were monitored during growth in laboratory conditions, and a unique gas signature for each isolate was generated. An ANN was used to analyze the gas signatures, and classify the bacteria as 0157:H7 or non-0157:H7 *E. coli*. Detectable differences were observed between the gas signatures of the *E. coli* 0157:H7 and non-0157:H7 isolates and the ANN classified the isolates with a high degree of accuracy. Based on this work, gas sensor based technology has promise as a diagnostic tool for pathogen detection on pre-harvest and post-harvest food safety.

An apparatus was assembled comprising the gas sensing component of the present invention for collecting, monitoring, and recording the gas emissions from various growing *E. coli* cultures. Several considerations were addressed in designing the instrument. The first consideration was the need for a culturing system or a way to grow and maintain bacteria within the apparatus. The next consideration was a method to capture or collect the gas emissions in a confined space. Detection of the presence of the gas and identification of the type of volatile compounds being emitted must be available. The final consideration was a means of recording the data or gas measurements automatically. Construction involved assembly of a chamber and interconnections between chamber and data collection system (computer).

A chamber was designed to sit on a dry-block heater, which (FIG. 1A) could hold a culture vial and maintain a temperature supportive of bacterial culture growth. The chamber was rectangular in shape, approximately 10 cm in height×12.5 cm in length×10 cm in width. The chamber was constructed out of PLEXIGLASS and sealed to capture or contain the volatile compounds and prevent permeation of odors from the outside environment into the sensor chamber. Gas sensors, for detecting the presence of specific compounds, were mounted in the ceiling of the chamber, directly above the opening of the culture vial in the dry block heater. The gas sensors were linked to a circuit board placed on the top of the chamber, which was connected to the power source.

Metal oxide gas sensors were acquired from a proprietary vendor (Figaro USA, Inc., Glenview, Ill.) to detect, measure, and monitor the volatile gases released from the bacterial cultures. The following description of the sensor operating principle was obtained from the "General Information for TGS Sensors" (Figaro USA, 1996). In these sensors, a chemical reaction occurs between the metal oxide, usually $SnO_2$, in the sensor and the volatile gas it is designed to detect. An electrical current flows between connected micro crystals of metal oxide within the sensor. The sensing material, metal oxide, has a negative charge on the surface and absorbs oxygen, which accepts electrons, leading to a positive charge. The resulting surface potential can act as a potential barrier against electron transfer, increasing the electrical resistance within the sensor. The volatile compound for which the sensor is specifically designed to detect serves as a reducing gas. When this compound is present, the negatively charged oxygen density on the surface between the metal oxide crystals is decreased. The height of the barrier against electron transfer is reduced and there is a decrease in sensor resistance. The amount of decrease in sensor resistance is proportional to gas concentration; the higher the gas concentration the greater the increase in electron flow. The decrease in sensor resistance, or increase in electrical conductivity, is converted to a change in voltage by the circuit board. The voltage readings are fed to the data acquisition board and transferred to the computer for continuous plotting.

The sensors employed in the apparatus were chosen based on their ability to detect volatile metabolites known to be produced from bacterial metabolism (Moat and Foster, Microbial Physiology. Wiley-Liss. New York, N.Y. (1995)). Four gas sensors were used, specific for the following: amines (sensitivity of 30 ppm ammonia in air, Figaro TGS 826), alcohol (50–5,000 ppm, Figaro TGS 822), air contaminants (1–10 ppm, Figaro TGS 800), and hydrogen sulfide (5 ppm, Figaro TGS 825). The amine sensor is very sensitive to ammonia and amine compounds; the alcohol sensor to methane, iso-butane, and ethanol; and the air contaminants sensor to similar alcohol compounds at lower concentration (Figaro USA, 1996). Two additional sensors were used to monitor the ambient temperature (Figaro D Thermistor) and relative humidity (Figaro NHU-3) within the apparatus. Monitoring the stability of temperature and humidity is critical due to their effects on the sensitivity of the sensors. A change in temperature or relative humidity can affect the rate of the chemical reaction as it occurs within each sensor (Figaro USA, 1996). FIG. 1A shows a diagram of the sensor chamber and sampling platform for the apparatus.

A data acquisition module (model 232SDA12, B & B Electronics, Ottawa, Ill.) was used to convert the output from the gas sensors to digital output for recording by a computer containing software for data collection. This module was positioned on the chamber and was directly connected to a computer housing the software for data collection. FIG. 2A shows a diagram of the data acquisition module for converting the output from the sensors to digital output for recording by a computer. Ports for tubing were drilled into either side of the chamber; on one side the tubing was connected to a vacuum pump and the other side had tubing open to the outside. These tubes were used to evacuate and draw air through the chamber between experiments. FIGS. 1 and 1C show the overall system and FIG. 2 shows a diagram of the gas sensors which are placed in the chamber ceiling.

A data acquisition software program (MeterBOSS, Teramar Group, Inc., El Paso, Tex.) was used to collect and record each sensor response. This program controlled the rate of gas sampling and plotted the voltage readings generating a pattern or gas signature during the length of each experimental run. The gas patterns could then be analyzed for differences and similarities for classification of the bacterial strains.

An artificial neural network (ANN) was chosen for the analysis and interpretation of the gas signatures. An ANN is an information processing system that is patterned after the way the brain and nervous system process information (Tuang et al., FEMS Microbiol. Letts. 177: 249–256 (1999)). For this investigation, we employed a back-propagation neural network (BPN) algorithm (BrainMaker, California Scientific Software, 1998). The standardized data from each experiment, the gas signature data points, serves as the input vector. The desired output vector is the classification of the organism, "0" for non-0157:H7 E. coli and "1" for E. coli 0157:H7. Training is accomplished by using a standardized data set (standard gas signatures) and associating the input or gas signature with the desired output or classification. The program compares the data and computes network output with the desired output until an acceptable level of recognition is achieved. Another set of data is used for testing the predictive capability of the trained BPN.

In testing, the BPN is exposed to the input vectors not labeled with the bacterial type or desired output classification. Evaluation of the training is based on the ability of the BPN to recognize and accurately classify the bacteria type from the input gas signature. The efficacy of the apparatus for differentiating E. coli 0157:H7 from non-0157:H7 isolates is determined by the ability of the BPN to distinguish between gas signatures and correctly classify the bacterial type.

Characterized strains of E. coli, four isolates of E. coli 0157:H7 and four non-0157:H7 serotypes, from various sources were obtained for use in the investigation (Table 1). Two of the isolates were obtained from Michigan State University and the remaining six isolates were obtained from The Ohio State University.

TABLE 1

Serotypes and Sources of E. coli Isolates

| Isolate | Serotype | Source |
| --- | --- | --- |
| Lab Non-0157:H7 | Non-0157:H7 | Veterinary Medical Center, Michigan State University |
| E47411/0 | 05:H- | Dr. Qijing Zang, The Ohio State University |
| 80-2572 | 0157:H13 | Dr. Qijing Zang, The Ohio State University |
| SD89-3143 | 0111:NM | Dr. Qijing Zang, The Ohio State University |
| Lab 0157:H7 | 0157:H7 | Veterinary Medical Center, Michigan State University |
| ATCC 43895 | 0157:H7 | Dr. Qijing Zang, The Ohio State University |
| CDC B038-MS1/0 | 0157:H7 | Dr. Qijing Zang, The Ohio State University |
| E29962 | 0157:H7 | Dr. Qijing Zang, The Ohio State University |

These isolates were independently verified as E. coli 0157:H7 or non-0157:H7 E. coli by the Bacteriology Laboratory at the Veterinary Diagnostic Center, University of Nebraska, Lincoln, Nebr. For verification as E. coli 0157:H7, the isolates were subject to PCR for the presence of the eae gene, Shiga toxin (STX) structural gene and the O antigen biosynthesis (rfb) loci. All experiments were performed in a certified Biological Safety Level II laboratory.

Two types of bacterial culture media, Brain Heart Infusion Broth (BHI) and Nutrient Broth (Difco Laboratories, Detroit, Mich.), were evaluated for their use for growing bacteria that would cause the formation of detectable volatile compounds. Two isolates of E. coli, one 0157:H7 serotype and one non-1057:H7 serotype, were used for the comparison. Both isolates were grown individually in each media. For each experiment, 10 ml of the media was placed in a sterile 14 ml polystyrene vial then inoculated with 100 colony forming units (CFUs) of one of the isolates. The vial was centrally placed in the dry block heater, maintained at 37±0.2° C., and monitored over time within the chamber. The gas readings were collected at a one minute sampling rate, plotted over 20 hours and a gas signature generated for each experiment.

To determine if there were differences in the gas signatures based on the presence of different concentrations of the same bacteria, a study was conducted using different initial concentrations of bacteria. The concentrations of the bacterial stock cultures were determined by serial dilution and viable plate counts. Bacterial concentrations of $10^2$, $10^3$, $10^4$, $10^5$, $10^6$, and $10^7$ per ml, were used for the initial inoculum and monitored over time to determine the occurrence of the initial voltage increase. For each experiment, the desired concentration of bacteria was introduced into 10 ml of nutrient broth and the vial was centrally placed in the dry block heater, maintained at 37±0.20° C., within the chamber. Both E. coli 0157:H7 and non-0157:H7 E. coli isolates were assayed at the different inoculum concentrations to determine the time each concentration required to reach the initial voltage increase. Gas patterns or signatures were identified starting at the initial voltage increase and ending with the voltage readings decreased to levels equivalent or less than those prior to the initial increase.

The dry block heater and uninoculated media were monitored over time to determine if detectable volatile compounds, not associated with bacterial growth, were being released. The chamber was placed over the dry block heater with nothing in it. The sensor readings were taken at a one minute sampling rate for 20 hours. For monitoring the volatile compounds from the media, 10 ml of nutrient broth was placed in a sterile 14 ml polystyrene vial. The vial was placed in the dry block heater at 37±0.2° C. with the chamber in place and monitored at a one minute sampling rate for twenty hours.

The growth activity of the microorganisms in nutrient broth within the apparatus was monitored to investigate the relationship between bacterial growth and gas emissions. All eight isolates of E. coli were used in this experiment. Cultures were grown and maintained in nutrient broth to establish a stock culture of each isolate. There were two separate experimental runs on each isolate, making a set of 16 growth curves. For each isolate, a predetermined concentration of $10^5$ CFU/ml, was introduced to a sterile polystyrene vial containing 10 ml of nutrient broth. The vial was then placed in the dry block heater within the chamber. At 2-hour intervals the chamber was lifted and 100 µl of the sample culture was drawn out of the vial using a pipette over a 16 hour period. The 100 µl samples were serially diluted and viable plate counts were performed. The results from the plate counts were plotted over the 16 hour time period to establish standard growth curves for each isolate.

Figure 3:
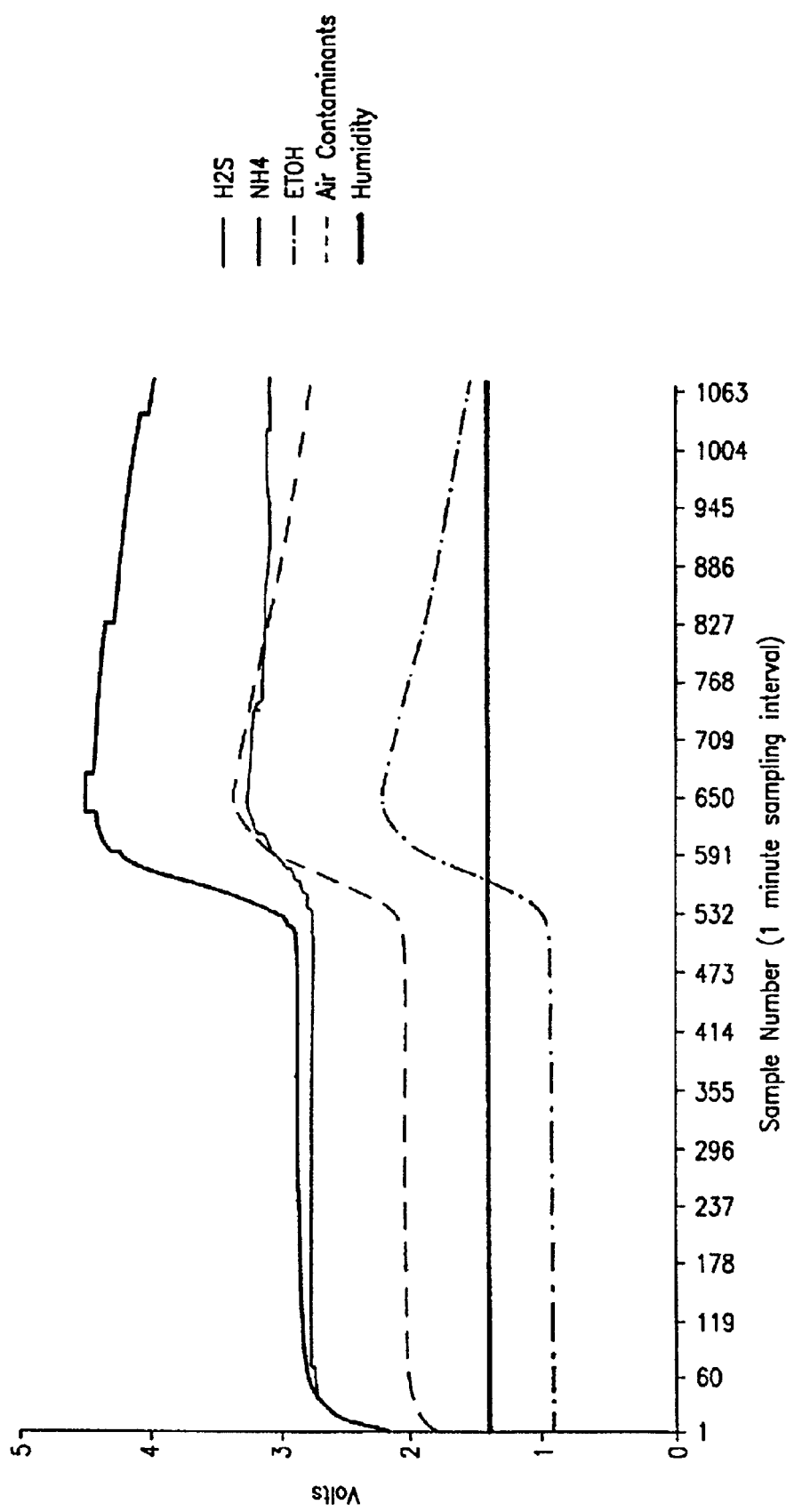
FIG. 3 is a graph of a representative gas signature generated by non-0157:H7 E. coli in BHI broth.
Figure 4:
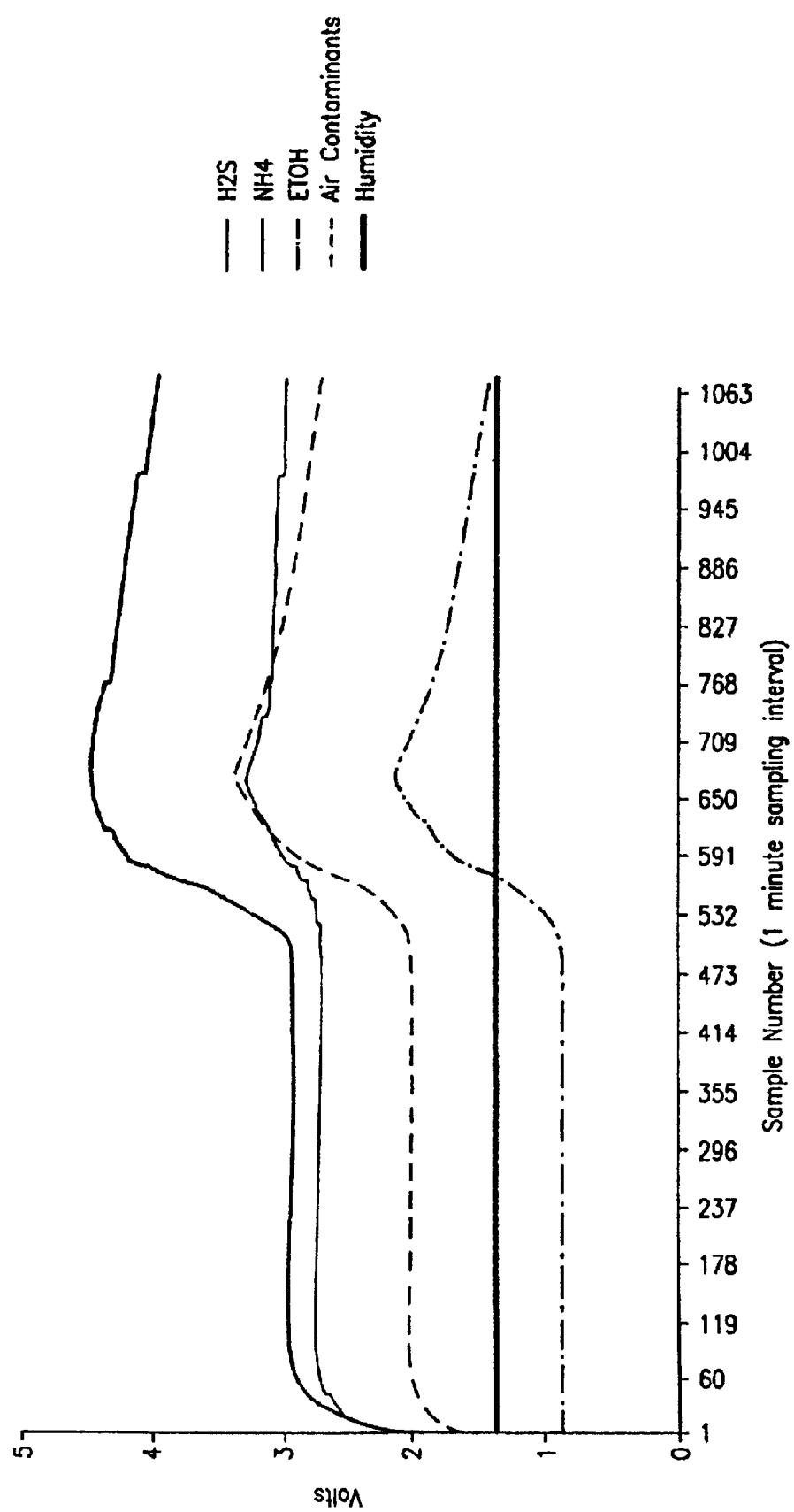
FIG. 4 is a graph of a representative gas signature generated by E. coli 0157:H7 in BHI broth.

The results of the experiments in BHI media demonstrated that gas emissions could be detected from the growing cultures. A distinct increase in voltage readings was seen over time for each of the gas sensors. In the BHI broth, the voltage readings dramatically increased initially, peaked, then tapered off. No obvious differences were observed between the gas emissions from the 0157:H7 and the non-0157:H7 isolates. FIGS. 3 and 4 show representative gas signatures for E. coli 0157:H7 and non-0157:H7 E. coli in BHI, which visually were similar for both bacteria isolates.

Figure 5:
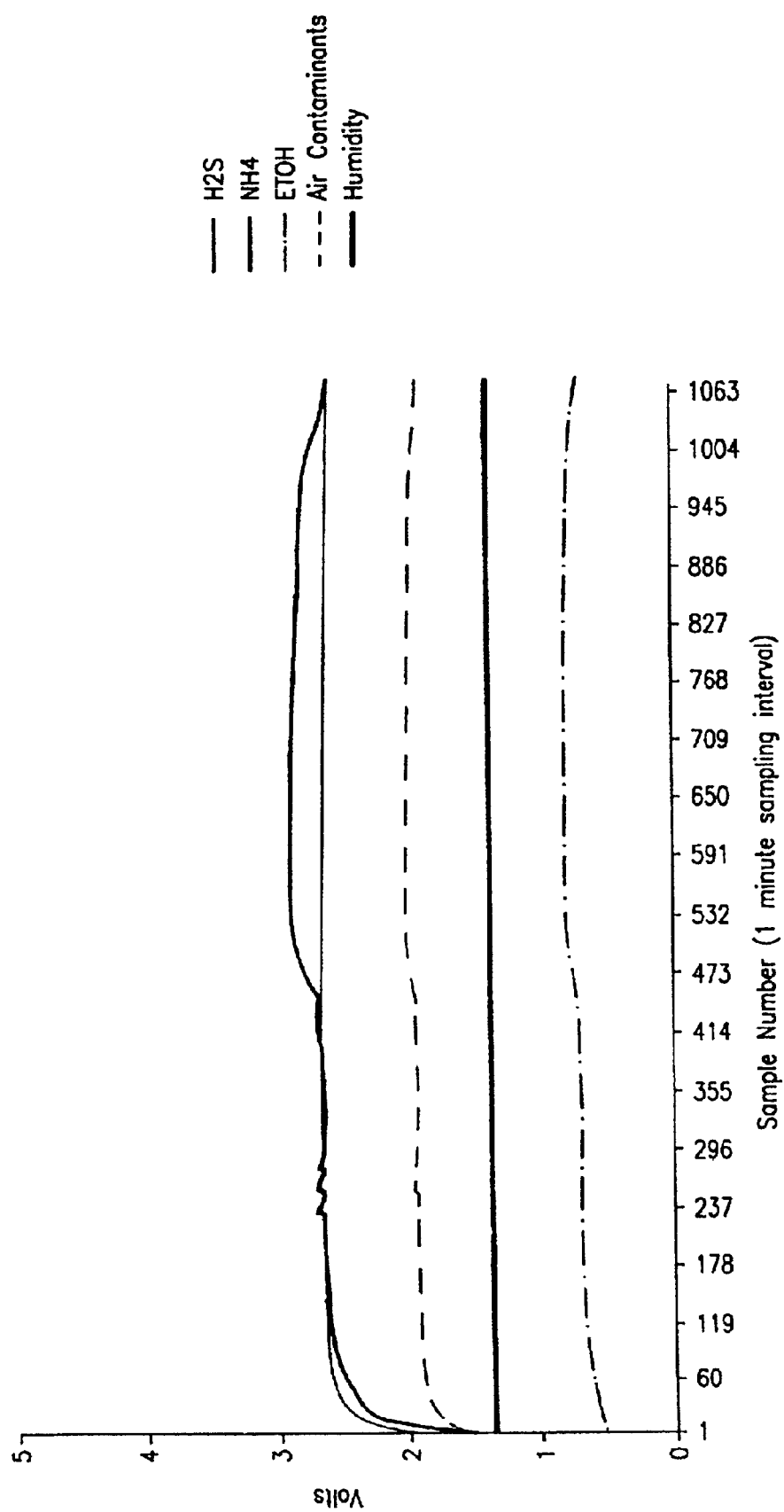
FIG. 5 is a graph of a representative gas signature generated by E. coli 0157:H7 in nutrient broth.
Figure 6:
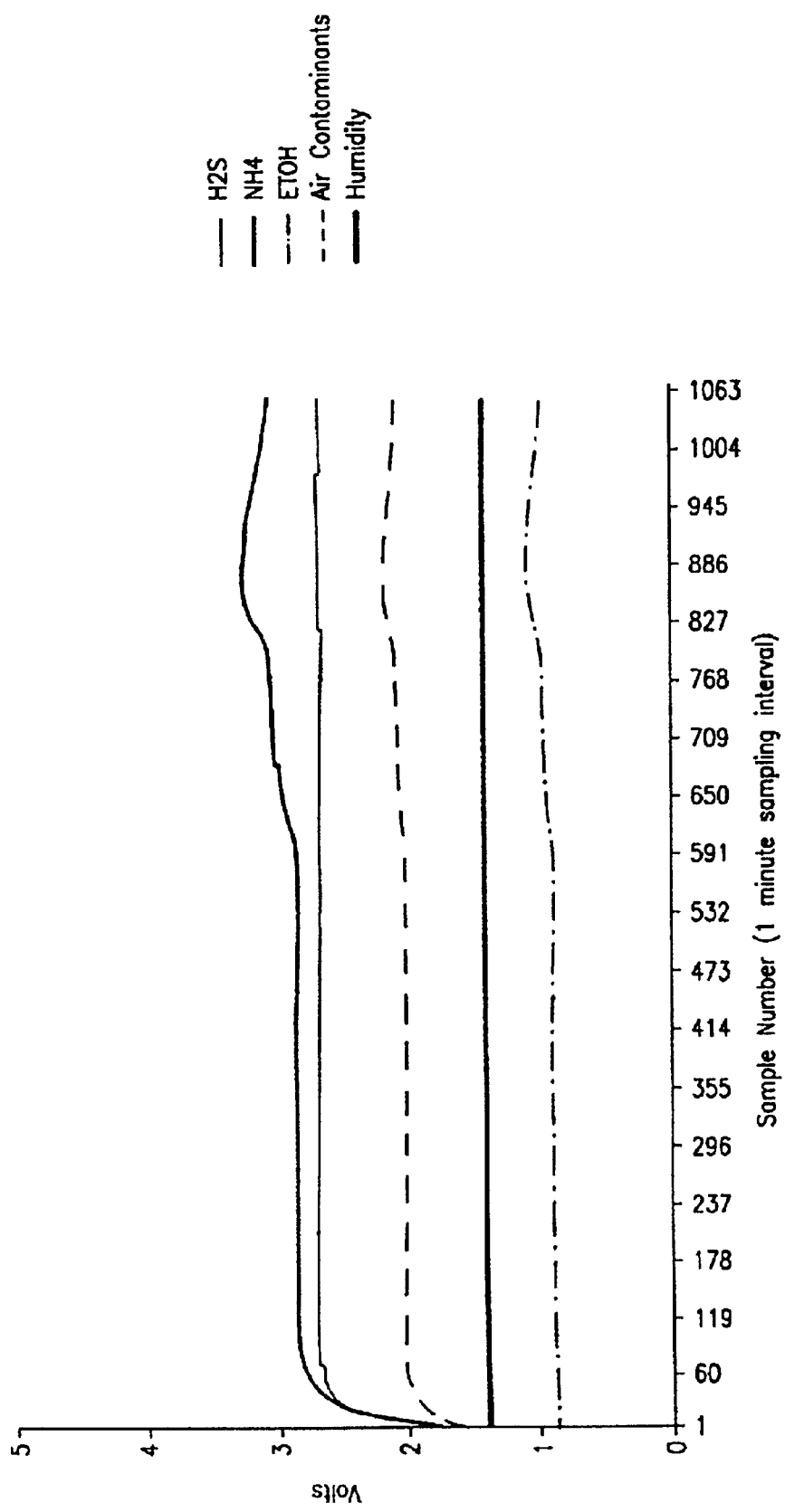
FIG. 6 is a graph of a representative gas signature generated by non-0157:H7 E. coli in nutrient broth.

When the bacteria isolates were grown in nutrient broth, the initial increase in voltage in the nutrient broth was not as dramatic as that observed in the BHI media. However, unlike the gas signatures observed when grown in BHI media, visually detectable differences were observed between the gas signatures of the E. coli 0157:H7 isolate and the non-0157:H7 isolate grown in nutrient broth. When the E. coli 0157:H7 isolate was grown in nutrient broth, the gas signature that was observed showed an initial increase and a period of stabilization followed by a gradual decrease in the voltage readings (FIG. 5). When the non-0157:H7 E. coli was grown in nutrient broth, the gas signature that was observed showed a binary increase in voltage followed again by a period of tapering off (FIG. 6). Excellent reproducibility was seen in the pattern of gas emissions between the replicate experiments for each isolate. Eased on these observations, nutrient broth was used as the growth media for further experiments.

Figure 7:
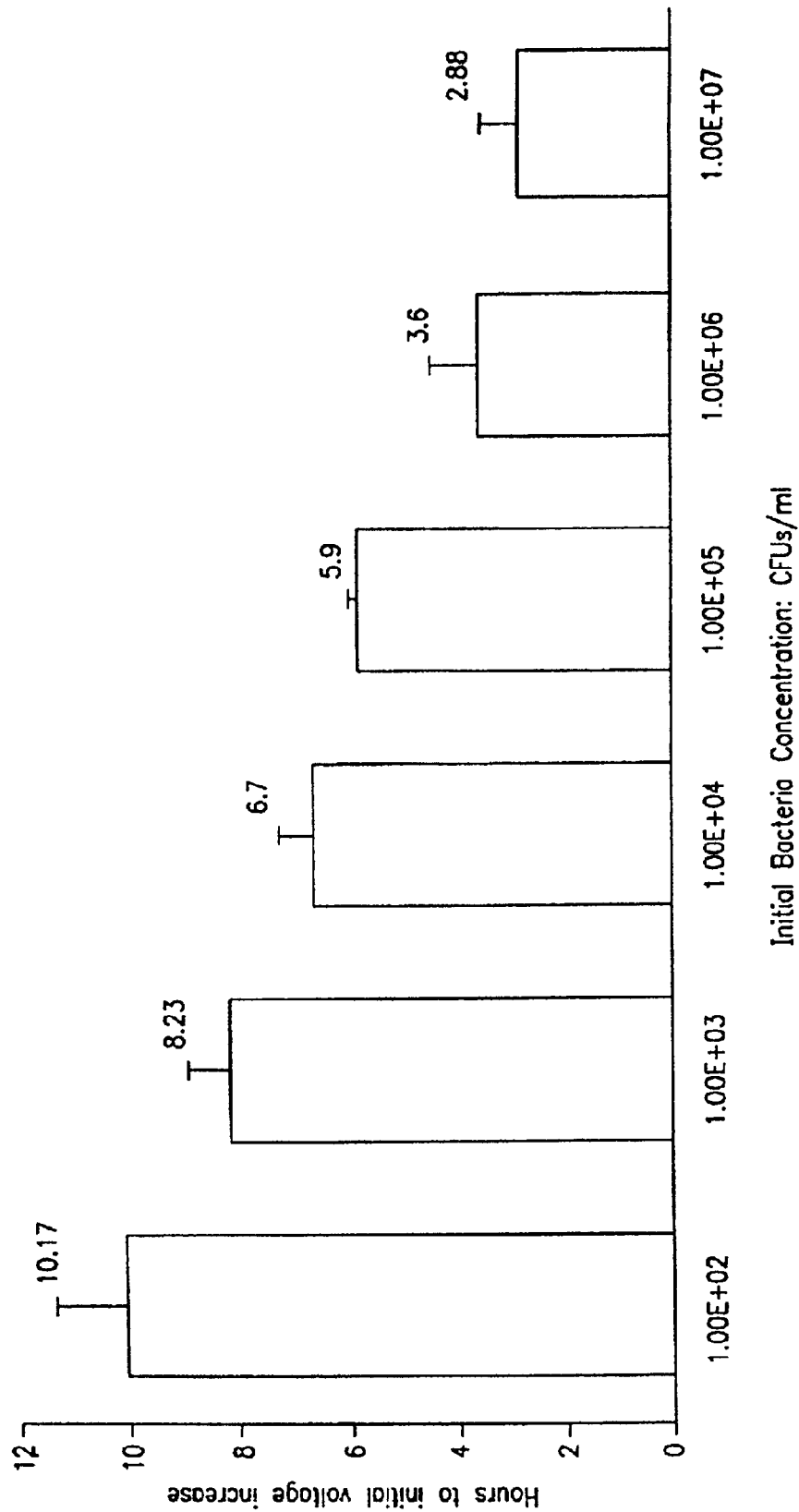
FIG. 7 is a graph showing an average time in hours (+/− standard deviation) for initial increase in gas concentration to occur, as measured by voltage increase in gas sensors, at different initial bacteria concentrations.

The presence of a detectable level of gas concentration was reached sooner with a higher initial concentration of bacteria. The gas patterns for the same bacteria were similar in shape over the different concentrations. However, the initial voltage change occurred later for each decrease in initial bacteria concentration. FIG. 7 shows the initial bacteria concentration and the average time in hours required for the initial voltage increase to be observed. To establish repeatable standard gas signatures for E. coli 0157:H7 and non-0157:H7 E. coli isolates a standard initial concentration of $10^5$ colony forming units (CFU's) per ml and a monitoring time of 16 hours was used for further experiments. A concentration of $10^5$ CFU's/ml was chosen because it optimized the length of time in which a consistent gas signature could be obtained.

Figure 8:
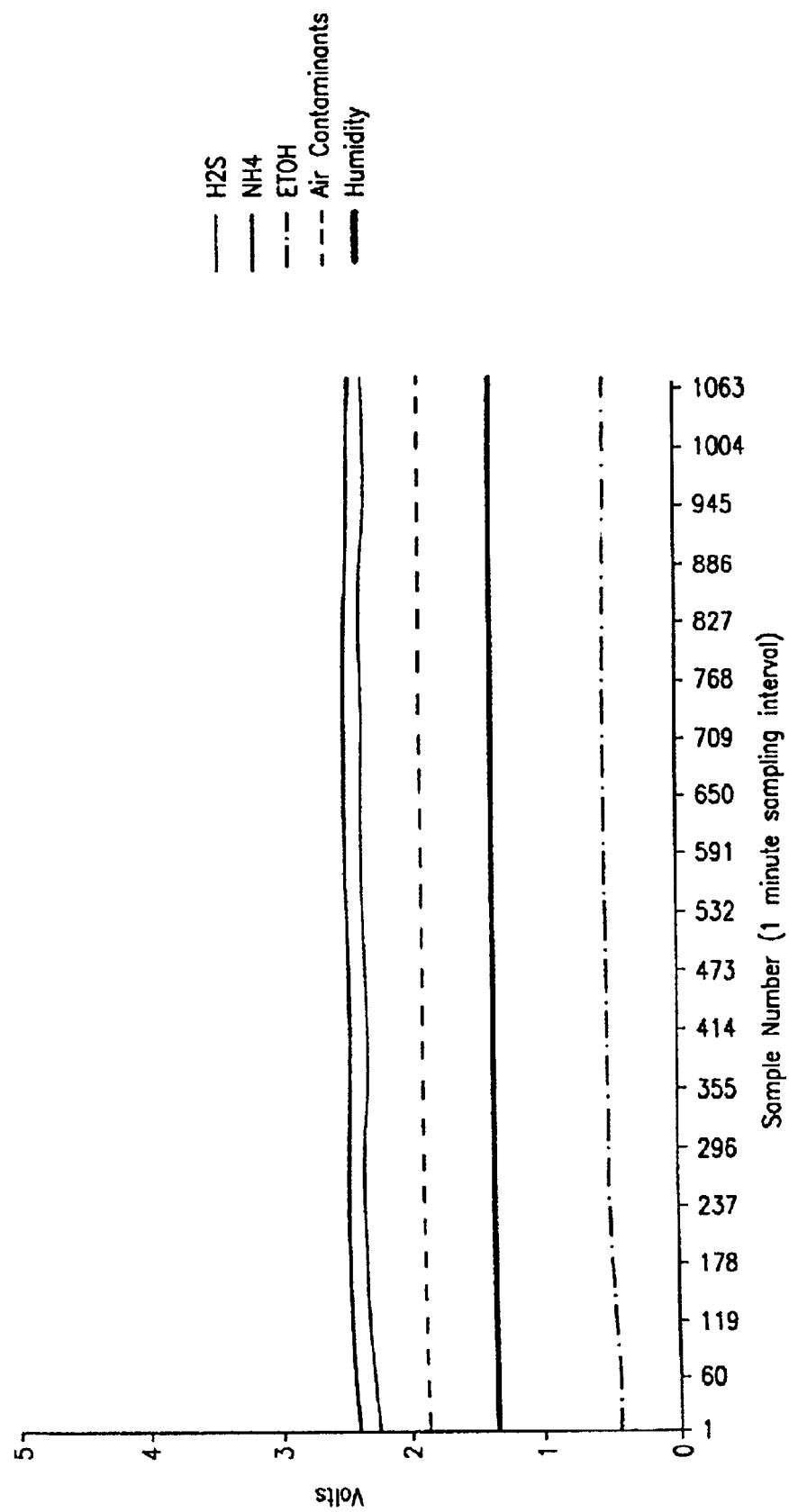
FIG. 8 is a graph of a control gas signature from monitoring dry block heater.
Figure 9:
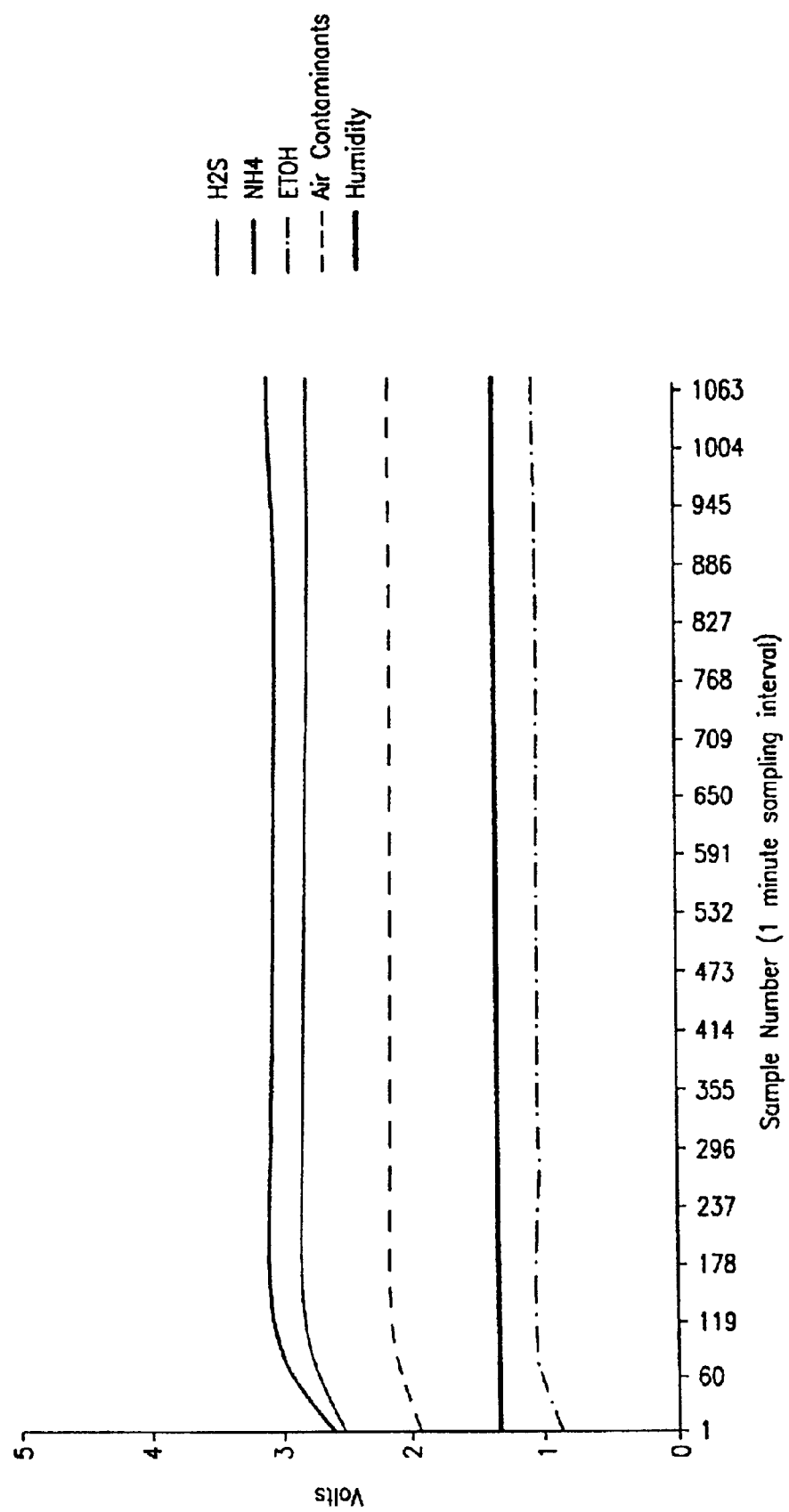
FIG. 9 is a graph of control gas signature from monitoring nutrient broth.

No voltage change was observed when the dry block heater was monitored for release of volatile compounds over time (FIG. 8). Monitoring of uninoculated nutrient broth initially showed a slight increase in voltage over time (FIG. 9). This increase was expected as the media was warmed to 37° in the heater and volatile compounds could be detected. The decrease in sensor resistance was even and eventually stabilized indicating that volatiles from the media did not impact the gas signatures seen with the bacteria cultures.

Figure 10:
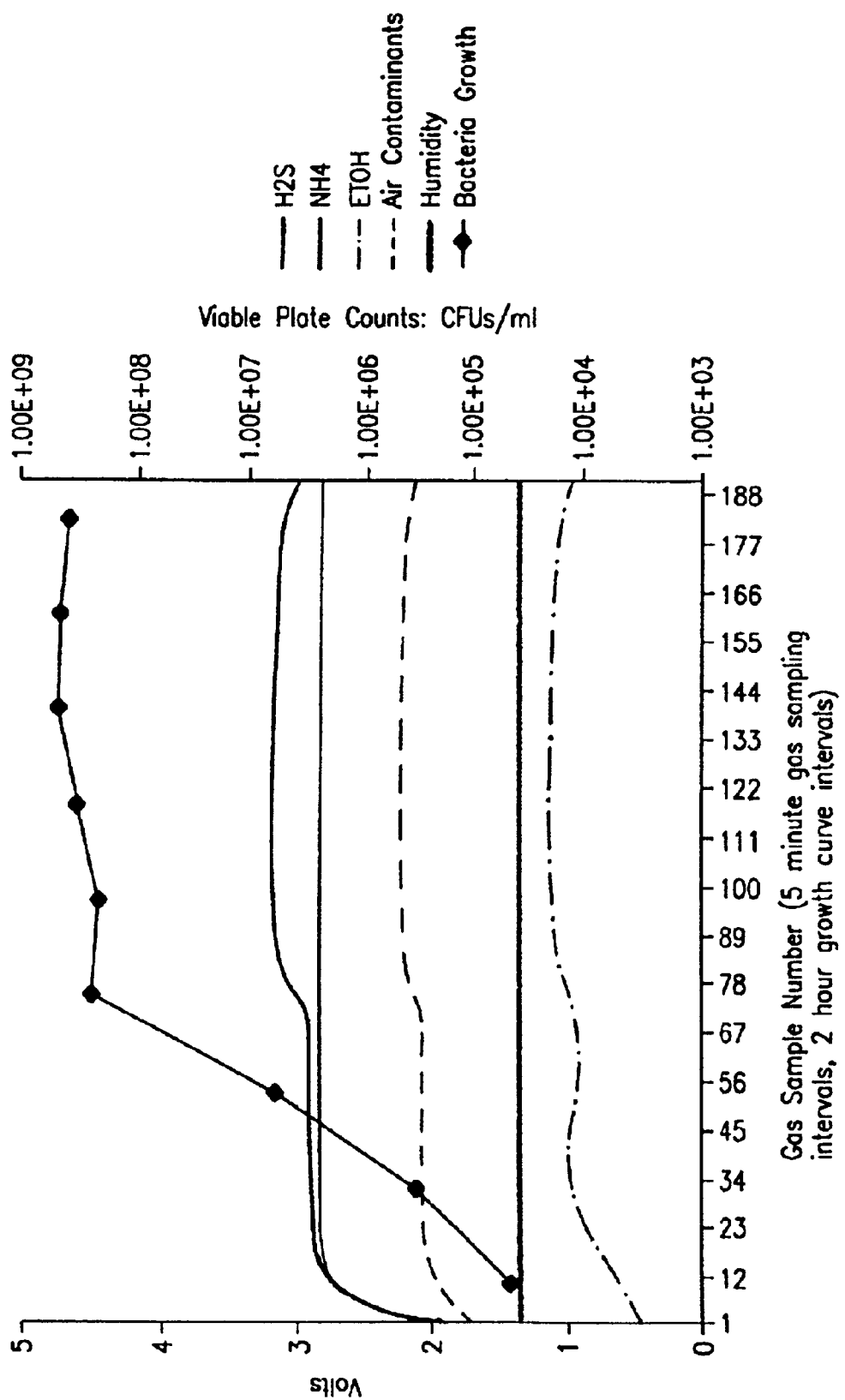
FIG. 10 is a graph of a representative growth curve for E. coli 0157:H7 plotted against a typical gas signature.
Figure 11:
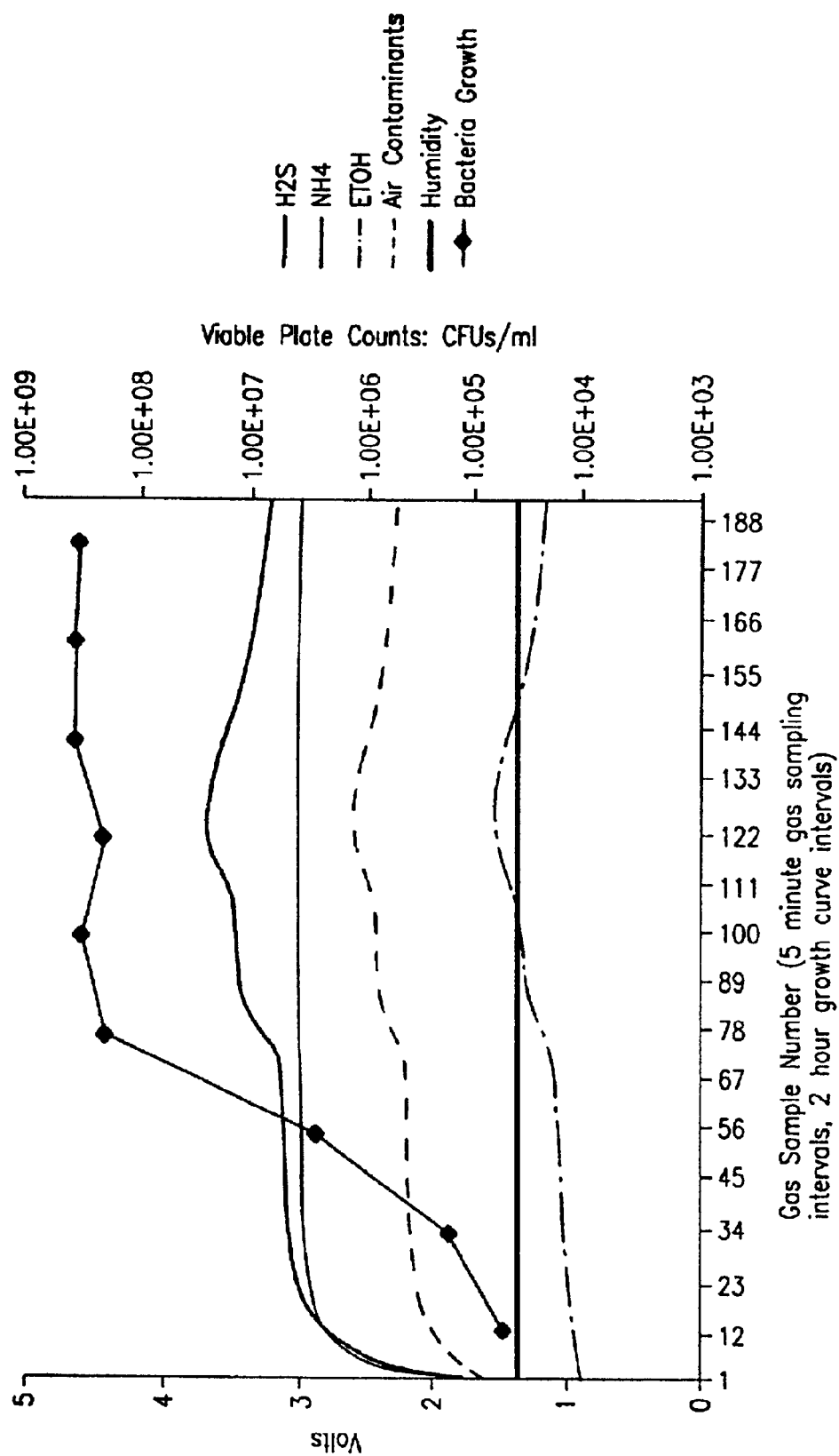
FIG. 11 is a graph of a representative growth curve for non-0157:H7 E. coli plotted against a typical gas signature.

Representative growth curves plotted against gas signatures for E. coli 0157:H7 and for non-0157:H7 E. coli are shown in FIGS. 10 and 11, respectively. The Figures demonstrate the relationship between the lag, log, and stationary phases of microbial growth and the occurrence of gas emissions within the sensing system. It was repeatedly observed that the initial voltage change or detection of gases occurred during the mid to late log phase of bacterial growth. It was also observed that the voltage stabilized during the stationary growth phase.

The results demonstrate that the apparatus is useful for investigating the potential of identifying E. coli 0157:H7 based on the pattern of volatile gases released during growth. The apparatus was capable of detecting the gas emissions from growing E. coli cultures. Differences in the gas patterns were seen based on the media and bacteria concentration employed. The variations in gas patterns based on the type of media used are most likely due to differences n the nutrient composition of the media that resulted in different metabolic breakdown products. No obvious visual differences in the gas patterns produced by E. coli 0157:H7 and non-0157:H7 isolates were observed when cultured in BHI broth. However, recognizable differences were observed in the gas patterns when cultured in nutrient broth. This suggests that some component of nutrient broth is metabolized differently by the two types of bacteria, resulting in different patterns of gas production. The amount of time that it took to first detect gas production was dependent on the initial bacterial concentration introduced into the test system. Initial detection of gas occurred faster when a higher concentration of bacteria was used. This suggests that a critical mass of bacteria must be present to produce detectable levels of the gases. Control testing established that the media and sensor apparatus do not give off volatile gases which may be interpreted as bacterial gas production.

Preliminary observations allowed for the defining of appropriate protocols for standard experiments to be used in investigating the use of the apparatus for differentiating E. coli 0157:H7 from non-0157:H7 E. coli. Based on these results, standard experiment protocols were developed to include using nutrient broth as the growth medium, starting with an initial bacteria concentration of $10^5$ CFUs/ml, monitoring the gas emissions for a period of 16 hours, and analyzing the gas signatures using an ANN trained with standardized data sets.

EXAMPLE 2

This example illustrates differentiation of E. coli 0157:H7 from non-0157:H7 E. coli serotypes using the gas sensor component of the present invention.

Characterized strains of E. coli, four isolates of E. coli 0157:H7 and four non-0157:H7 serotypes, as shown in Example 1 were used. Four standardized experimental runs were performed on each isolate making a total set of 32 experimental runs or gas signatures. First, 10 ml of nutrient broth was placed into a sterile 14 ml polystyrene vial. A set concentration of bacteria, $10^5$ CFU/ml, was introduced into the vial from culture stocks of the bacteria. The vial was centrally placed in a 37° C. dry-block heater and grown within the chamber. Each experiment ran for 16 hours with gas sampling every five minutes. The gas readings or voltage measurements were continuously plotted, generating a gas signature. Preliminary studies identified the initial cell concentration and time interval most appropriate for experimental standardization. The chamber used is as described in Example 1.

Each of the four experimental runs on every *E. coli* isolate generated a standardized gas signature for that isolate, providing four gas signatures for each isolate. Data set "1" consisted of the signatures from the first experimental run on each isolate. Data sets "2," "3," and "4" were made up of gas signatures from each subsequent experimental run. The data was divided equally into training and testing sets for the neural network analysis. In the training process, the ANN was configured for data classification. The data sets were used in different combinations as part of the training and testing of the ANN. For example, data sets 1 and 2 were used as the training set and sets 3 and 4 were used as the testing set for one train-test scenario. The next scenario used data sets 3 and 4 for training and 1 and 2 for testing. The third scenario involved data sets 1 and 3 for training and sets 2 and 4 for testing. There were a total of six scenarios for each responding sensor type as shown in Table 4.

TABLE 4

Scenarios for Training and Testing the ANN

| Scenario | Training Set | Testing Set |
|---|---|---|
| 1 | 1 & 2 | 3 & 4 |
| 2 | 3 & 4 | 1 & 2 |
| 3 | 1 & 3 | 2 & 4 |
| 4 | 2 & 4 | 1 & 3 |
| 5 | 1 & 4 | 2 & 3 |
| 6 | 2 & 3 | 1 & 4 |

The recognition/classification by the ANN is based on the shape of the gas pattern, not specific time-data points. Although the shapes of the gas signatures are similar there is fluctuation in the voltage readings at a specific time due to differences in gas concentration intensity. This fluctuation in voltage level affects the ability of the ANN to recognize unseen patterns and accurately classify them. By dividing the data into testing and training sets, the specific patterns used to "test" the ANN analysis have not been seen before.

The ANN is programmed to recognize a gas pattern shape based on the training set. When tested, the ANN calculates the probability that the previously unseen patterns in the testing set are indicative of a desired classification. For example, the ANN compares each gas signature in the testing set with the patterns it was "trained" to recognize from the training set. The resulting output from the ANN is the probability for each testing pattern, or isolate gas signature, that it is *E. coli* 0157:H7 or non-0157:H7 *E. coli*. For each training and testing scenario, the previous training/testing scenario was deleted and the ANN was retrained and tested. The sensitivity and specificity of detecting *E. coli* 0157:H7 for each scenario was calculated and then averaged together.

The apparatus was evaluated for its value as a screening test for *E. coli* 0157:H7. Based on the differences in the gas patterns of the two *E. coli* groups, 0157:H7 and non-0157:H7, the ANN generated probabilities that individual gas signatures were representative of *E. coli* 0157:H7 or not. Based on the correctness of the classification from the probabilities, the sensitivity and specificity of the apparatus were calculated (Smith, In Veterinary Clinical Epidemiology: A Problem Oriented Approach. CRC Press, Ann Arbor, Mich. (1995), pp 31–52).

Figure 12:
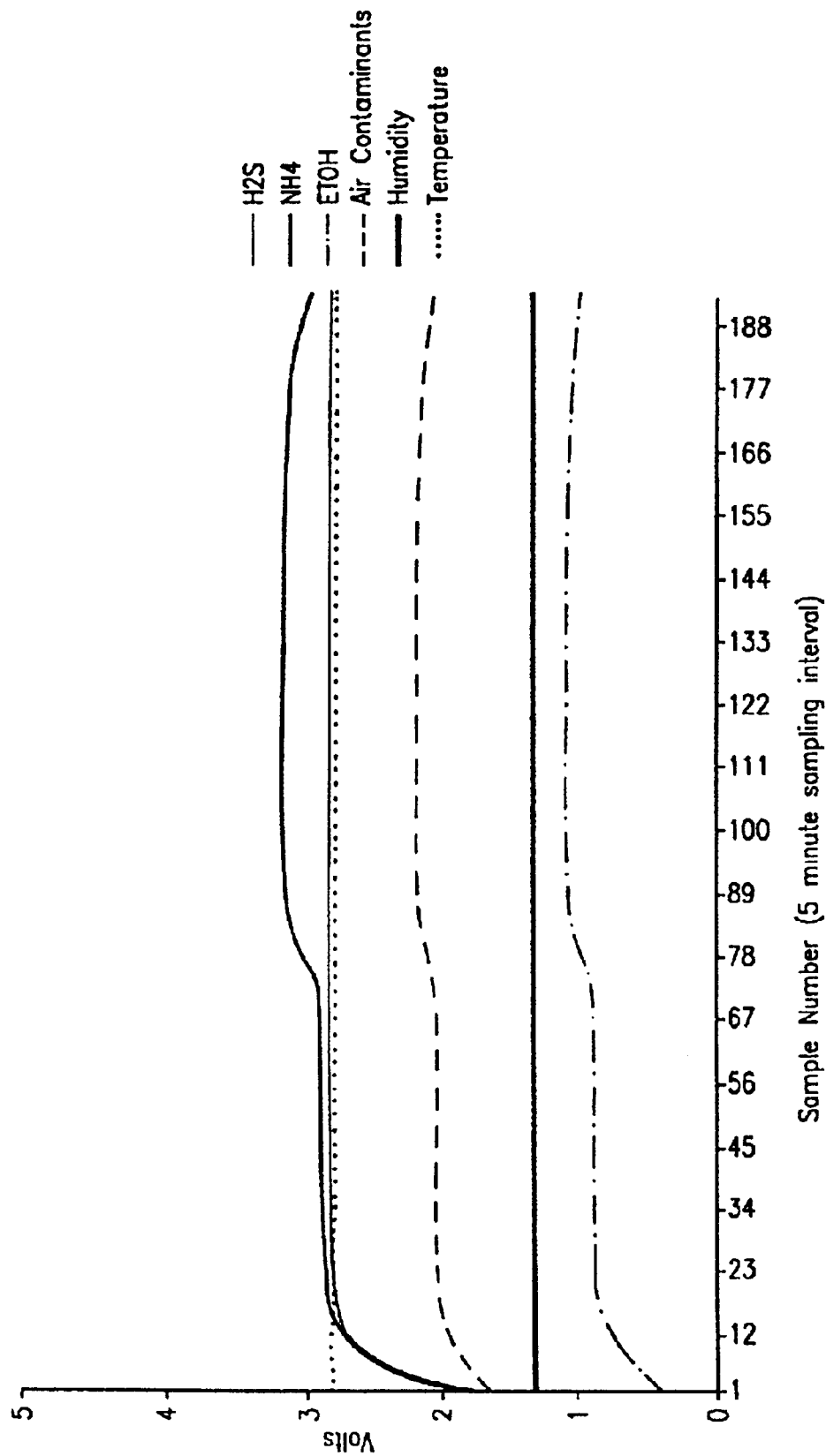
FIG. 12 is a graph of a representative gas signature generated by E. coli 0157:H7.
Figure 13:
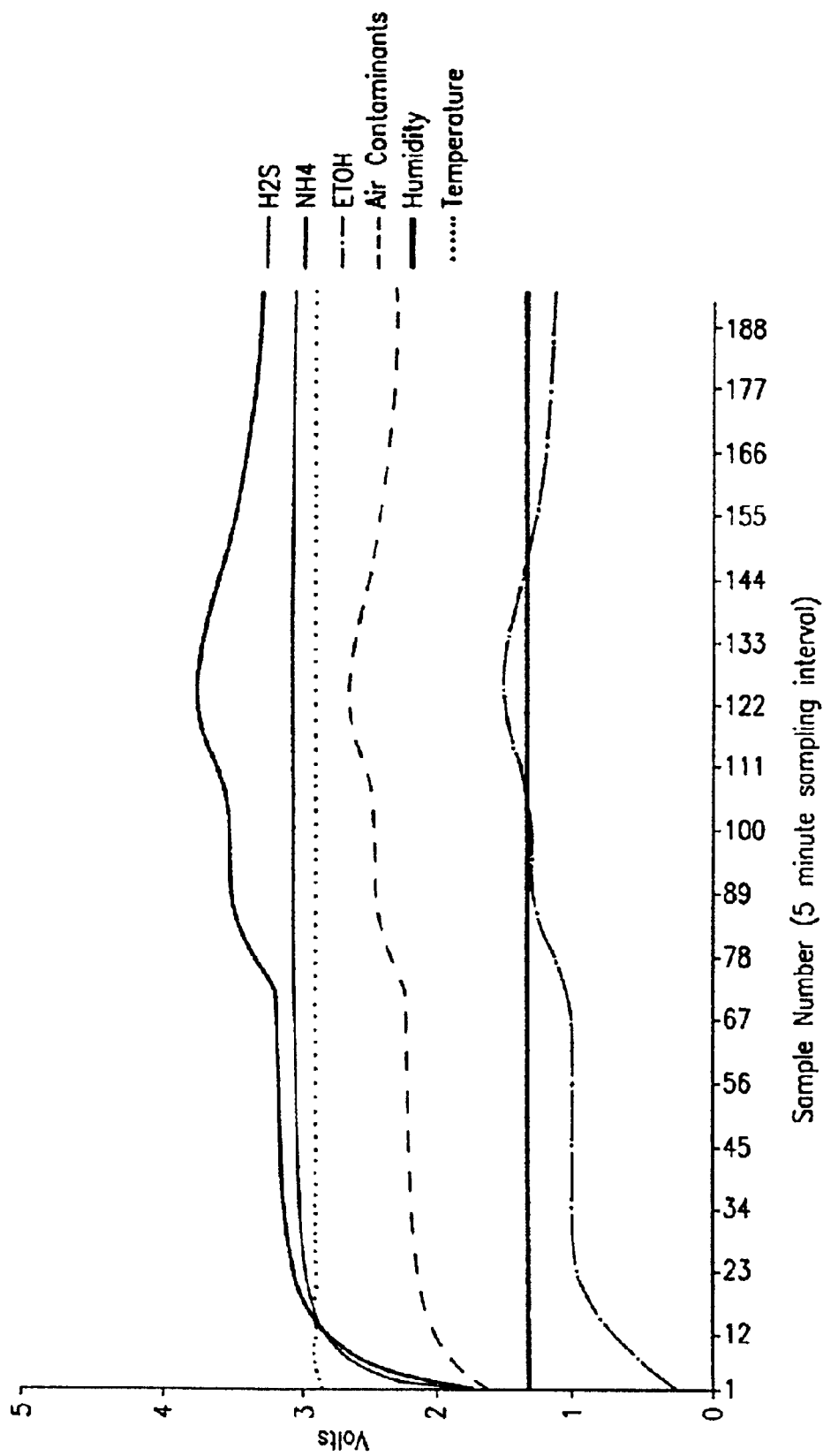
FIG. 13 is a graph of representative gas signature generated by non-0157:H7 E. coli.

Detectable differences were observed between the gas signatures of the *E. coli* 0157:H7 and the non-0157:H7 isolates. FIG. 12 shows that the gas pattern observed for the *E. coli* 0157:H7 showed an initial increase and a period of stabilization followed by a gradual decrease in the voltage readings. FIG. 13 shows that a binary increase in voltage was observed with the non 0157:H7 *E. coli* isolate followed again by a period of tapering off.

Subjectively, there was reliable reproducibility observed between the gas patterns of the replicate experiments on each isolate and within the two groups. The same overall signature shape was seen for the *E. coli* 0157:H7 isolates. There was greater variation in the shape of the gas patterns from the non-0157:H7 isolates. Although four sensors were used in monitoring gas production, only the ammonia, air contaminant, and alcohol sensors showed a response over time. No gas pattern resulted from the hydrogen sulfide sensor, as was anticipated because hydrogen sulfide is not a normal byproduct of *E. coli* metabolism. The temperature and humidity measurements remained constant over time.

The outputs of the three sensors (Ammonia, air contaminant, and alcohol) were used to train and test the neural network classifying *E. coli* 0157:H7. Based on the evaluation of test accuracy (Smith (Smith, In Veterinary Clinical Epidemiology: A Problem Oriented Approach. CRC Press, Ann Arbor, Mich. (1995), pp 31–52), the ANN had high predictive capability for accurately classifying the bacteria based on the output of individual sensors. The results of the sensitivity and specificity analysis for the three sensors and scenarios are presented in Tables 5, 6, and 7.

TABLE 5

Sensitivity and Specificity of the Gas Sensor Based on the ANN Interpretation of the Ammonia Sensor Output

| Interpretation by the ANN Probability of 0157:H7 Considered positive | Ammonia Sensor | | | |
|---|---|---|---|---|
| | Mean Sensitivity (%) | Sensitivity Range (%) | Mean Specificity (%) | Specificity Range (%) |
| 50% | 91.7 | 75–100 | 70.83 | 37.5–100 |
| 60% | 89.6 | 62.5–100 | 70.8 | 37.5–100 |
| 70% | 83.3 | 50–100 | 75 | 50–100 |
| 80% | 77.08 | 50–100 | 75 | 50–100 |
| 90% | 70.8 | 50–100 | 79.2 | 50–100 |

TABLE 6

Sensitivity and Specificity of the Gas Sensor Based on the ANN Interpretation of the Air Contaminants Sensor Output

| Interpretation by the ANN Probability of 0157:H7 Considered positive | Air Contaminants Sensor | | | |
|---|---|---|---|---|
| | Mean Sensitivity (%) | Sensitivity Range (%) | Mean Specificity (%) | Specificity Range (%) |
| 50% | 85.4 | 75–100 | 68.75 | 50–87.5 |
| 60% | 83.3 | 62.5–100 | 68.75 | 50–87.5 |
| 70% | 72.9 | 50–87.5 | 70.83 | 50–87.5 |
| 80% | 68.6 | 50–87.5 | 72.92 | 50–87.5 |
| 90% | 58.3 | 50–87.5 | 83.33 | 62.5–100 |

TABLE 7

Sensitivity and Specificity of the Gas Sensor Based on the ANN Interpretation of the Alcohol Sensor Output

| Interpretation by the ANN Probability of 0157:H7 Considered positive | Alcohol Sensor | | | |
|---|---|---|---|---|
| | Mean Sensitivity (%) | Sensitivity Range (%) | Mean Specificity (%) | Specificity Range (%) |
| 50% | 81.3 | 62.5–100 | 62.5 | 37.5–87.5 |
| 60% | 70.8 | 50–100 | 64.6 | 50–87.5 |
| 70% | 70.8 | 50–100 | 68.8 | 50–87.5 |
| 80% | 70.8 | 50–100 | 68.8 | 50–87.5 |
| 90% | 62.5 | 50–100 | 70.8 | 50–87.5 |

Sensitivity and specificity varies depending on the probability cut-off used to classify the gas signatures as 0157:H7 and non-0157:H7 E. coli. For example, for the first cut-off point, any signature with a 50% or greater probability of being E. coli 0157:H7 was considered "positive." For all sensors, as the probability cut-off point was reduced, the ability to correctly classify E. coli 0157:H7 increased, however, the rate mis-classification of non 0157:H7 E. coli also increased.

This example shows that the apparatus is capable of detecting and differentiating E. coli 0157:H7 from non-0157:H7 E. coli isolates in a laboratory setting. Gas-specific sensors were used to detect volatile compounds produced by bacteria during normal metabolic activity. The gas patterns generated are due to the presence of amines, nitrogenous compounds, and alcohols, which are common metabolic breakdown products known to be associated with E. coli (Moat and Foster, Microbial Physiology ($3^{rd}$). Wiley-Liss. New York, N.Y. (1995)). The hydrogen sulfide sensor did not show a response over time because hydrogen sulfide is not a normal by-product of E. coli metabolism. However, inclusion of the hydrogen sulfide sensor may be important for detecting organisms that emit hydrogen sulfide. The differences observed between the gas patterns of the E. coli 0157:H7 isolates and the non-0157:H7 isolate is likely due to genetically encoded differences between their metabolic pathways. Differences in E. coli metabolism are already taken advantage of in routine differentiation of E. coli 0157:H7 from non-0157:H7 E. coli by biochemical assays.

The sensitivity and specificity of differentiating E. coli 0157:H7 from non-0157:H7 E. coli could be altered depending on what probability level was used as the cut-off point. For each gas sensor, as the probability cut-off point was lowered, the sensitivity of detecting E. coli 0157:H7 increased (See Tables 5, 6, and 7). However, the specificity decreased, which resulted in more non-0157:H7 E. coli being mis-classified as E. coli 0157:H7. Sensitivity is the number of true positives, i.e., signatures from E. coli 0157:H7 correctly identified, whereas specificity specificity is determined by correct classification of true negatives, i.e., signatures from non-0157:H7 E. coli correctly identified. With greater sensitivity, there is a greater probability of correctly identifying E. coli 0157:H7 isolates but the specificity is lower, which results in an increased occurrence of false positives, i.e., incorrect classification of non-0157:H7 E. coli as E. coli 0157:H7. Deciding where to set the probability cut-off is dependent on the goal of the screening procedure. When it is important to detect as many E. coli 0157:H7 isolates as possible, even if that would include false positives, then the probability cut-off is set at a point that maximizes sensitivity. If mis-classification of non-0157:H7 E. coli as E. coli 0157:H7 is undesirable, then the cut-off is set at a point that maximizes specificity.

EXAMPLE 3

This example illustrates the ability of the gas sensor component of the present invention to differentiate between E. coli 0157:H7 and non-0157:H7 E. coli field isolates.

Twenty E. coli isolates were obtained from the Bacteriology Laboratory at the Veterinary Diagnostic Center, University of Nebraska. Most of the isolates were collected as part of an ongoing animal production food safety investigation in Midwestern feedyards. Additional isolates were obtained from an outbreak of human illness caused by E. coli 0157:H7 that had contaminated venison. These isolates had been characterized using biochemical reactions in selective culturing, latex agglutination, and polymerase chain reaction. Of the 20 isolates, 12 were confirmed as E. coli 0157:H7.

Procedures for the bacteria culturing and collection of gas signatures were performed as in Example 1. All isolates were grown in nutrient broth to create stock cultures. The bacteria concentration in the stock cultures was determined by viable plate count procedures. All culturing was performed in a certified Biological Safety Level II laboratory. One experimental run, generating a gas signature, was completed for each isolate. For each run, 10 ml of nutrient broth was placed in a sterile 14 ml polystyrene vial and inoculated with $10^5$ CFU/ml of the isolate. The vial was centrally placed in a 37° C. dry-block heater and the chamber positioned over the culture vial. Each isolate was grown for 16 hours with gas measurements taken every five minutes.

The gas signatures were interpreted by visual observation and computer analysis. Using the general shape of the gas signature patterns that were produced, the gas patterns were visually evaluated for characteristic differences and similarities to the original gas signatures from the eight laboratory isolates as in Example 2. For artificial neural network (ANN) (BRAINMAKER, California Scientific Software (1998) interpretation, the 32 E. coli gas signatures were generated in Example 2 were used to train the ANN for pattern recognition. In the training process, the ANN was configured for pattern recognition and data classification. Gas signatures from all 20 field isolates were subject to interpretation and classification by the trained ANN. Each of the gas signatures, in both training and testing data, were then normalized using the equation $$y=(Xi)-Xmin/Xmax-Xmin$$

wherein Xi is the voltage data point, i is 1, ..., n for all data for each sensor, Xmax is the highest voltage point, and Xmin is the lowest voltage point. This method of normalization was used to reduce variation in the gas patterns caused by background voltage levels or pattern height.

Following normalization, the ANN was retrained with the original 32 gas signatures and then tested with the 20 field samples. The ANN determined a probability that the isolate being tested was an E. coli 0157:H7 or a non-0157:H7 E. coli. For this study, an isolate was classified as E. coli 0157:H7 or non-0157:H7 E. coli based on which probability was higher. For example, if the isolate being tested had a greater probability of being E. coli 0157:H7 than non-0157:H7 E. coli, it was classified as E. coli 0157:H7.

Based upon the results of the gas signature interpretation by ANN using both the normalized data and the non-normalized data, the sensitivity and specificity of the apparatus for distinguishing *E. coli* 0157:H7 from non-0157:H7 *E. coli* was determined (Smith, In Veterinary Clinical Epidemiology: A Problem Oriented Approach. CRC Press, Ann Arbor, Mich. (1995), pp 31–52).

As shown in the examples above, the ammonia, air contaminants, and alcohol sensors detected gases over time which were indicative of volatile breakdown products of bacterial growth and metabolism. Many of the gas signatures shared shape characteristics similar to either the standard *E. coli* 0157:H7 or non-0157:H7 *E. coli* isolated tested supra. However, there was greater variation in the overall form of the gas signatures, which may have been a result of strain variations between the field isolates. The greatest variation in gas signatures was observed among the non-0157:H7 *E. coli* isolates. All of the gas signatures from *E. coli* 0157:H7 isolates shared some general characteristics. However, visually discernable differences in the gas signatures were also observed.

Figure 14:
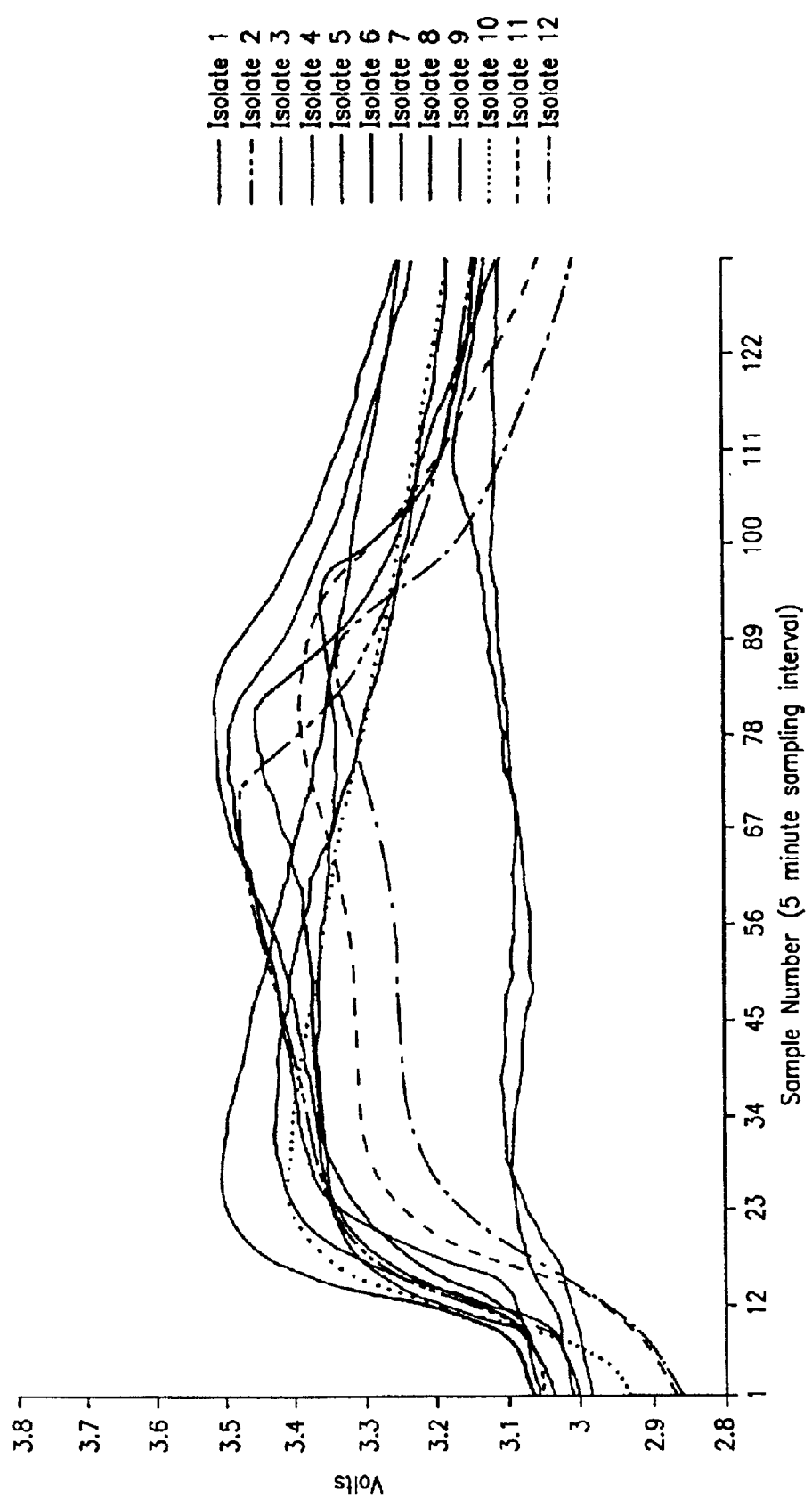
FIG. 14 is a graph of gas signatures from the ammonia sensor for each of the E. coli 0157:H7 field isolates.
Figure 15:
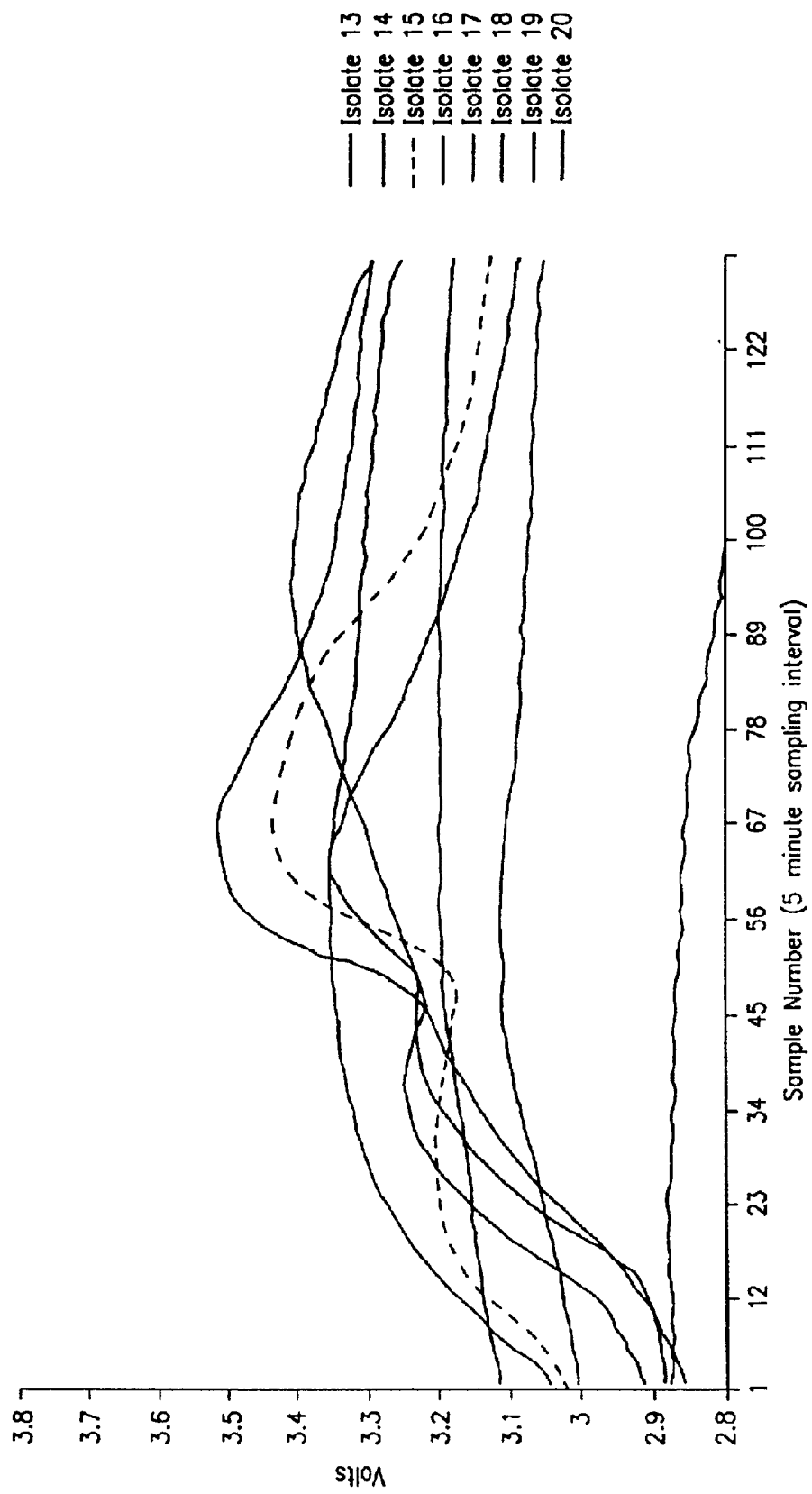
FIG. 15 is a graph of gas signatures from the ammonia sensor for each of the non-0157:H7 E. coli field isolates.
Figure 16:
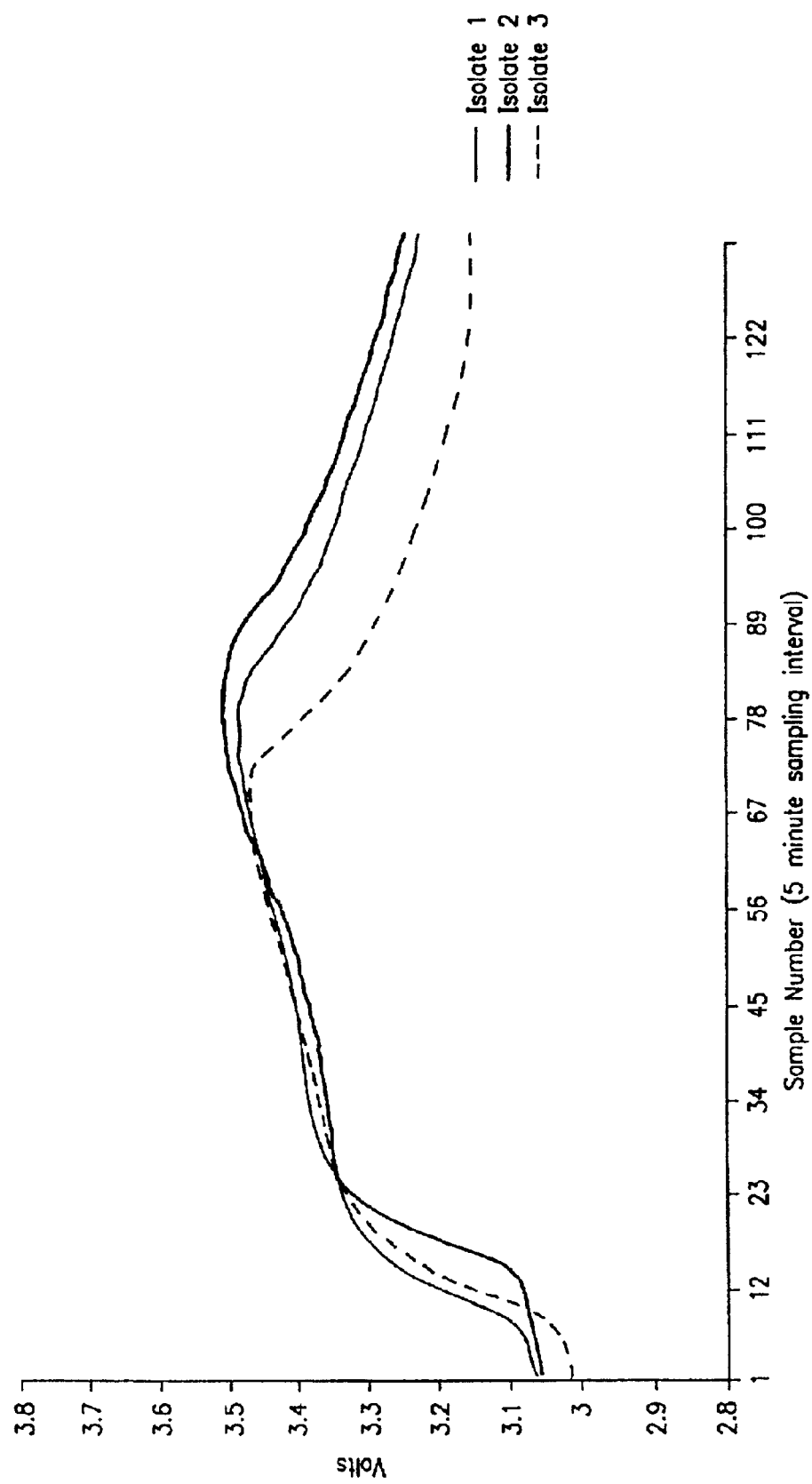
FIG. 16 is a graph of gas signatures from the ammonia sensor for E. coli 0157:H7 field isolates from outbreak of human illness.
Figure 17:
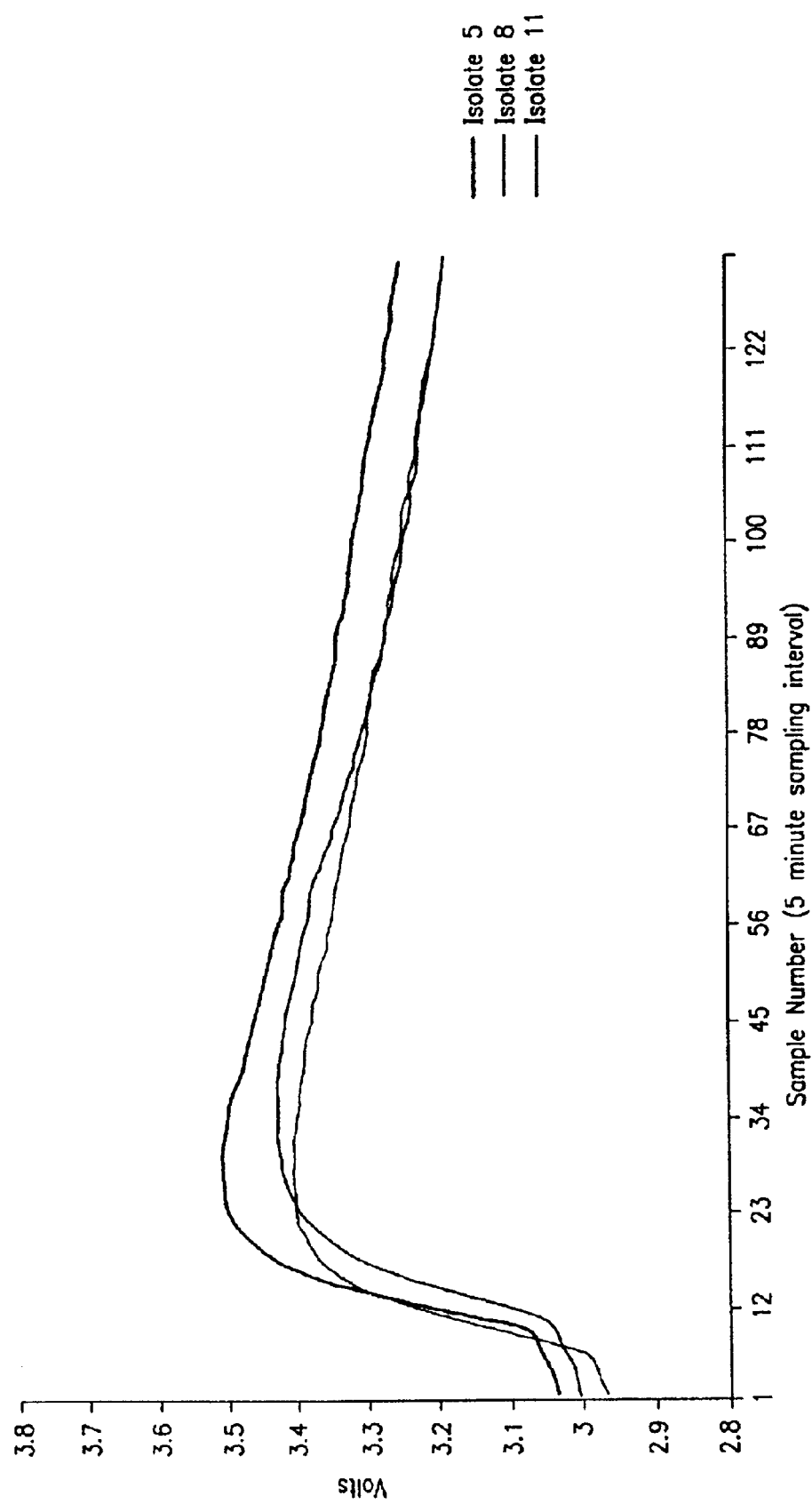
FIG. 17 is a graph of gas signatures from the ammonia sensor for E. coli 0157:H7 isolates from the same feed yard.

FIG. 14 shows the gas signatures from the ammonia sensor for each of the *E. coli* 0157:H7 field isolates and FIG. 15 shows the gas signatures from the ammonia sensor for each of the non-0157:H7 *E. coli* field isolates. Interestingly, *E. coli* 0157:H7 isolates obtained from similar sources produced gas signatures that were visually most closely alike. For example, FIG. 16 shows that the isolates obtained from the outbreak of human illness had very similar signatures and FIG. 17 shows that isolates that were obtained from the same feedlots but at different times and locations showed the same pattern of gas signatures.

Contingency tables showing the frequency of correct classification of the *E. coli* isolates by the ANN based upon the gas signatures from the ammonia, air contaminants, and alcohol sensors using the non-normalized data are shown in Table 9.

TABLE 9

Contingency Tables Showing the Results of ANN Classification of Field Isolates Using Non-Normalized Data

| Ammonia Sensor | True Type 0157:H7 | Non- 0157:H7 | | |
| --- | --- | --- | --- | --- |
| 0157:H7 | 6 | 4 | Sensitivity | 50% |
| Non-0157:H7 | 6 | 4 | Specificity | 50% |

| Air Contaminants Sensor | True Type 0157:H7 | Non- 0157:H7 | | |
| --- | --- | --- | --- | --- |
| 0157:H7 | 5 | 4 | Sensitivity | 41.7% |
| Non-0157:H7 | 7 | 4 | Specificity | 50% |

| Alcohol Sensor | True Type 0157:H7 | Non- 0157:H7 | | |
| --- | --- | --- | --- | --- |
| 0157:H7 | 5 | 4 | Sensitivity | 41.7% |
| Non-0157:H7 | 7 | 4 | Specificity | 50% |

The frequency of correct classification of *E. coli* isolates using normalized data are shown in the contingency tables shown in table 10.

TABLE 10

Contingency Tables Showing the Results of ANN Classification of Field Isolates Using Normalized Data

| Ammonia Sensor | True Type 0157:H7 | Non- 0157:H7 | | |
| --- | --- | --- | --- | --- |
| 0157:H7 | 11 | 4 | Sensitivity | 91.7% |
| Non-0157:H7 | 1 | 4 | Specificity | 50% |

| Air Contaminants Sensor | True Type 0157:H7 | Non- 0157:H7 | | |
| --- | --- | --- | --- | --- |
| 0157:H7 | 12 | 5 | Sensitivity | 100% |
| Non-0157:H7 | 0 | 5 | Specificity | 37.5% |

| Alcohol Sensor | True Type 0157:H7 | Non- 0157:H7 | | |
| --- | --- | --- | --- | --- |
| 0157:H7 | 11 | 4 | Sensitivity | 91.7% |
| Non-0157:H7 | 1 | 4 | Specificity | 50% |

Gas sensor-based technology, in conjunction with ANN, has been previously used to differentiate between classes of bacteria (Gardner et al., Measurement Sci. Technol. 9: 120–127 (1998)). In a previous study, a gas sensor apparatus was developed to differentiate *E. coli* 0157:H7 from non-0157:H7 *E. coli* based upon unique gas signatures generated during bacterial growth under laboratory conditions. Using a limited number of characterized *E. coli* 0157:H7 and non-0157:H7 *E. coli* isolates (n=8), gas signatures were generated and analyzed by ANN. The sensitivity and specificity of this system ranged from 81–92% and 63–71%, respectively, depending on the types of gas signature analyzed.

In this example, the apparatus was able to distinguish *E. coli* 0157:H7 and non-0157:H7 *E. coli* isolates obtained from various field situations, including those associated with an outbreak of clinical human illness and from multiple cattle production systems. Greater variation in the bacterial strains and patterns of gas emissions made the correct classification of the field isolates using the ANN less accurate. Although the overall shape of the gas signatures showed some variation, the isolates of *E. coli* 0157:H7 shared some general visual characteristics. Greater conformity of the gas signatures of the *E. coli* 0157:H7 isolates was seen when the isolates were sorted by source. For example, isolates originating from an outbreak of human illness had virtually identical gas signatures. Isolates obtained from the same feedlot, at different times and from different environmental samples, also had visually similar gas signatures. Similarities in gas patterns of *E. coli* 0157:H7 obtained from the same source may be an indication of relatedness. Based on this observation, unique gas signatures generated by individual strains of *E. coli* 0157:H7 indicates the analysis provided by the present invention has value as an epidemiological tool for determining the relatedness of different *E. coli* 0157:H7 isolates. The non-0157:H7 isolates generated a greater variety of gas signature patterns as more serotypes were represented. The differences between gas signatures from different serotypes could result from the presence or absence of various metabolic processes.

Using an ANN to analyze the gas signatures, a much lower sensitivity and specificity was seen for predicting the class of the field isolates than was observed previously using a limited number of laboratory isolates. However, the sensitivity of the method was greatly improved when the data was normalized. Pattern recognition by ANN was accomplished by comparing voltage readings at each time point during the culture period. Normalizing the data eliminates wide variation in voltage levels that may confuse the ANN. By normalizing the data, interpreting the gas signatures can be made based more on the shape of the gas curves rather than on specific voltage levels.

From the results of the pattern interpretations, it was determined that a larger training set representing more non-0157:H7 *E. coli* serotypes would be desirable in order to train the ANN to more accurately classify non-0157:H7 *E. coli* isolates. However, with the limited training set used herein, *E. coli* 0157:H7 was detected with a high degree of sensitivity, indicating greater similarity of the *E. coli* 0157:H7 gas signatures.

Further refinement of the apparatus and parameters for pattern interpretation can increase the sensitivity and specificity of the apparatus and ANN for classifying *E. coli* isolates. Pattern recognition needs to be focused on determining the most distinctive characteristics of the gas signatures of the *E. coli* 0157:H7 isolates. Additional methods of data normalization for the output from the gas sensors will further improve the accuracy of the ANN. These means of normalizing the data can serve to further reduce the specific types of differences between the gas sensors, which would make pattern recognition by the ANN easier. Preferably, the analytical program that is used for the ANN analysis would allow for greater variation in the gas patterns that were observed for the numerous non-0157:H7 *E. coli* serotypes. Through further development of the analytical tool for interpreting the gas signatures and for normalizing the data, the diagnostic value of the apparatus will be enhanced.

EXAMPLE 4

The current method of detecting soft-rot in potato storage bins consists of visual inspection and odor detection by bin managers. This type of inspection is greatly limited by the thresholds of human senses; often infections are not discovered until considerable damage has been done. These limitations can be overcome by the use of an electronic nose. This example shows the effectiveness of the gas sensing component of the present invention as a potential early-warning diagnostic tool for soft-rot disease.

Six sampling units of the gas sensing component of the present invention were built, each containing an alcohol, relative humidity, and temperature sensor. A drawing illustrating a sampling unit is shown in FIG. 18. FIG. 18A shows the diagram for the heater circuit. FIG. 18B shows the diagram for the TGS 822 (Figaro, Japan) sensor (transducer) and B&B 232 SDA12 A to D converter. The sensors are connected to a data acquisition system. When exposed to a volatile, the outputs of the sensors were changed to electronic signals and sent to the data acquisition system. These signals were read and quantified as a number between 0 and 5 volts. The system allows projection of a real-time graph of all sensor outputs, which gives a constantly updated picture of the relative concentration of volatiles, relative humidity, and temperature of the headspace gas.

The precision, accuracy, and reproducibility of the gas sensing component of the present invention were established. This stage of the experiment was designed to find whether there was a correlation between the concentration of the volatiles in the headspace and the voltage output of the gas sensing component of the present invention. Ethanol, acetone, and isopropanol standards of varying concentrations were used to validate the sensitivity of the gas sensing component of the present invention. The headspace concentration ($C_{headspace}$) of the liquid standard was estimated using the equation $$C_{headspace} = 0.1442(2.316^{T/10})S$$

wherein S is the concentration of the alcohol solution in ppm and T is the temperature in degrees Celsius. For example, to achieve a headspace acetone concentration of 50 ppm, standard solutions were made by adding 57.9 mg of 99.9% liquid acetone to 100 ml distilled water. The standard solutions was placed in glass jars and positioned inside the sampling units for about one hour to enable headspace equilibrium to be achieved before the voltage readings were taken. One of the sampling units was set up as a control, which measured the output from distilled water. The data was logged and analyzed for correlation between headspace concentration and voltage output. A gas chromatograph (GC) was used to corroborate the calculated and measured concentrations of the ethanol standards.

Inoculum of *Erwinia carotovora* var. *carotovora* was prepared from overnight cultures of the bacterium grown in LB broth. The culture was diluted with 0.1 M $MgSO_4$ and adjusted to a concentration of about $10^8$ CFU/ml by measuring the absorbance of the bacterial suspension at 610 nm with a spectrophotometer. Assortments of Snowden potatoes were then inoculated with the bacteria by pipetting 0.1 ml of the fluid culture and stabbing it 1.5 cm into the potatoes with a disposable pipette. Control potatoes were similarly stabbed with empty pipettes. For both, the pipette tips were left in place after stabbing. Once inoculated, the infected potatoes were placed in the sampling units. Data was collected on each set of potatoes every 30 minutes for seven days. This allowed the bacteria infection to peak and level off. The volatiles emitted by the infected potatoes were logged and quantified. After one week, the production of volatiles had leveled and the potatoes were removed. The infected tissue was excised and weighed.

Figure 19:
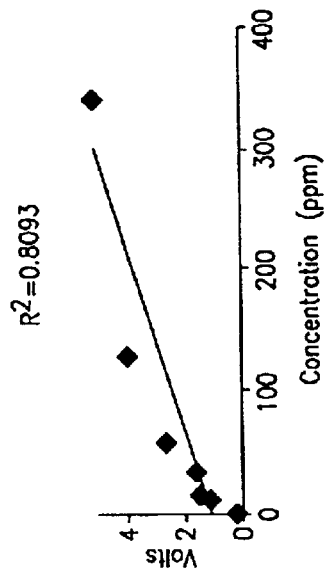
FIGS. 19 to 24 are graphs showing results with a potato sniffer apparatus.
Figure 20:
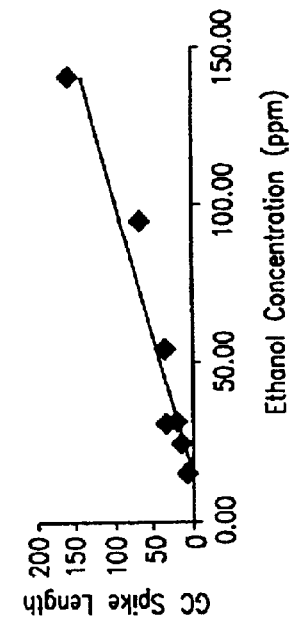
Figure 21:
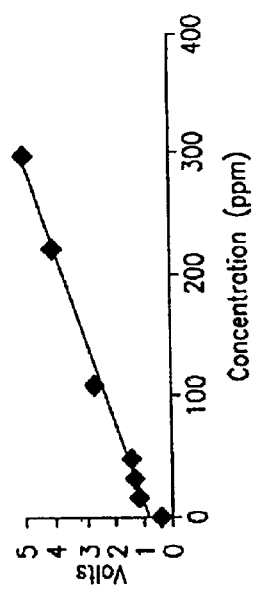
Figure 22:
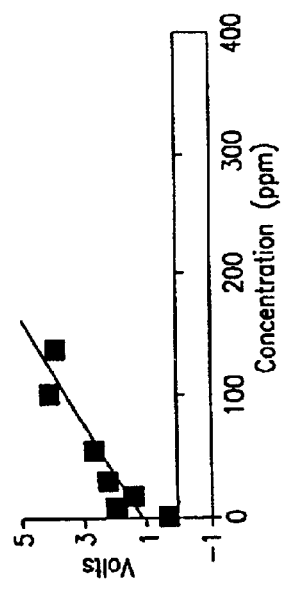

The gas sensing component of the present invention showed that there was a linear relationship between ethanol, acetone, and isopropanol headspace concentrations and voltage output, which are shown in FIGS. 19, 20, and 21, respectively. FIG. 19 shows the sample GC validation for the ethanol standard solution. The zero of the volatile sensor averaged about 0.2 volts. A 5 volt reading was achieved for about 300 ppm of the ethanol standard and the isopropanol standard (FIG. 20) and about 150 ppm for the acetone standard (FIG. 21). FIG. 22 shows that there was a linear relationship between GC spike length and ethanol concentration.

Figure 23:
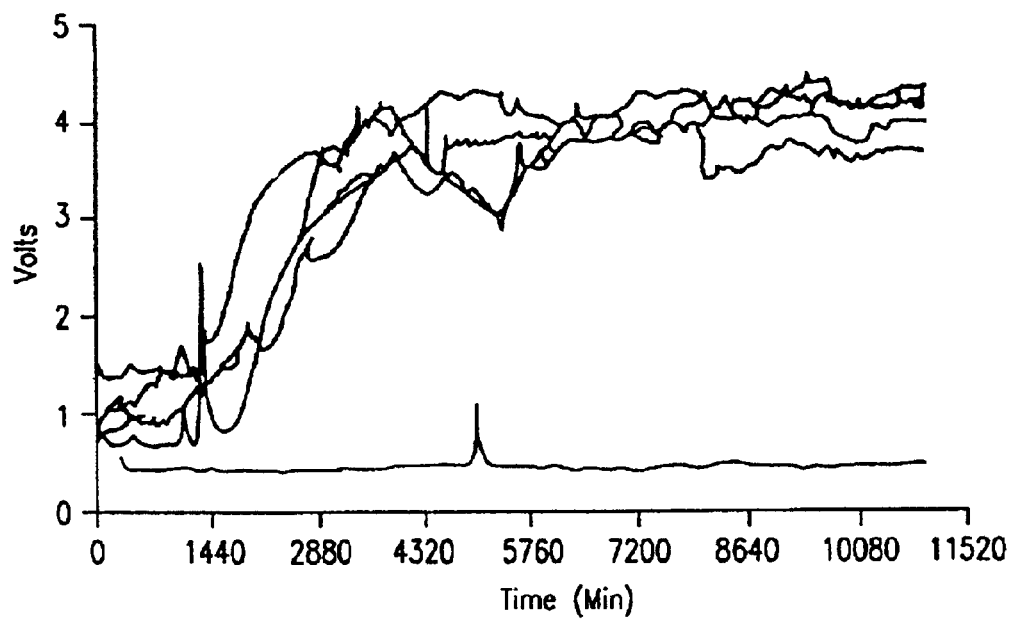
Figure 24:
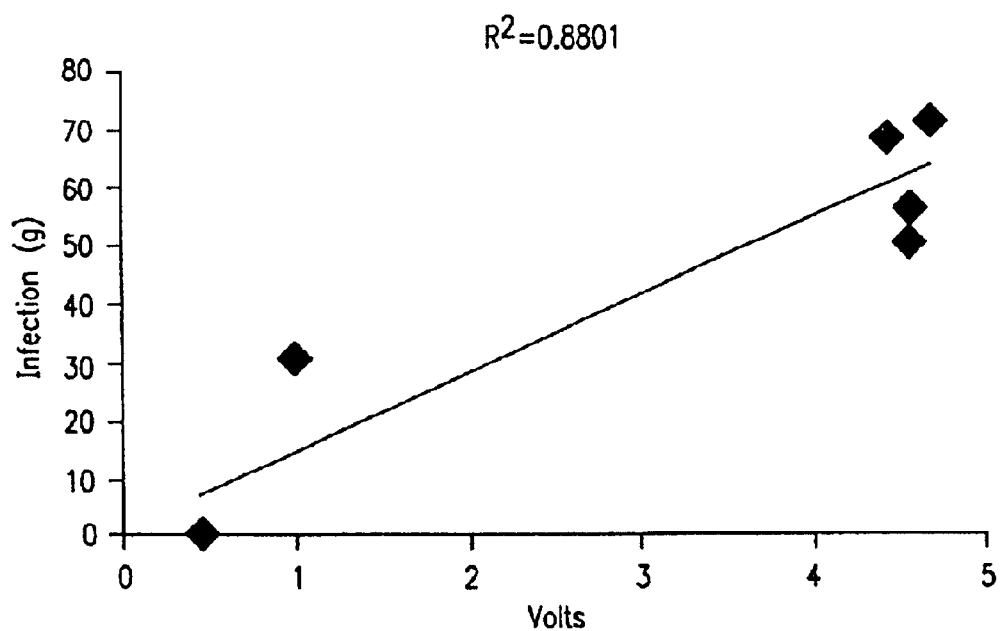

The real-time gas sensor voltage readings of the infected potatoes versus the non-infected potatoes revealed a significant difference in the amount of headspace volatiles produced. The data is shown in FIG. 23 wherein the non-infected potatoes had an average voltage reading of about 0.5 volts over time. In contrast, the five infected potatoes registered a logistic increase in voltage reading over time. The amount of soft-rot infection of the potato was evaluated by measuring the mass of the rotted tissue in grams. FIG. 24 shows that there was a linear relationship between the amount of infection and the voltage output of the sensors. This further indicates that the level of soft-rot infection in the potatoes is directly correlated to headspace volatiles concentrations.

Gas chromatography/mass spectrometry (GC/MS) was used to identify the chemical composition of the volatiles recorded by the gas sensing component. The GC/MS results showed high concentrations of dimethyl disulfide, acetone, isopropanol, 1-butanol, and carbon dioxide.

This example shows that the voltage readings of the gas sensing component of the present invention correlated highly with volatile concentrations and rotted tissues in potatoes. GC/MS analysis of the headspace gases revealed high levels of dimethyl disulfide, acetone, isopropanol, 1-butanol, and carbon dioxide from *E. carotovora*-infected potatoes. The differences that were observed in the voltage readings for a gradient of potato infection illustrates that the gas sensing component of the present invention is able to identify the degree of soft-rot infection in potatoes by emission of volatiles. Use of the gas sensing component of the present invention is simple to use and does not require special training or experience. The gas sensing component is useful to potato farmers and potato distributors. The gas sensing component can save money, time, and waste to the potato industry by providing a low-cost system for detecting volatiles in real-time that allows for the rapid and continuous monitoring of volatiles produced by infected potatoes in potato storage bins.

EXAMPLE 5

This example describes the apparatus of the present invention and illustrates its use in detecting Salmonella grown on Alfalfa sprouts.

FIG. 25 shows a schematic diagram of the apparatus of the present invention. The apparatus comprises the gas sensor chamber comprising the gas sensors, a 35 ml open container (FUV cuvette available from Spectrocell, Inc.), PC plug-in UV-vis spectrometer master channel with grating of 200–850 nm and 25 micron slit and with OFLV detector, spectrometer slave board with 650–1000 nm grating and 25 micron slit, collimating lens, 2 meters each of 300 and 400 micron patch fibers, an ultraviolet (UV), visible (vis), and near infrared (NIR) deuterium tungsten light source, collimating lens holder, personal computer, and block heater. Spectrometer, lenses, and patch fibers can be purchased from Ocean Optics, (Dunedin, Fla.). The apparatus rapidly detects foodborne and waterborne pathogens, such as Salmonella spp., *E. coli* 0157:H7 and other *E. coli* species, and Listeria spp., in packaged plant food products, other food matrices, and environmental samples.

The invention is an improvement over conventional methods for detecting volatile compounds. The conventional method of "seeing" volatile compounds use gas chromatography (GC), which require extensive sample preparation, expensive, and bulky. In some methods, the gases are trapped in appropriate reagents and then analyzed using high-performance liquid chromatography (HPLC). This method requires skilled personnel. GC has not been used to detect pathogen contamination. In contrast to GC, the apparatus of the present invention is portable; it uses a fiber optic PC plug-in spectrometer with an excitation source from the ultraviolet to the near infrared regions of the light spectrum; sample preparation is simple (no technical personnel are required, the user merely places the sample in the cuvette); and the apparatus is used with industries concerned with food safety.

In practice, a sample is placed inside the 35 ml, 10 cm cuvette, which sits on the heating block inside the chamber. The cuvette is connected to two collimating lenses for illumination. The heating block is maintained at 37° C. (optimum temperature for bacterial growth). Gaseous compounds emitted from microbial growth accumulate above the sample inside the headspace of the cuvette. The volatile compounds are detected by the gas sensors and absorption, reflectance, and scattering of the volatile compounds are measured using the UV/vis/NIR fiber optic spectrophotometer. Gas sampling is every five minutes and spectral sampling is every two hours. The gas signatures or patterns and the spectral footprints are analyzed by ANN and compared to standard gas signatures and spectral footprints indicative of the presence of a particular microorganism. When both the gas signature and spectral footprint for the sample match the corresponding standards for a particular microorganism, the sample contains the particular microorganism. Because both the gas signature and the spectral footprint must match to indicate the presence of the particular microorganism, the present invention is more specific than either a gas sensor or spectrophotometer alone.

Figure 26:
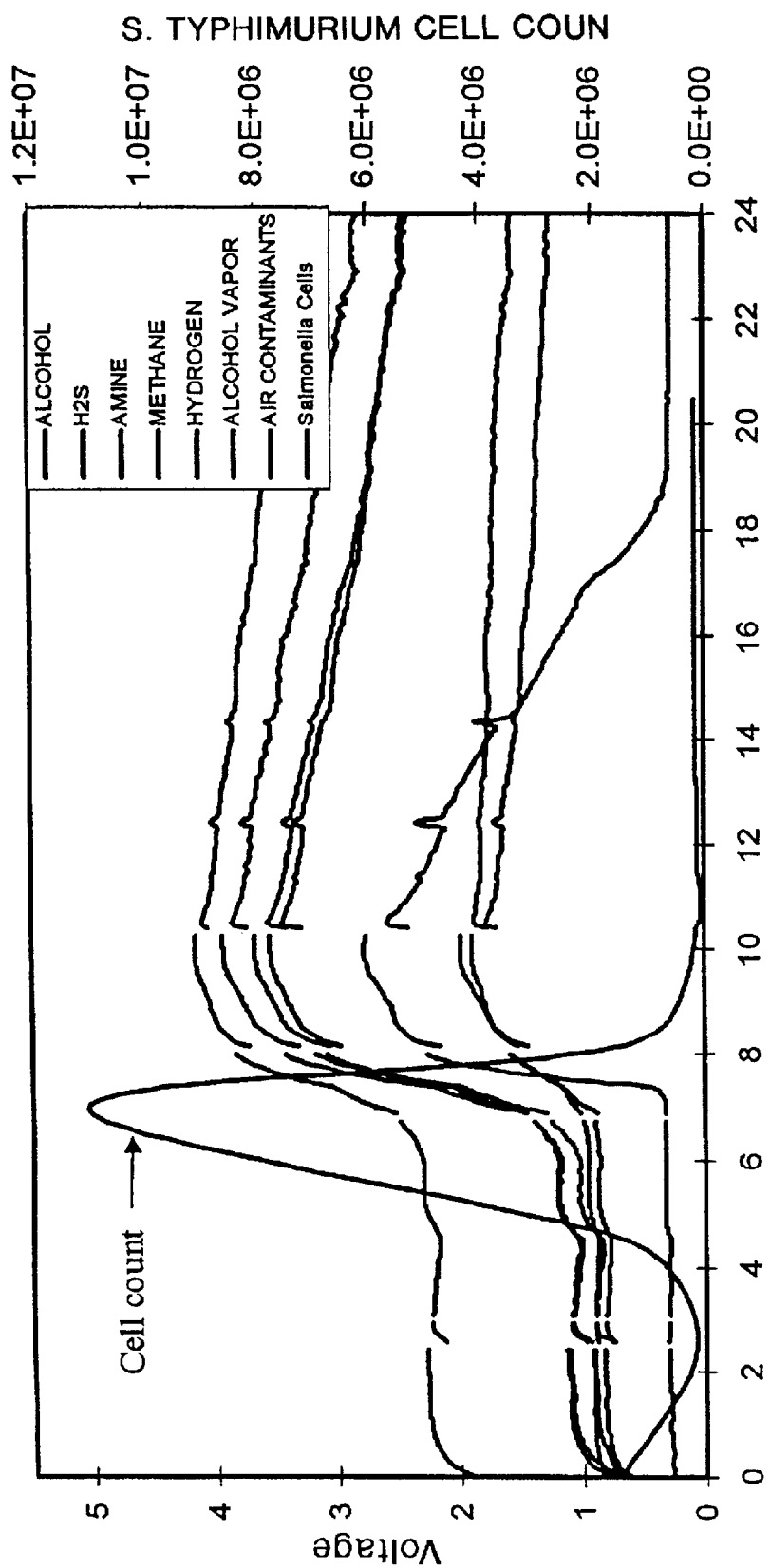
FIG. 26 is a graph showing the typical gas pattern and cell count of S. typhymurium over a 24 hour time period.
Figure 27:
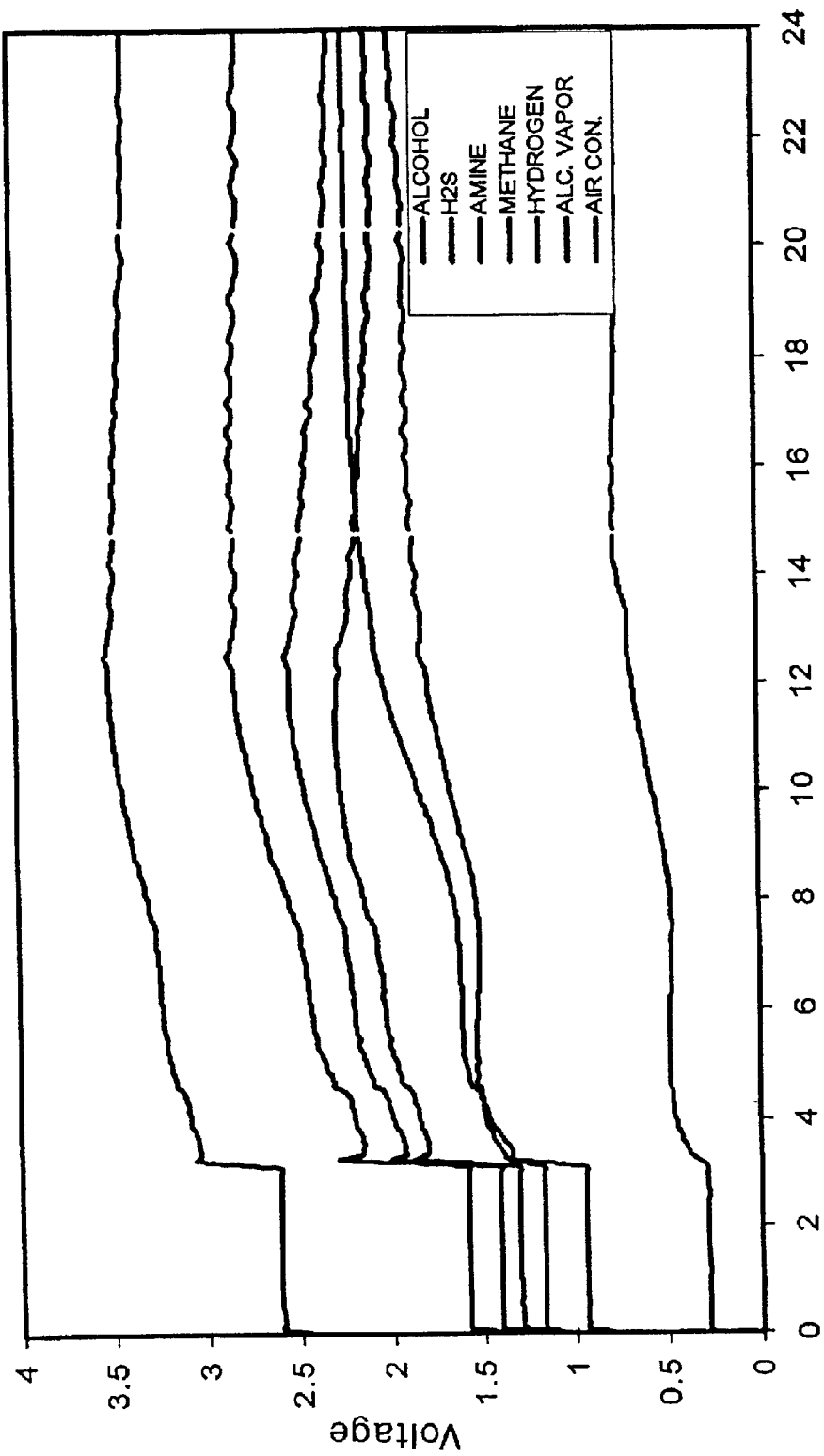
FIG. 27 is a graph showing the gas patterns of S. typhymurium in alfalfa sprouts.
Figure 28:
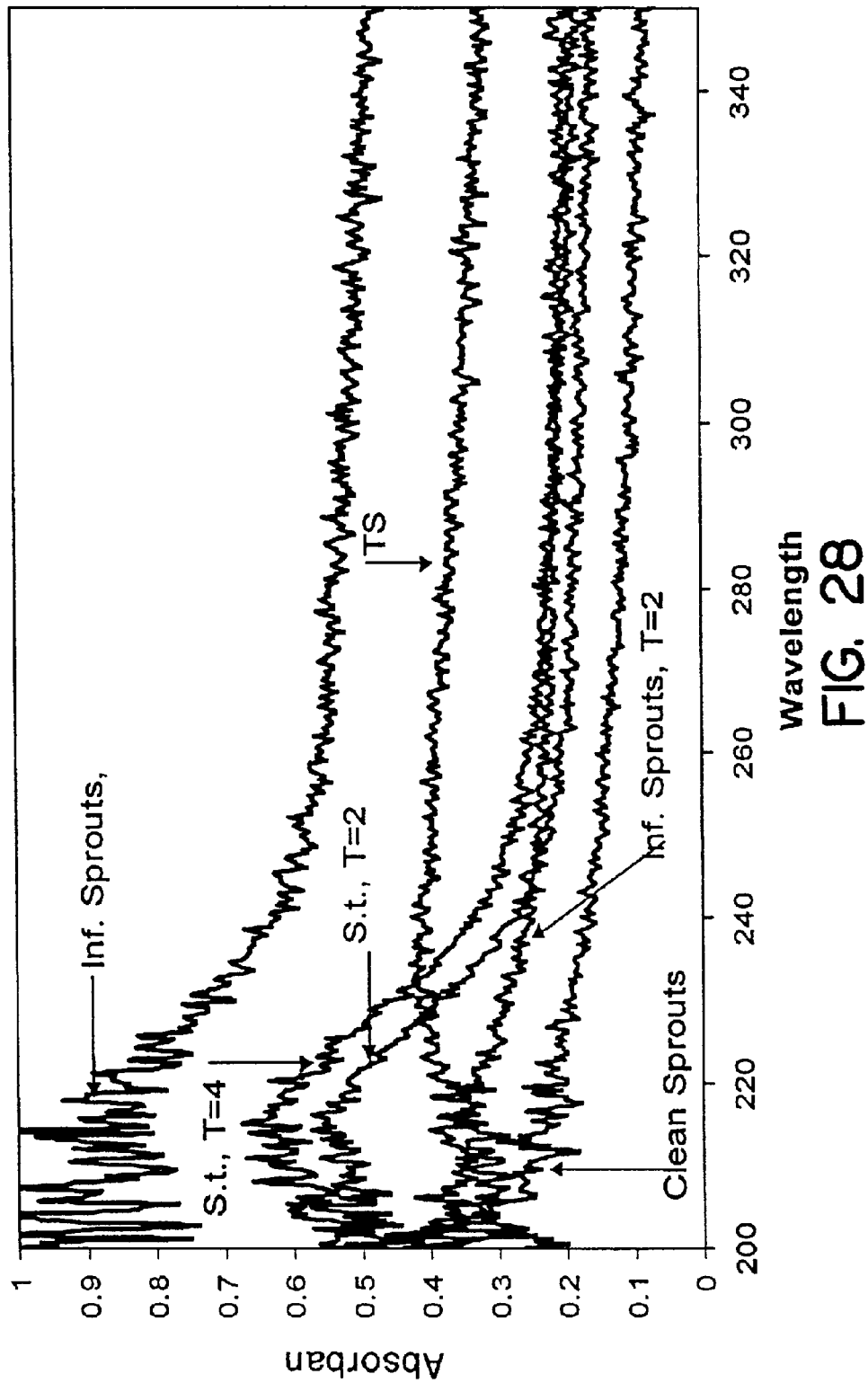
FIG. 28 is a graph showing the spectral footprints of S. typhymurium in TSB and alfalfa sprouts.

FIG. 26 shows the typical gas pattern and cell count of *Salmonella typhymurium*. The graph shows the gas signatures for *S. typhymurium* produced using an alcohol sensor, an $H_2S$ sensor, an amine sensor, a methane sensor, a hydrogen sensor, an alcohol vapor sensor, and an air contaminants sensor. FIG. 27 shows the gas patterns of *S. typhymurium* grown in alfalfa sprouts. The graph shows the gas signatures for *S. typhymurium* produced using an alcohol sensor, an H2S sensor, an amine sensor, a methane sensor, a hydrogen sensor, an alcohol vapor sensor, and an air contaminants sensor. FIG. 28 shows the spectral footprints of the volatile compounds emitted by *S. typhymurium* grown in TSB and on alfalfa sprouts between 200 nm and 340 nm. As can be seen, *S. typhymurium* grown on alfalfa sprouts produces a spectral footprint that is distinguishable from the spectral footprint produced by alfalfa sprouts alone or *S. typhymurium* grown in TSB.

Figure 29:
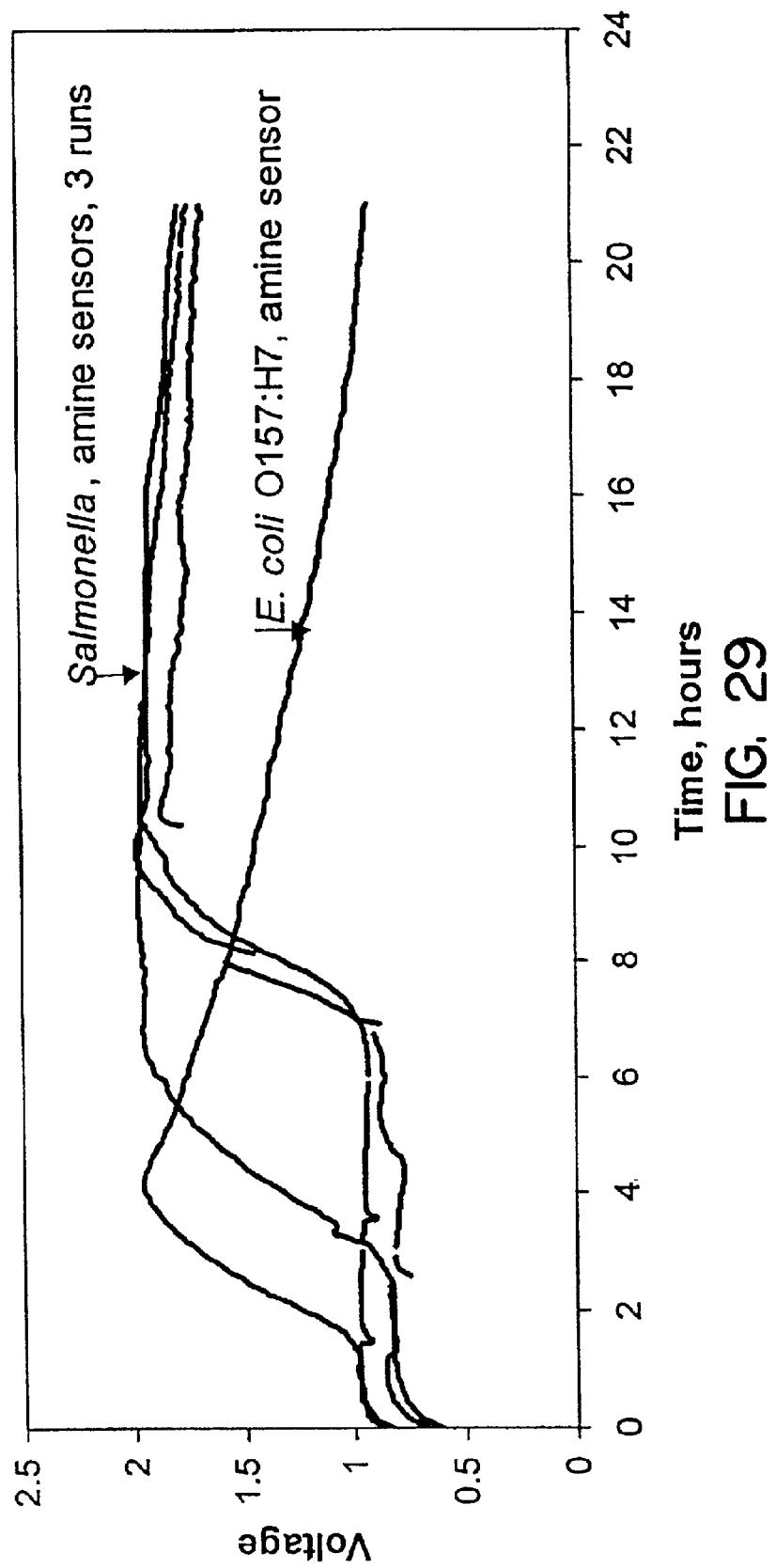
FIG. 29 is a graph showing a gas pattern comparison between S. typhymurium and E. coli 0157:H7 in TSB.

FIG. 29 shows that using the amine sensor, the gas pattern of Salmonella is distinguishable from that of *E. coli* 0157:H7, both grown in TSB.

While the present invention is described herein with reference to illustrated embodiments, it should be understood that the invention is not limited hereto. Those having ordinary skill in the art and access to the teachings herein will recognize additional modifications and embodiments within the scope thereof. Therefore, the present invention is limited only by the claims attached herein.

What is claimed is:

1. An apparatus for detection of volatile products from a sample which comprises:
   (a) a wall or walls defining a confined space comprising therein an open container for containing the sample which produces the volatile products in the confined space, the open container having a bottom with sidewalls extending upwards therefrom to form the open container and wherein the sidewall has two openings positioned to be opposed to each other, each opening having a collimating lens therein;
   (b) one or more transducer means in a circuit mounted on an inner surface of the container defining the confined space which detects one or more volatile products produced from the sample to produce an analog signal;
   (c) an analog to digital conversion means in the circuit for converting the analog signal from the transducer means to a digital signal in the circuit;
   (d) an acquisition means in the circuit which stores the digital signal resulting from the analog signal in memory as a first detectable signal and retrieves the first detectable signal to provide the detection of the one or more volatile products, wherein the one or more volatile products in the confined space are detected by the one or more transducer means over time to produce a gas signature;

(e) a spectrophotometer coupled to the collimating lenses by fiber optics wherein one lens is coupled to the fiber optics from the light source in the spectrophotometer and the opposite lens is coupled to the fiber optics to the light detector in the spectrophotometer so that light absorption or scattering caused by a multiple of the volatile products in the confined space from the sample are detected by the spectrophotometer, to produce a second detectable signal which is a spectral footprint which is stored, and (f) an analyzer including a library of gas signatures and spectral footprints, wherein the analyzer compares the detected gas signature and spectral footprint to the library to determine the volatile products contained in the sample.

2. The apparatus of claim 1 wherein the multiple of volatile products is produced by a microorganism in the sample.

3. The apparatus of claim 2 wherein the microorganism is pathogenic.

4. The apparatus of claim 3 wherein the microorganism is a pathogenic *Escherichia coli*.

5. The apparatus of any one of claims 2 wherein the microorganism is a Salmonella sp.

6. The apparatus of claim 1 wherein the volatile product is selected from the group consisting of ammonia, ammonium compounds, sulfides, amines, ketones, alcohols, methane, butanes, oxides, and carbon dioxide.

7. The apparatus of claim 1 wherein the acquisition means is a computer with a video screen for visualizing the gas signature and spectral footprint.

8. The apparatus of any one of claims 1 to 5 wherein the analyzer is a computer with a video screen for visualizing the gas signature and spectral footprint and wherein in addition the gas signature and spectral footprint are recorded in a graph.

9. The apparatus of claim 8 wherein the computer further comprises an artificial neural network to analyze the gas signature and the spectral footprint by comparing the gas signature and the spectral footprint to a library of gas signatures and spectral footprints stored in the computer.

10. The apparatus of claim 1 wherein the one or more transducer means are mounted in the confined space wherein at least a part of the wall or walls is removable for sealing and unsealing.

11. The apparatus of claim 1 wherein at least one resistor is provided in the circuit with the one or more transducer means to enable reproducible results from the one or more transducer means.

12. The apparatus of claim 1 wherein the analog to digital conversion means is a 12-bit multiple channel analog to digital converter.

13. The apparatus of claim 1 further including a heating block with an opening for holding the open container to maintain the sample at a particular temperature.

14. A method for detecting volatile products from a sample comprising:

(a) providing an apparatus adjacent to the sample which comprises:
   a circuit comprising one or more transducer means mounted on an inner surface of a wall or walls defining a confined space which contains therein an open container for containing the sample which produces the volatile products in the confined space, the open container having a bottom with sidewalls extending upwards therefrom to form the open container and wherein the sidewall has two openings positioned to be opposed to each other, each opening having a collimating lens therein, and wherein the one or more transducer means in the circuit detects one or more volatile products of the volatile products from the sample to produce an analog signal in the circuit;
   an analog to digital conversion means in the circuit for converting the analog signal from the transducer means to a digital signal;
   an acquisition means in the circuit, which stores the digital signal resulting from the analog signal in a memory as a first detectable signal and retrieves the first detectable signal to provide the detection of the one or more volatile products from the sample, wherein the one or more volatile products in the confined space from the sample are detected by the one or more transducer means over time to produce a gas signature;
   a spectrophotometer coupled to the collimating lenses by fiber optics wherein one lens is coupled to the fiber optics from the light source in the spectrophotometer and the opposite lens is coupled to the fiber optics to the light detector in the spectrophotometer so that light absorption or scattering caused by a multiple of the volatile products in the confined space from the sample are detected by the spectrophotometer to produce a second detectable signal which is a spectral footprint which is stored;

(b) detecting the one or more volatile products in the confined space from the sample with the one or more transducer means in the circuit, wherein the one or more volatile products in the confined space from the sample are detected over time to produce the gas signature and wherein the multiple of the volatile products in the confined space from the sample are detected by the spectrophotometer to produce the spectral footprint, and (c) comparing the gas signature and the spectral footprint to a library including a plurality of gas signatures and spectral footprints to determine the volatile products contained in the sample.

15. The method of claim 14 wherein the volatile by-product is selected from the group consisting of ammonia, ammonium compounds, sulfides, amines, ketones, alcohols, methane, butanes, oxides, and carbon dioxide, which is detected repeatedly over a period of time.

16. The method of claim 15 wherein the ammonium is produced by a microorganism.

17. The method of claim 16 wherein the microorganism is a pathogenic *Escherichia coli*.

18. The method of claim 14 wherein the sample in the open container is placed in the confined space which is sealable which is then sealed, and wherein the one or more transducer means are adjacent to the sample in the sealed container.

19. The method of claim 14 wherein the acquisition means further includes an artificial neural network to compare the gas signature and the spectral footprint to the library of gas signatures and spectral footprints stored in the computer.

20. The method of claim 14 wherein the apparatus further includes a heating block with an opening for holding the open container to maintain the sample at a particular temperature.

21. An apparatus for determining whether a food material is spoiling by detecting volatile by-products of the spoiling which comprises:
(a) a circuit comprising one or more transducer means mounted on an inner surface of a wall or walls defining a confined space having therein an open container for containing the food material in the confined space which produces the volatile products, the open container having a bottom with sidewalls extending upwards therefrom to form the open container and wherein the sidewall has two openings positioned to be opposed to each other, each opening having a collimating lens therein, and wherein the one or more transducer means in the circuit detects one or more volatile by-products of the volatile by-products produced in the confined space to produce an analog signal in the circuit;
(b) an analog to digital converter means in the circuit for converting the analog signal from the transducer means to a digital signal;
(c) an acquisition means in the circuit which stores the digital signal resulting from the analog signal in a memory as a first detectable signal and retrieves the first detectable signal to produce the detection of the one or more volatile by-products wherein the one or more volatile by-products are detected by the transducer means over time to produce a gas signature of the one or more volatile by-products;
(d) a spectrophotometer coupled to the collimating lenses by fiber optics, wherein one lens is coupled to the fiber optics from the light source in the spectrophotometer and the opposite lens is coupled to the fiber optics to the light detector in the spectrophotometer so that light absorption or scattering caused by a multiple of the volatile by-products in the confined space from the food material are detected by the spectrophotometer to produce a second signal which is a spectral footprint of the multiple of volatile by-products which is stored, and
(e) an analyzer including a library of gas signatures and spectral footprints, wherein the analyzer compares the detected gas signature and spectral footprint to the library to determine whether a food material is spoiling.

22. The apparatus of claim 21 wherein the transducer means detects a fermentation by-product produced by the microorganism.

23. The apparatus of claim 22 wherein the food material is selected from the group consisting of vegetables, fruits, meats, grains, herbs, spices, and legumes.

24. The apparatus of claim 21 wherein the circuit further comprises a transducer means which detects temperature.

25. The apparatus of claim 21 wherein the circuit further comprises a transducer means which detects humidity.

26. The apparatus of any one of claims 21 to 25 wherein the acquisition means is in a computer with a video screen for visualizing the gas pattern and spectral footprint.

27. The apparatus of any one of claims 21 to 25 wherein the acquisition means is in a computer with a video screen for visualizing the gas pattern and the spectral footprint and wherein the gas pattern and the spectral footprint are recorded in a graph.

28. The apparatus of any one of claims 21 to 25 wherein the transducer means in addition detects temperature, wherein the transducer means in addition detects humidity; and wherein the acquisition means is in a computer which detects each of the humidity, the temperature and the one or more volatile by-products to produce a series of first detectable signals which are reproducible over a series of detections.

29. The apparatus of claim 21 wherein the one or more transducer means are mounted in the confined space wherein at least a part of the wall or walls is removable for sealing and unsealing.

30. The apparatus of claim 29 wherein the transducer means is mounted on a cover for the sealable container.

31. The apparatus of claim 21 wherein at least one resistor is provided in the circuit with the transducer means to enable reproducible results from the transducer means.

32. The apparatus of claim 21 wherein at least one resistor is provided in the circuit with the transducer means to enable reproducible results from the transducer means and wherein the resistor is mounted outside of the container.

33. The apparatus of claim 21 wherein the converter means is a 12-bit multiple channel analog to digital converter.

34. The apparatus of claim 21 further including a heating block with an opening for holding the open container to maintain the sample at a particular temperature.

35. A method for determining whether a biological material is spoiling by detecting volatile by-products which comprises:
(a) providing an apparatus for detecting the volatile by-products produced by the spoiling which comprises:
a circuit comprising one or more transducer means mounted on an inner surface of a wall or walls defining a confined space having therein an open container for containing the biological material which produces the volatile products in the confined space, the open container having a bottom with sidewalls extending upwards therefrom to form the open container and wherein the sidewall has two openings positioned to be opposed to each other, each opening having a collimating lens therein, and wherein the one or more transducer means in the circuit detects one or more of the volatile by-products of the volatile by-products produced in the confined space by the biological material to produce an analog signal;
an analog to digital converter means in the circuit for converting the analog signal from the transducer means to a digital signal;
an acquisition means in the circuit which stores the digital signal resulting from the analog signal in memory as a first detectable signal and retrieves the first detectable signal wherein the one or more volatile by-products in the confined space from the biological material are detected by the one or more transducer means over time to produce a gas signature of the one or more volatile by-products; and
a spectrophotometer coupled to the collimating lens by fiber optics wherein one lens is coupled to the fiber optics from the light source in the spectrophotometer and the opposite lens is coupled to the fiber optics to the light detector in the spectrophotometer so that light absorption or scattering caused by a multiple of the volatile by-products in the confined space is detected by the spectrophotometer to produce a second detectable signal which is a spectral footprint of the multiple of volatile by-products which is stored; and
(b) detecting the one or more volatile by-products of the microorganism with the transducer means in the circuit wherein the one or more volatile by-products in the confined space from the biological material is detected over time to produce the gas signature and wherein the multiple of the volatile products are detected in the confined space by the spectrometer to produce the spectral footprint; and (c) comparing the gas signature and the spectral footprint to a library including a plurality of gas signatures and spectral footprints produced by a plurality of biological materials at different stages of spoilage to determine whether the biological material is spoiling.

36. The method of claim 35 wherein the biological material is a food positioned adjacent to the transducer means.

37. The method of claim 35 wherein the volatile by-product is an alcohol.

38. The method of claim 35 wherein the biological material is selected from the group consisting of vegetables, fruits, meats, grains, herbs, spices, and legumes and the volatile by-product is an alcohol.

39. The method of claim 35 wherein the biological material in the open container is placed in the confined space which is sealable which is then sealed, and wherein the one or more transducer means are adjacent to the biological material in the sealed container.

40. The method of claim 35 wherein the acquisition means is a computer with an artificial neural network to compare the gas signature and the spectral footprint to the library of gas signatures and spectral footprints.

41. The method of claim 35 wherein the apparatus further includes a heating block with an opening for holding the open container to maintain the biological material at a particular temperature.

42. An apparatus for identifying a microorganism in a biological material by detecting volatile by-products produced by the microorganism which comprises:

(a) a circuit comprising one or more transducer means mounted on an inner surface of a wall or walls defining a confined space having therein an open container for containing the biological material with the microorganism which produces the volatile products in the confined space, the open container having a bottom with sidewalls extending upwards therefrom to form the open container and wherein the sidewall has two openings positioned to be opposed to each other, each opening having a collimating lens therein, and wherein the one or more transducer means in the circuit detects one or more volatile by-products of the volatile by-products produced in the confined space by the microorganism in the biological material to produce an analog signal in the circuit;

(b) an analog to digital converter means in the circuit for converting the analog signal from the transducer means to a digital signal;

(c) an acquisition means in the circuit which stores the digital signal resulting from the analog signal in a memory as a first detectable signal and retrieves the first detectable signal to produce the detection of the one or more volatile by-products wherein the one or more volatile by-products are detected by the one or more transducer means over time to produce a gas signature;

(d) a spectrophotometer coupled to the collimating lenses by fiber optics wherein one lens is coupled to the fiber optics from the light source in the spectrophotometer and the opposite lens is coupled to the fiber optics to the light detector in the spectrophotometer so that light absorption or scattering caused by a multiple of volatile by-products from the microorganism in the biological material in the confined space are detected by the spectrophotometer to produce a second signal over time which is stored as a spectral footprint, and (e) an analyzer including a library of gas signatures and spectral footprints, wherein the analyzer compares the detected gas signature and spectral footprint to the library to identify the microorganism.

43. The apparatus of claim 42 wherein the transducer means detects a fermentation by-product produced by the microorganism.

44. The apparatus of claim 42 wherein the biological material is selected from the group consisting of vegetables, fruits, meats, grains, herbs, spices, and legumes.

45. The apparatus of claim 42 wherein the circuit further comprises a transducer means which detects temperature.

46. The apparatus of claim 42 wherein the circuit further comprises a transducer means which detects humidity.

47. The apparatus of any one of claims 42 to 46 wherein the acquisition means is in a computer with a video screen for visualizing the gas signature and spectral footprint.

48. The apparatus of any one of claims 42 to 46 wherein the acquisition means is in a computer with a video screen for visualizing the gas signature and spectral footprint and wherein the gas signature and spectral footprint are recorded in a graph.

49. The apparatus of claim 42 wherein the analyzer is a computer with an artificial neural network to identify the microorganism by comparing the gas signature and the spectral footprint to a library including a plurality of gas signatures and spectral footprints produced by a plurality of microorganisms stored in the computer.

50. The apparatus of any one of claims 42 to 46 or 28 wherein the transducer means in addition detects temperature, wherein the transducer means in addition detects humidity; and wherein the acquisition means is in a computer which detects each of the humidity, the temperature and the one or more volatile by-products to produce a series of first detectable signals which are reproducible over a series of detections.

51. The apparatus of claim 42 wherein the one or more transducer means are mounted in the confined space wherein at least a part of the wall or walls is removable for sealing and unsealing.

52. The apparatus of claim 51 wherein the transducer means is mounted on a cover for the sealable container.

53. The apparatus of claim 42 wherein at least one resistor is provided in the circuit with the transducer means to enable reproducible results from the transducer means.

54. The apparatus of claim 42 wherein at least one resistor is provided in the circuit with the transducer means to enable reproducible results from the transducer means and wherein the resistor is mounted outside of the container.

55. The apparatus of claim 42 wherein the converter means is a 12-bit multiple channel analog to digital converter.

56. The apparatus of claim 42 further including a heating block with an opening for holding the open container to maintain the biological material at a particular temperature.

57. A method for identifying a microorganism in a biological material by detecting a multiple of volatile by-products produced by the microorganism which comprises:

(a) providing an apparatus for the detection of the pattern of the multiple of volatile by-products produced by a microorganism which comprises:

a circuit comprising one or more transducer means mounted on an inner surface of a wall or walls defining a confined space having therein an open container for containing the biological material with the microorganism which produces the volatile products in the confined space, the open container having a bottom with sidewalls extending upwards therefrom to form the open container and wherein the sidewall has two openings positioned to be opposed to each other, each opening having a collimating lens therein, and wherein the one or more transducer means in the circuit detects one or more volatile by-products of the by-products produced by the microorganism in the biological material to produce an analog signal;

an analog to digital converter means in the circuit for converting the analog signal from the transducer means to a digital signal;

an acquisition means in the circuit which stores the digital signal resulting from the analog signal in memory as a first detectable signal and retrieves the first detectable signal to produce a gas signature of the one or more volatile by-products in the confined space; and a spectrophotometer coupled to the collimating lens by fiber optics wherein one lens is coupled to the fiber optics from the light source in the spectrophotometer and the opposite lens is coupled to the fiber optics to the light detector in the spectrophotometer so that light absorption or scattering caused by a multiple of the volatile products in the confined space is detected by the spectrophotometer to produce a second detectable signal which is stored as a spectral footprint;

(b) detecting the one or more volatile by-products in the confined space produced by the microorganism in the biological material with the transducer means in the circuit wherein the one or more volatile by-products is detected over time to produce the gas signature and wherein a multiple of the volatile products in the confined space are detected by the spectrometer to produce the spectral footprint; and (c) comparing the gas signature and the spectral footprint to a library including a plurality of gas signatures and spectral footprints produced by a plurality of microorganisms stored in the acquisition means to identify the microorganism.

58. The method of claim 57 wherein the biological material is a food positioned adjacent to the transducer means.

59. The method of claim 57 wherein the volatile by-product is an alcohol.

60. The method of claim 57 wherein the biological material is selected from the group consisting of vegetables, fruits, meats, grains, herbs, spices, and legumes and the volatile by-product is an alcohol.

61. The method of claim 57 wherein the biological material in the open container is placed in the confined space which is sealable which is then sealed, and wherein the one or more transducer means are adjacent to the biological material in the sealed container.

62. The method of claim 57 wherein the acquisition means is a computer with an artificial neural network to compare the gas signature and the spectral footprint to the library of gas signatures and spectral footprints.

63. The method of claim 57 wherein the apparatus further includes a heating block with an opening for holding the open container to maintain the biological material at a particular temperature.

* * * * *

UNITED STATES PATENT AND TRADEMARK OFFICE
CERTIFICATE OF CORRECTION

PATENT NO. : 6,767,732 B2
DATED : July 27, 2004
INVENTOR(S) : Evangelyn C. Alocilja et al.

It is certified that error appears in the above-identified patent and that said Letters Patent is hereby corrected as shown below:

Column 14,
Lines 26 and 67, "circuit it shown" should be -- circuit is shown --.

Column 15,
Lines 52 and 53, "ability of inability" should be -- ability or inability --.

Column 20,
Line 27, "non-1057:H7" should be -- non-0157:H7 --.

Column 21,
Line 41, "Eased on" should be -- Based on --.

Column 22,
Line 19, "differences n the" should be -- differences in the --.

Column 28,
Line 16, Table 10, "5" should be -- 3 --.

Signed and Sealed this

Fourth Day of January, 2005

JON W. DUDAS
*Director of the United States Patent and Trademark Office*